United States Patent
Ede et al.

(10) Patent No.: US 12,311,019 B2
(45) Date of Patent: May 27, 2025

(54) VACCINE COMPOSITION AND USES THEREOF

(71) Applicant: Imugene Limited, Carlton (AU)

(72) Inventors: Nicholas Ede, Victoria (AU); Ursula Wiedermann, Vienna (AT); Joshua Tobias, Vienna (AT); Christoph Zielinski, Vienna (AT)

(73) Assignee: Imugene Limited, Carlton (AU)

( * ) Notice: Subject to any disclaimer, the term of this patent is extended or adjusted under 35 U.S.C. 154(b) by 1110 days.

(21) Appl. No.: 16/966,442

(22) PCT Filed: Feb. 7, 2019

(86) PCT No.: PCT/AU2019/050089
§ 371 (c)(1),
(2) Date: Jul. 30, 2020

(87) PCT Pub. No.: WO2019/153042
PCT Pub. Date: Aug. 15, 2019

(65) Prior Publication Data
US 2021/0236614 A1    Aug. 5, 2021

(30) Foreign Application Priority Data

Feb. 7, 2018 (AU) ................................ 2018900368
Sep. 19, 2018 (AU) ................................ 2018903518
Oct. 19, 2018 (AU) ................................ 2018903968

(51) Int. Cl.
*A61K 39/00*       (2006.01)
*A61K 39/395*      (2006.01)

(52) U.S. Cl.
CPC ....... *A61K 39/001111* (2018.08); *A61K 39/00* (2013.01); *A61K 39/395* (2013.01); *A61K 2039/55561* (2013.01); *A61K 2039/55572* (2013.01); *A61K 2039/55577* (2013.01); *A61K 2039/575* (2013.01); *A61K 2039/6037* (2013.01)

(58) Field of Classification Search
None
See application file for complete search history.

(56) References Cited

FOREIGN PATENT DOCUMENTS

| WO | WO-2007053455 A2 * | 5/2007 | ............ C07K 14/47 |
|---|---|---|---|
| WO | WO 2013/164694 A1 | 11/2013 | |
| WO | WO 2016/021209 A1 | 2/2016 | |
| WO | WO 2016/106159 A1 | 6/2016 | |
| WO | WO 2016/183469 A1 | 11/2016 | |
| WO | WO 2017/040790 A1 | 3/2017 | |
| WO | WO 2018/183488 A1 | 10/2018 | |

OTHER PUBLICATIONS

Zhu et al, 2022, iScience, vol. 25, N. 103764, 15 pages (Year: 2022).*
O'Donnell et al (Cancer Treatment Reviews, 2017, 53, pp. 71-81) (Year: 2017).*
Ojwang et al (Online Journal of Bioinformatics, 2014, vol. 15, pp. 114-132) (Year: 2014).*
PCT/AU2019/050089, Aug. 11, 2020, International Preliminary Report on Patentability.
PCT/AU2019/050089, Apr. 18, 2019, International Search Report and Written Opinion.
Supplementary European Search Report for EP 19751452.4 dated Oct. 13, 2021.
International Search Report and Written Opinion mailed Apr. 18, 2019 in connection with International Application No. PCT/AU2019/050089.
International Preliminary Report on Patentability dated Aug. 11, 2020 in connection with International Application No. PCT/AU2019/050089.
Huang et al., A totally synthetic, self-assembling, adjuvant-free MUC1 glycopeptide vaccine for cancer therapy. J Am Chem Soc. May 30, 2012;134(21):8730-3. doi: 10.1021/ja211725s. Epub May 17, 2012.
Mittelman et al., Monoclonal and polyclonal humoral immune response to EC HER-2/NEU peptides with low similarity to the host's proteome. Int J Cancer. Apr. 10, 2002;98(5):741-7. doi: 10.1002/ijc.10259.
Potocnakova et al. An Introduction to B-Cell Epitope Mapping and In Silico Epitope Prediction. J Immunol Res. 2016;2016:6760830. doi: 10.1155/2016/6760830. Epub Dec. 29, 2016.
Tobias et al., Enhanced and long term immunogenicity of a Her-2/neu multi-epitope vaccine conjugated to the carrier CRM197 in conjunction with the adjuvant Montanide. BMC Cancer. Feb. 9, 2017;17(1):118. doi: 10.1186/s12885-017-3098-7.
Yao et al., Differential regulation of T and B lymphocytes by PD-1 and SOCS-1 signaling in hepatitis C virus-associated non-Hodgkin's lymphoma. Immunol Invest. 2011;40(3):243-64. doi: 10.3109/08820139.2010.534218. Epub Feb. 3, 2011.
Matsumoto et al., Development of cancer immune adjuvants. 2017;53(1):20-24.
Riemer et al., Mimotope vaccines: epitope mimics induce anti-cancer antibodies. Immunol Lett. Oct. 31, 2007;113(1):1-5. doi: 10.1016/j.imlet.2007.07.008. Epub Aug. 22, 2007. PMID: 17825923; PMCID: PMC2999752.
Yoshida et al., Pharmacological profile and clinical efficacy of human anti-human PD-1 antibody nivolumab (QPDIVO) as a new immune checkpoint inhibitor. Folia Pharmacol Japan. 2015;146:106-114.
Guo et al., Preclinical Studies of a Novel Human PD-1 B-Cell Peptide Cancer Vaccine PD1-Vaxx From BALB/c Mice to Beagle Dogs and to Non-Human Primates (Cynomolgus Monkeys). Front Oncol. May 13, 2022;12:826566. doi: 10.3389/fonc.2022.826566.
Lim et al., Investigation of protein-protein interactions and hot spot region between PD-1 and PD-L1 by fragment molecular orbital method. Sci Rep. Nov. 13, 2019;9(1):16727. doi: 10.1038/s41598-019-53216-z.

* cited by examiner

*Primary Examiner* — Karen A. Canella
(74) *Attorney, Agent, or Firm* — Wolf, Greenfield & Sacks, P.C.

(57) ABSTRACT

Disclosed herein is a vaccine composition for raising a humoral response to PD1, and uses thereof, for treating a cancer characterised by an involvement of PD1, wherein the vaccine composition comprises an effective amount of an immunogen that induces an antibody response in which the antibody binds to a B cell epitope of PD1.

16 Claims, 11 Drawing Sheets

Specification includes a Sequence Listing.

VACCINE COMPOSITION AND USES THEREOF

CROSS REFERENCE TO RELATED APPLICATIONS

This Application is a national stage filing under 35 U.S.C. 371 of International Patent Application Serial No. PCT/AU2019/050089, filed Feb. 7, 2019. Foreign priority benefits are claimed under 35 U.S.C. § 119(a)-(d) or 35 U.S.C. § 365(b) of Australian Application Number 2018903968, filed Oct. 19, 2018, Australian Application Number 2018903518, filed Sep. 19, 2018, and Australian Application Number 2018900368, filed Feb. 7, 2018. The entire contents of these applications are incorporated herein by reference in their entirety.

TECHNICAL FIELD

The present invention relates generally to a vaccine composition for raising a humoral response to programmed cell death protein 1 (PD1), methods of preparing such composition, and uses thereof for the treatment of conditions characterised by the involvement of PD1, such as cancer.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Apr. 22, 2024, is named D009770055US00-SUBSEQ-JDH and is 28,784 bytes in size.

BACKGROUND

Immune checkpoints refer to a plethora of inhibitory pathways hardwired into the immune system that are crucial for maintaining self-tolerance and modulating the duration and amplitude of physiological immune responses in peripheral tissues in order to minimize collateral tissue damage. Many tumours co-opt certain immune-checkpoint pathways as a mechanism of immune resistance, particularly against T cells that are specific for tumour antigens.

The T-cell receptor co-stimulatory pathways have important roles in regulating T-cell activation and tolerance. The B7-CD28 superfamily contains both co-stimulatory and inhibitory receptors, including CD28 and programmed cell death protein 1 (PD1). In general, interactions between PD1 on T cells and its ligand, PD-L1 (B7-H1), control the induction and maintenance of peripheral T-cell tolerance during normal immune responses. The interaction between PD1 and PD-L1 has been described to negatively regulate the proliferation and the cytokine production of T cells. The major role of the PD1 pathway is not at the initial T-cell activation stage, but rather to regulate effector T-cell responses in tissues by downregulating the activity of T cells in order to limit collateral tissue damage. However, in several types of cancers, such as leukemia and multiple myeloma, the surface expression of PD-L1 on cancer cells inhibits cytotoxic lymphocytes due to elevated levels of PD1 on the surface of these T cells. In this regard, PD-L1 is expressed on both malignant cells and infiltrating immune cells in a subset of aggressive B-cell lymphomas. Similarly, the upregulation of PD-L1 expression on myeloma cells has been described to induce T-cell apoptosis and anergy of tumour-specific T cells, as well as enhancing aggressive myeloma-cell characteristics.

Because many of the immune checkpoints are initiated by ligand-receptor interactions, they can be readily blocked by antibodies or modulated by recombinant forms of ligands or receptors. Cytotoxic T-lymphocyte-associated antigen 4 (CTLA4) antibodies were the first of this class of immunotherapeutics to achieve US Food and Drug Administration (FDA) approval (Nature Reviews Cancer, 12, 252-264, 2012). Therapeutic antibodies targeting PD1 and its natural ligand PD-L1 have also been developed and launched more recently (e.g., Opdivo® (by Bristol Myers Squibb) and Keytruda® (by Merck)).

Although potentially of high therapeutic efficacy, the passive administration of monoclonal antibodies suffers from some drawbacks, including the need for frequent administration, the necessity for a prolonged duration, cost intensiveness and targeting only single epitopes. The use of monoclonal antibodies to treat cancers also has its risks and limitations, whereby repeated administration of antibodies can result in adverse effects in some patients, examples of which include infusion reactions, inflammation, autoimmunity and antibody resistance. Thus, there remains an urgent need for an improved method of treating cancer associated with, or characterised by, the involvement of the checkpoint antigen, PD1.

SUMMARY OF THE DISCLOSURE

In an aspect of the present disclosure, there is provided a method of treating a cancer characterised by an involvement of programmed cell death protein 1 (PD1), the method comprising administering to a subject a vaccine composition for raising a humoral response to PD1, wherein the vaccine composition comprises an effective amount of an immunogen that induces an antibody response in which the antibody binds to a B cell epitope of PD1.

In an embodiment, the method further comprises administering to the subject a second immunogen in an effective amount that induces an immune response against a cancer-associated antigen. In yet another embodiment, the method further comprises administering to the subject an antibody, or an antigen-binding fragment thereof, that specifically binds to a cancer-associated antigen.

In another aspect of the present disclosure, there is provided use of a vaccine composition in the preparation of a medicament for the treatment of a cancer characterised by an involvement of PD1, wherein the vaccine composition comprises an effective amount of an immunogen for inducing an antibody response in which the antibody binds to a B cell epitope of PD1, as herein described. In an embodiment, the medicament is formulated for administration with a second immunogen, wherein the second immunogen is present in an effective amount to induce an immune response in a subject against a cancer-associated antigen, as herein described.

In another aspect of the present disclosure, there is provided a vaccine composition for use in treating a cancer characterised by an involvement of PD1, wherein the vaccine composition comprises an effective amount of an immunogen for inducing an antibody response in which the antibody binds to a B cell epitope of PD1, as herein described. In an embodiment, the composition further comprises an effective amount of a second immunogen for inducing an immune response against a cancer-associated antigen, as herein described.

In another aspect of the present disclosure, there is provided a vaccine composition for raising a humoral response to PD1, wherein the vaccine composition comprises an effective amount of an immunogen for inducing an antibody response in which the antibody binds to a B cell epitope of PD1, as herein described. In an embodiment, the composition further comprises an effective amount of a second immunogen for inducing an immune response against a cancer-associated antigen, as herein described.

In an aspect of the present disclosure, there is provided a vaccine composition for raising a humoral response to PD1, wherein the composition comprises an immunogen comprising a peptide sequence that induces an antibody response in which the antibody binds to a B cell epitope of PD1, wherein the peptide sequence comprises at least 8 contiguous amino acid residues of the amino acid sequences selected from the group consisting of SEQ ID NOs: 9, 10, 14, 24, 28, 29, 42, 43, 49 and amino acid sequences having at least 70% sequence identity to any of the foregoing, and wherein the amino acid sequence of the immunogen is not identical to a continuous stretch of at least 50 amino acid residues of PD1.

In another aspect of the present disclosure, there is provided a method of treating a condition characterised by an involvement of PD1, the method comprising administering to a subject in need thereof the vaccine composition as herein described.

In yet another aspect of the present disclosure, there is provided use of the vaccine composition as herein described in the preparation of a medicament for the treatment of a condition characterised by an involvement of PD1.

In yet another aspect of the present disclosure, there is provided a pharmaceutical composition comprising the vaccine composition as herein described and a pharmaceutically acceptable excipient.

In yet another aspect of the present disclosure, there is provided a pharmaceutical composition comprising the vaccine composition as herein described for the treatment of a condition characterised by an involvement of PD1.

DETAILED DESCRIPTION

Figure 1:
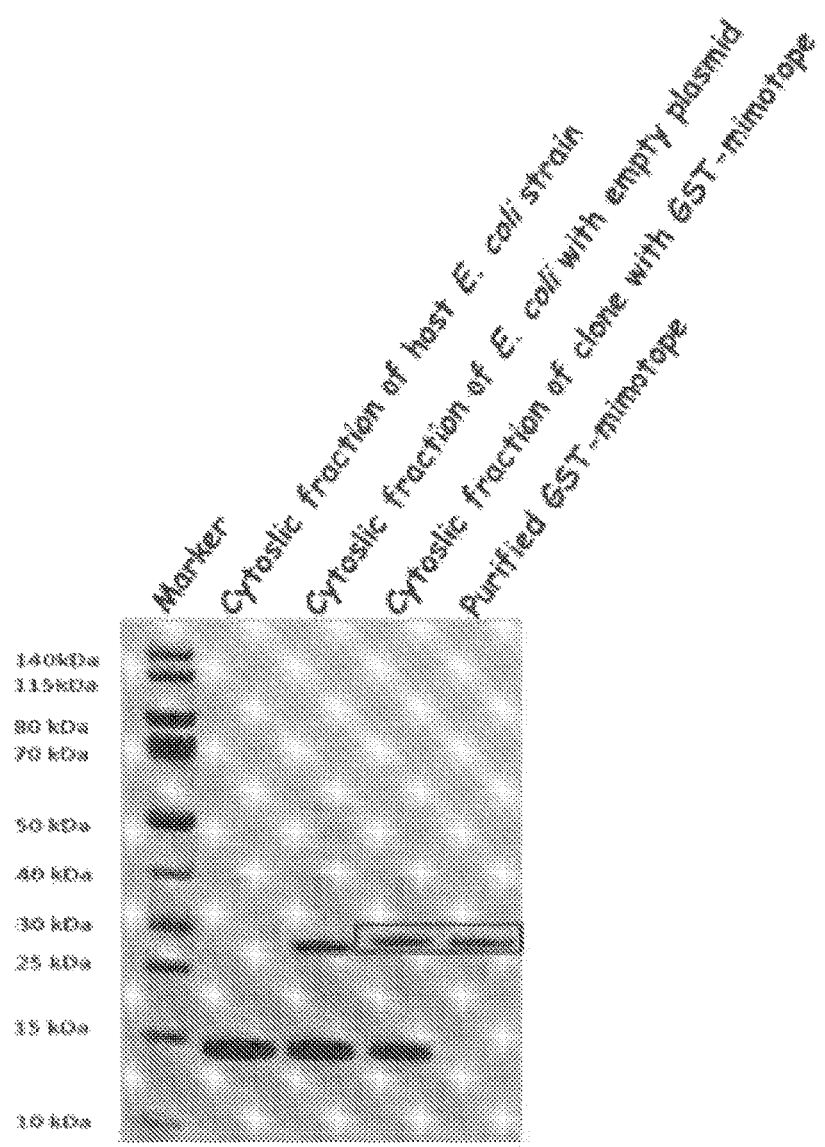
FIG. 1 is a schematic diagram of an NuPage LDS-Page gel showing purified GST-B cell epitopes of PD1. The gel is stained using Simply Blue Safe Stain (Thermo Scientific).
Figure 2:
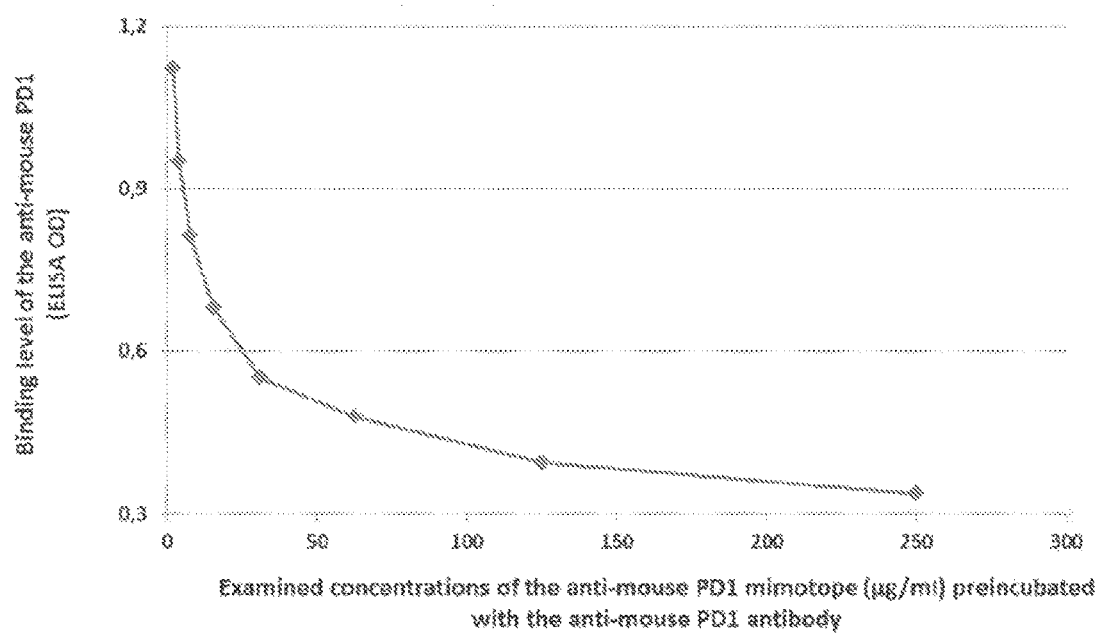
FIG. 2 shows the capacity of the identified B cell epitope of mouse PD1 (SEQ ID NO:119) to inhibit the binding of an anti-mouse-PD1 monoclonal antibody (mAb) to recombinant mouse PD1 (ELISA OD values, 450 nm).
Figure 3:
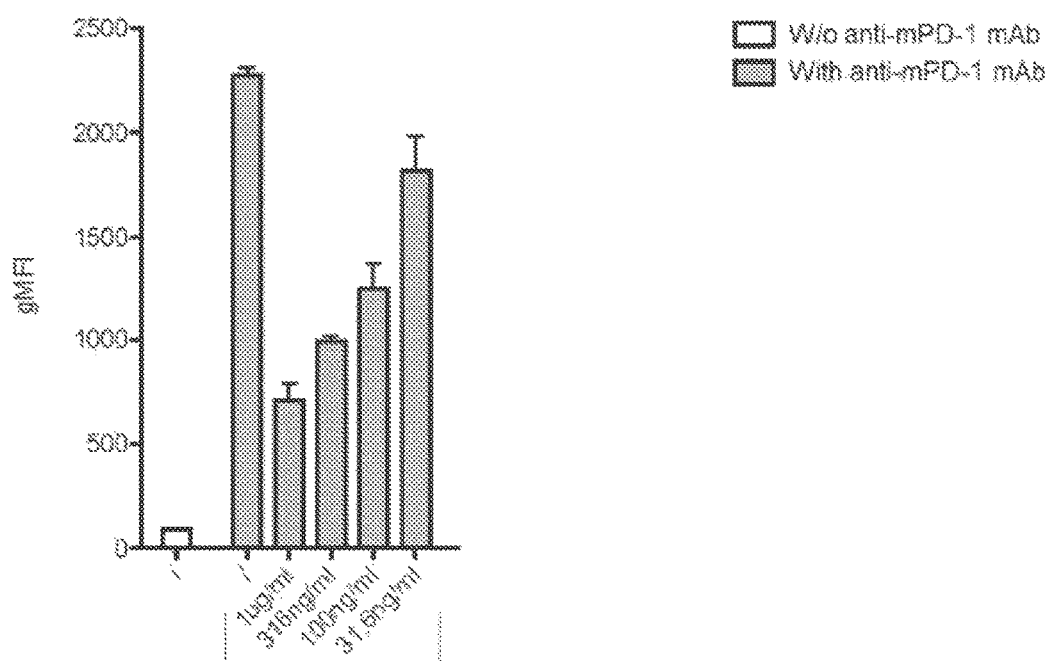
FIG. 3 shows the capacity of the B cell epitope (SEQ ID NO:119) to inhibit the binding of anti-mouse PD-1 mAb to Jurkat T cells expressing mouse PD-1.
Figure 4:
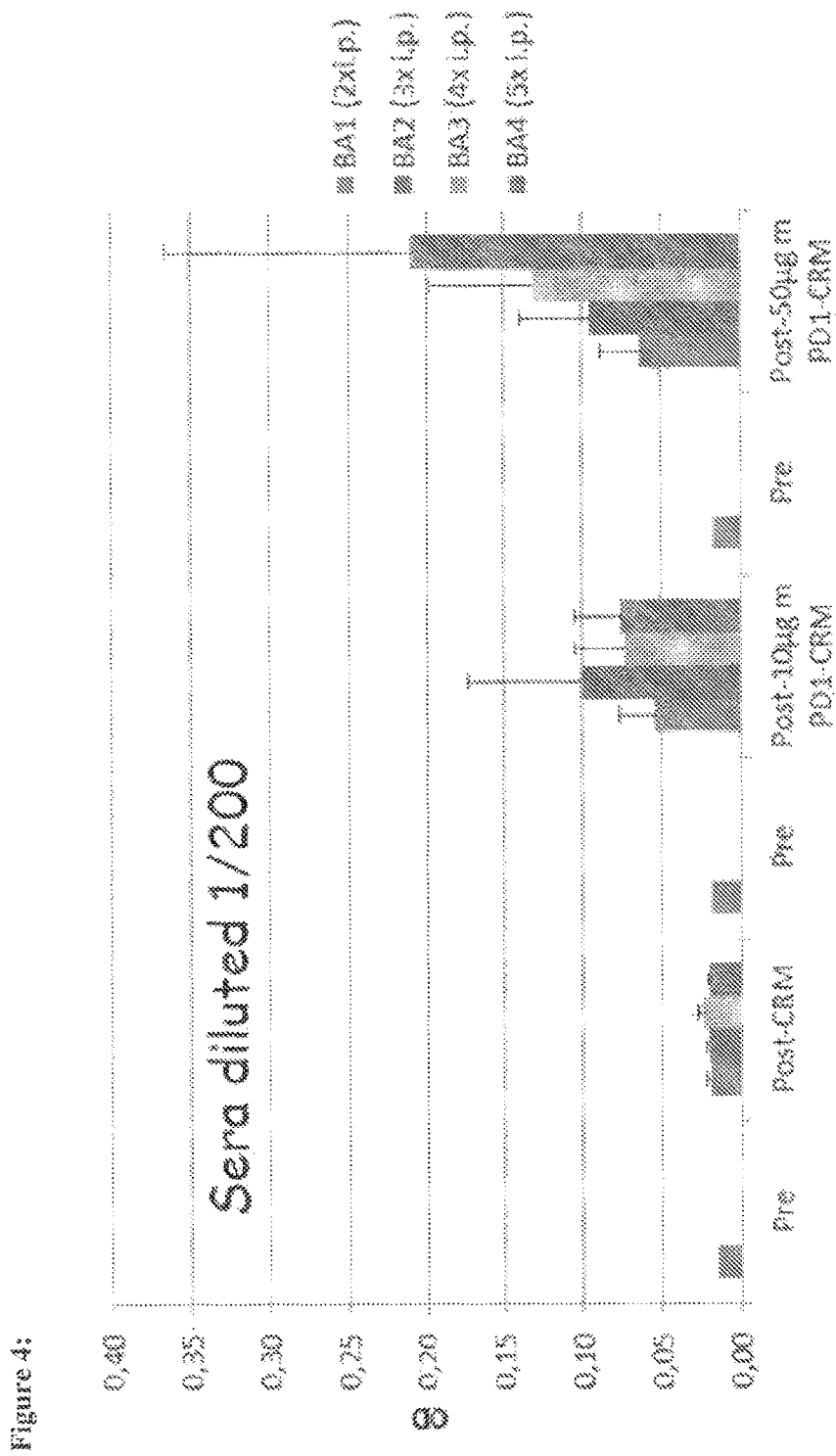
FIG. 4 shows the antibody titre of anti-mPD1 IgG antibodies in the serum of mice immunised with a mPD1 B cell epitope (SEQ ID NO:119)-CRM conjugate, the results showing a clear antibody response to the mPD1 B cell epitope-CRM conjugate, as illustrated by an increased antibody titre at 41 days (BA1), 62 days (BA2), 83 days (BA3) and 104 days (BA4) after the first immunization at day 0 (FIG. 4).

Unless defined otherwise, all technical and scientific terms used herein have the same meanings as commonly understood by one of ordinary skill in the art to which the present disclosure belongs. Any materials and methods similar or equivalent to those described herein can be used to practice the present invention. Practitioners may refer to Sambrook et al., (1989) Molecular Cloning: A Laboratory Manual, 2nd ed., Cold Spring Harbor Press, Plainsview, N.Y., and Ausubel et al. (1999) Current Protocols in Molecular Biology (Supplement 47), John Wiley & Sons, New York, Murphy et al. (1995) Virus Taxonomy Springer Verlag: 79-87, for definitions and terms of the art and other methods known to the person skilled in the art.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein the singular forms "a", "an" and "the" include plural aspects unless the context clearly dictates otherwise. Thus, for example, reference to "a peptide" includes a single peptide, as well as two or more peptides; reference to "an epitope" includes one epitope, as well as two or more epitopes; and so forth.

Nucleotide and amino acid sequences are referred to by sequence identifier numbers (SEQ ID NO:), as shown in Tables 1 and 2, below. The SEQ ID NOs: correspond numerically to the sequence identifiers <400>1, <400>2, etc. A summary of sequence identifiers is provided herein.

TABLE 1

| Amino acid sequences | SEQ ID NO: |
| --- | --- |
| MQIPQAPWPVVWAVLQLGWRPGWFLDSPDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLCGAISLAPKAQIKESLRAELRVTERRAEVPTAHPSPSPRPAGQFQTLV | 1 |
| MQIPQAPWPVVW | 2 |
| PQAPWPVVWAVL | 3 |
| PWPVVWAVLQLG | 4 |
| VVWAVLQLGWRP | 5 |
| AVLQLGWRPGWF | 6 |
| QLGWRPGWFLDS | 7 |
| WRPGWFLDSPDR | 8 |
| GWFLDSPDRPWN | 9 |
| LDSPDRPWNPPT | 10 |
| PDRPWNPPTFSP | 11 |
| PWNPPTFSPALL | 12 |
| PPTFSPALLVVT | 13 |
| FSPALLVVTEGD | 14 |
| ALLVVTEGDNAT | 15 |
| VVTEGDNATFTC | 16 |
| EGDNATFTCSFS | 17 |
| NATFTCSFSNTS | 18 |
| FTCSFSNTSESF | 19 |
| SFSNTSESFVLN | 20 |
| NTSESFVLNWYR | 21 |
| ESFVLNWYRMSP | 22 |
| VLNWYRMSPSNQ | 23 |
| WYRMSPSNQTDK | 24 |
| MSPSNQTDKLAA | 25 |
| SNQTDKLAAFPE | 26 |

TABLE 1-continued

| Amino acid sequences | SEQ ID NO: |
| --- | --- |
| TDKLAAFPEDRS | 27 |
| LAAFPEDRSQPG | 28 |
| FPEDRSQPGQDC | 29 |
| DRSQPGQDCRFR | 30 |
| QPGQDCRFRVTQ | 31 |
| QDCRFRVTQLPN | 32 |
| RFRVTQLPNGRD | 33 |
| VTQLPNGRDFHM | 34 |
| LPNGRDFHMSVV | 35 |
| GRDFHMSVVRAR | 36 |
| FHMSVVRARRND | 37 |
| SVVRARRNDSGT | 38 |
| RARRNDSGTYLC | 39 |
| RNDSGTYLCGAI | 40 |
| SGTYLCGAISLA | 41 |
| YLCGAISLAPKA | 42 |
| GAISLAPKAQIK | 43 |
| SLAPKAQIKESL | 44 |
| PKAQIKESLRAE | 45 |
| QIKESLRAELRV | 46 |
| ESLRAELRVTER | 47 |
| RAELRVTERRAE | 48 |
| LRVTERRAEVPT | 49 |
| TERRAEVPTAHP | 50 |
| RAEVPTAHPSPS | 51 |
| VPTAHPSPSPRP | 52 |
| AHPSPSPRPAGQ | 53 |
| SPSPRPAGQFQL | 54 |
| PRPAGQFQTLV | 55 |
| GWFLDSPDRPWNGAISLAPKAQIK | 56 |
| GAISLAPKAQIKGWFLDSPDRPWN | 57 |
| FVLNWYRMSPSN | 58 |
| NWYRMSPSNQTD | 59 |
| RMSPSNQTDKLA | 60 |
| YLSGAISLAPKA | 61 |
| PSPSPRPAGQFQ | 62 |
| GAISLAPKAQIKESLRAE | 63 |

TABLE 2

| Amino acid sequences | SEQ ID NO: |
|---|---|
| ISLAPKAQIKESLRA | 64 |
| PGWFLDSPDRPWNPP | 65 |
| FLDSPDRPWNPPTFS | 66 |
| SPDRPWNPPTFSPAL | 67 |
| RPWNPPTFSPALLVV | 68 |
| NPPTFSPALLVVTEG | 69 |
| TFSPALLVVTEGDNA | 70 |
| PALLVVTEGDNATFT | 71 |
| LVVTEGDNATFTCSF | 72 |
| TEGDNATFTCSFSNT | 73 |
| DNATFTCSFSNTSES | 74 |
| TFTCSFSNTSESFVL | 75 |
| CSFSNTSESFVLNWY | 76 |
| SNTSESFVLNWYRMS | 77 |
| SESFVLNWYRMSPSN | 78 |
| FVLNWYRMSPSNQTD | 79 |
| NWYRMSPSNQTDKLA | 80 |
| RMSPSNQTDKLAAFP | 81 |
| PSNQTDKLAAFPEDR | 82 |
| QTDKLAAFPEDRSQP | 83 |
| KLAAFPEDRSQPGQD | 84 |
| AFPEDRSQPGQDCRF | 85 |
| EDRSQPGQDCRFRVT | 86 |
| SQPGQDCRFRVTQLP | 87 |
| GQDCRFRVTQLPNGR | 88 |
| CRFRVTQLPNGRDFH | 89 |
| RVTQLPNGRDFHMSV | 90 |
| QLPNGRDFHMSVVRA | 91 |
| NGRDFHMSVVRARRN | 92 |
| DFHMSVVRARRNDSG | 93 |
| MSVVRARRNDSGTYL | 94 |
| VRARRNDSGTYLCGA | 95 |
| RRNDSGTYLCGAISL | 96 |
| DSGTYLCGAISLAPK | 97 |
| TYLCGAISLAPKAQI | 98 |
| CGAISLAPKAQIKES | 99 |
| ISLAPKAQIKESLRA | 100 |
| APKAQIKESLRAELR | 101 |
| AQIKESLRAELRVTE | 102 |
| KESLRAELRVTERRA | 103 |
| LRAELRVTERRAEVP | 104 |
| ELRVTERRAEVPTAH | 105 |
| VTERRAEVPTAHPSP | 106 |
| RRAEVPTAHPSPSPR | 107 |
| EVPTAHPSPSPRPAG | 108 |
| TAHPSPSPRPAGQFQ | 109 |

The present disclosure is predicated, at least in part, on the inventors' surprising finding that immunization with a peptide sequence of a B cell epitope of the checkpoint antigen PD1 is capable of raising an antibody response in which the antibodies bind to the native PD1 protein. The present inventors also surprisingly found that immunization with the PD1-derived B cell epitope did not appear to give rise to any adverse side effects such as weight loss or inflammatory reactions.

Thus, in an aspect of the present disclosure, there is provided a method of treating a cancer characterised by an involvement of programmed cell death protein 1 (PD1), the method comprising administering to a subject a vaccine composition for raising a humoral response to PD1 wherein the vaccine composition comprises an effective amount of an immunogen that induces an antibody response in which the antibody binds to a B cell epitope of PD1.

The present disclosure is also predicated, at least in part, on the inventors' unexpected finding that short peptide sequences of at least 8 contiguous amino acid residues of PD1, when administered to a subject, can induce an antibody response in which the antibodies bind to a B cell epitope of PD1.

Thus, there is also provided a vaccine composition for raising a humoral response to PD1, wherein the composition comprises an immunogen comprising a peptide sequence that induces an antibody response in which the antibody binds to a B cell epitope of PD1, wherein the peptide sequence comprises at least 8 contiguous amino acid residues of the amino acid sequences selected from the group consisting of SEQ ID NOs:9, 10, 14, 24, 28, 29, 42, 43, 49 and amino acid sequences having at least 70% sequence identity to any of the foregoing, and wherein the amino acid sequence of the immunogen is not identical to a continuous stretch of at least 50 amino acid residues of PD1.

Immunogen

The term "immunogen" is used herein to describe a peptide that is capable of raising an immune response, including a humoral (antibody) response, in vivo. The terms "peptide" and "polypeptide" are used interchangeably herein in their broadest sense to refer to a molecule of two or more amino acid residues, or amino acid analogs. The amino acid residues may be linked by peptide bonds, or alternatively by other bonds, e.g. ester, ether etc., but in most cases will be linked by peptide bonds. The terms "amino acid" or "amino acid residue" are used herein to encompass both natural and unnatural or synthetic amino acids, including both the D- or L-forms, and amino acid analogs. An "amino acid analog" is to be understood as a non-naturally occurring amino acid differing from its corresponding naturally occurring amino acid at one or more atoms. For example, an amino acid analog of cysteine may be homocysteine.

By "at least 8 contiguous amino acid residues" is meant 8, 9, 10, 11 or more contiguous amino acid residues of the amino acid sequences selected from the group consisting of SEQ ID NOs:9, 10, 14, 24, 28, 29, 42, 43, 49 and amino acid sequences having at least 70% sequence identity to any of the foregoing. In an embodiment, the immunogen comprises at least 9, preferably at least 10, more preferably at least 11 contiguous amino acid residues of the amino acid sequences selected from the group consisting of SEQ ID NOs:9, 10, 14, 24, 28, 29, 42, 43 and 49 and amino acid sequences having at least 70% sequence identity to any of the foregoing.

In an embodiment, the peptide sequence comprises at least 8 contiguous amino acid residues of the amino acid sequences selected from the group consisting of SEQ ID NOs:9, 10, 14, 24, 28, 29, 42, 43 and 49. In an embodiment, the peptide sequence comprises at least 9 contiguous amino acid residues of the amino acid sequences selected from the group consisting of SEQ ID NOs:9, 10, 14, 24, 28, 29, 42, 43 and 49. In an embodiment, the peptide sequence comprises at least 10 contiguous amino acid residues of the amino acid sequences selected from the group consisting of SEQ ID NOs:9, 10, 14, 24, 28, 29, 42, 43 and 49. In an embodiment, the peptide sequence comprises at least 11 contiguous amino acid residues of the amino acid sequences selected from the group consisting of SEQ ID NOs:9, 10, 14, 24, 28, 29, 42, 43 and 49. In an embodiment, the peptide sequence is selected from the group consisting of SEQ ID NOs:9, 10, 14, 24, 28, 29, 42, 43, 49 and 58-63. In an embodiment, the immunogen consists, or consists essentially of, an amino acid sequence selected from the group consisting of SEQ ID NOs:9, 10, 14, 24, 28, 29, 42, 43, 49 and 58-63.

In an embodiment, the peptide sequence further comprises one or more (i.e., 1, 2, 3, 4, 5, 6, 7, 8. 9, 10, 11, 12, 13, 14, 15, and so on) additional amino acid residues at the N- and/or C terminus of the amino acid sequence selected from the group consisting of SEQ ID NOs:9, 10, 14, 24, 28, 29, 42, 43, 49 and amino acid residues sequences having at least 70% sequence identity to any of the foregoing. In an embodiment, the peptide sequence further comprises one or more amino acid residues at the N- and/or C terminus of the amino acid sequence selected from the group consisting of SEQ ID NOs:9, 10, 14, 24, 28, 29, 42, 43 and 49. By "one or more additional amino acid residues" is meant at least 1, preferably at least 2, preferably at least 3, preferably at least 4, preferably at least 5, preferably at least 6, preferably at least 7, preferably at least 8, preferably at least 9, preferably at least 10, preferably at least 11, preferably at least 12, preferably at least 13 or preferably at least 14 additional amino acid residues. In an embodiment, the peptide sequence comprises at least 13 contiguous amino acid residues of SEQ ID NO:1. In an embodiment, the peptide sequence comprises at least 14 contiguous amino acid residues of SEQ ID NO:1. In an embodiment, the peptide sequence comprises at least 15 contiguous amino acid residues of SEQ ID NO:1. In an embodiment, the peptide sequence comprises at least 16 contiguous amino acid residues of SEQ ID NO:1. In an embodiment, the peptide sequence comprises at least 17 contiguous amino acid residues of SEQ ID NO:1. In an embodiment, the peptide sequence comprises at least 18 contiguous amino acid residues of SEQ ID NO:1. In an embodiment, the peptide sequence will comprise an amino acid sequence selected from the group consisting of SEQ ID NOs:9, 10, 14, 24, 28, 29, 42, 43 and 49, and will further comprise one or more amino acid residues that extend from the C-terminus of the peptide sequence in SEQ ID NO: 1. In another embodiment, the peptide sequence will comprise an amino acid sequence selected from the group consisting of SEQ ID NOs:9, 10, 14, 24, 28, 29, 42, 43 and 49, and will further comprise one or more amino acid residues that extend from the N-terminus of the peptide sequence in SEQ ID NO: 1. In yet another embodiment, the peptide sequence will comprise an amino acid sequence selected from the group consisting of SEQ ID NOs:9, 10, 14, 24, 28, 29, 42, 43 and 49, and will further comprise one or more amino acid residues that extend from the C-terminus and one or more amino acid residues that extend from the N-terminus of the peptide sequence in SEQ ID NO: 1.

In an embodiment, the peptide sequence comprises, consists or consists essentially of an amino acid sequence selected from the group consisting of SEQ ID NOs:58 to 63 and amino acid sequences having at least 70% sequence identity to any of the foregoing. In another embodiment, the peptide sequence comprises, consists or consists essentially of an amino acid sequence selected from the group consisting of SEQ ID NOs:58 to 63. In an embodiment, the peptide sequence comprises, consists or consists essentially of an amino acid sequence of SEQ ID NO:58. In another embodiment, the peptide sequence comprises, consists or consists essentially of an amino acid sequence of SEQ ID NO:59. In another embodiment, the peptide sequence comprises, consists or consists essentially of an amino acid sequence of SEQ ID NO:60. In another embodiment, the peptide sequence comprises, consists or consists essentially of an amino acid sequence of SEQ ID NO:61. In another embodiment, the peptide sequence comprises, consists or consists essentially of an amino acid sequence of SEQ ID NO:62. In another embodiment, the peptide sequence comprises, consists or consists essentially of an amino acid sequence of SEQ ID NO:63.

As noted elsewhere herein, the present inventors have surprisingly found that an immunogen comprising a peptide sequence of at least 8 contiguous amino acid residues of the amino acid sequence of SEQ ID NOs:9 produces a higher anti-PD1 antibody titre when administered in vivo, compared to the other peptide sequences disclosed herein. Thus, in an embodiment, the peptide sequence comprises at least 8 contiguous amino acid residues of SEQ ID NOs:9, or an amino acid sequence having at least 70% sequence identity thereto. In another embodiment, the peptide sequence is selected from the group consisting of SEQ ID NO:9, SEQ ID NO:43, and amino acid sequences having at least 70% sequence identity thereto. In an embodiment, the peptide sequence is selected from the group consisting of SEQ ID NO:9 and SEQ ID NO:43. In an embodiment, the immunogen consists, or consists essentially of, an amino acid sequence selected from the group consisting of SEQ ID NO:9 and SEQ ID NO:43.

In an embodiment, the immunogen comprises at least two of the peptide sequences disclosed herein. In a preferred embodiment, each of the at least two peptide sequences induces an antibody response in vivo in which the antibody binds to a different B cell epitopes of PD1.

By "at least two of the peptide sequences" is meant 1, 2, 3, 4, 5, 6, 7, 8, 9, 10, 11 or more of the peptide sequences described herein. In an embodiment, the immunogen comprises at least 2, preferably at least 3, preferably at least 4, preferably at least 5, preferably at least 6, preferably at least 7, preferably at least 8, or more preferably at least 9 of the peptide sequences described herein. In an embodiment, the immunogen comprises SEQ ID NO:9 and SEQ ID NO:43.

Where the immunogen comprises at least two peptide sequences, the at least two peptide sequences may have a branched or linear configuration. As used herein, the term "fusion protein" typically refers to a polypeptide composed of two or more peptide sequences linked to one another. In an embodiment, the fusion protein comprises two or more peptide sequences linked to one another end-to-end. In an embodiment, the fusion protein comprises two or more peptide sequences linked to one another in a linear configuration via a suitable linking moiety, also referred to herein as a linker. Suitable methods of linking peptide sequences will be familiar to persons skilled in the art, illustrative examples of which include peptide (amide) bonds and linkers.

As used herein, the term "linker" refers to a short polypeptide sequence interposed between any two neighboring peptide sequences as herein described. In an embodiment, the linker is a polypeptide linker of 1 to 10 amino acids, preferably 1, 2, 3, 4 or 5 naturally or non-naturally occurring amino acids. In an embodiment, the linker is a carbohydrate linker. Suitable carbohydrate linkers will be known to persons skilled in the art. In another embodiment disclosed herein, the fusion protein comprises one or more peptidic or polypeptidic linker(s) together with one or more other non-peptidic or non-polypeptidic linker(s). Further, different types of linkers, peptidic or non-peptidic, may be incorporated in the same fusion peptide as deemed appropriate. In the event that a peptidic or polypeptidic linker is used to join two respective peptide sequences, the linker will be advantageously incorporated such that its N-terminal end is bound via a peptide bond to the C-terminal end of the one peptide sequence, and its C-terminal end via a peptide bond to the N-terminal end of the other peptide sequence. The individual peptide sequences within the fusion protein may also have one or more amino acids added to either or both ends, preferably to the C-terminal end. Thus, for example, linker or spacer amino acids may be added to the N- or C-terminus of the peptides or both, to link the peptides and to allow for convenient coupling of the peptides to each other and/or to a delivery system such as a carrier molecule serving as an anchor. An illustrative example of a suitable peptidic linker is LP (leucine-proline).

The immunogen may suitably comprise a fusion protein comprising, consisting, or consisting essentially of any combination of two or more of the peptide sequences disclosed herein. In an embodiment, the fusion protein comprises, consists, or consists essentially of at least three of the peptide sequences disclosed herein.

Fusion protein may comprise the two or more of the peptide sequences disclosed herein in any order, illustrative examples of which include

SEQ ID NO: 9-10,

SEQ ID NO: 10-9,

SEQ ID NO: 9-14,

SEQ ID NO: 14-9,

SEQ ID NO: 10-14,

SEQ ID NO: 14-10,

SEQ ID NO: 9-28,

SEQ ID NO: 10-28,

-continued

SEQ ID NO: 14-28,

SEQ ID NO: 28-9,

SEQ ID NO: 28-10,

SEQ ID NO: 28-14,

SEQ ID NO: 9-29,

SEQ ID NO: 10-29,

SEQ ID NO: 14-29,

SEQ ID NO: 28-29,

SEQ ID NO: 29-9,

SEQ ID NO: 29-10,

SEQ ID NO: 29-14,

SEQ ID NO: 29-28,

SEQ ID NO: 9-10-14,

SEQ ID NO: 9-14-10,

SEQ ID NO: 14-9-10,

SEQ ID NO: 14-10-9,

SEQ ID NO: 10-14-9,

SEQ ID NO: 10-9-14,

SEQ ID NO: 9-10-28,

SEQ ID NO: 9-28-10,

SEQ ID NO: 28-9-10,

SEQ ID NO: 28-10-9,

SEQ ID NO: 10-28-9,

SEQ ID NO: 10-9-28 and so on.

In an embodiment, the fusion protein comprises, consists, or consists essentially of, peptide sequences of SEQ ID NO:9 and SEQ ID NO:43. In an embodiment, the immunogen comprises an amino acid sequence selected from the group consisting of SEQ ID NO:56 and SEQ ID NO:57. In an embodiment, the immunogen consists, or consists essentially of, an amino acid sequence selected from the group consisting of SEQ ID NO:56 and SEQ ID NO:57.

Also contemplated herein are fusion proteins comprising at least two of the peptide sequences disclosed herein, concatenated two or more times in tandem repeat. For example, fusion proteins contemplated herein may comprise two or more tandem repeats of the peptide sequences of at least 8 contiguous amino acid residues of the amino acid sequences selected from the group consisting of SEQ ID NOs:9, 10, 14, 24, 28, 29, 42, 43 and 49 and amino acid sequences having at least 70% sequence identity to any of the foregoing.

Without being bound by theory or by a particular mode of application, it will be understood that incorporating two or more different peptide sequences into the fusion peptide, as herein described, may generate a more beneficial immune response by eliciting a higher antibody titre as compared to an immunogen comprising a single peptide sequence disclosed herein.

Suitable methods of preparing a fusion protein, as herein described, would be familiar to persons skilled in the art. An illustrative example includes peptide synthesis that involves the sequential formation of peptide bonds linking each peptide sequence, as herein described, to its respectively neighboring peptide sequence, and recovering said fusion peptide. Illustrative examples include the methods described in "Amino Acid and Peptide Synthesis" (Oxford Chemistry Primers; by John Jones, Oxford University Press). Synthetic peptides can also be made by liquid-phase synthesis or solid-phase peptide synthesis (SPPS) on different solid supports (e.g. polystyrene, polyamide, or PEG). SPPS may incorporate the use of F-moc (9H-fluoren-9-ylmethoxycarbonyl) or t-Boc (tert-Butoxycarbonyl). Custom peptides are also available from a number of commercial manufacturers.

Alternatively, the fusion protein may be prepared by recombinant methodology. For example, a nucleic acid molecule comprising a nucleic acid sequence encoding the fusion protein can be transfecting into a suitable host cell capable of expressing said nucleic acid sequence, incubating said host cell under conditions suitable for the expression of said nucleic acid sequence, and recovering said fusion protein. Suitable methods for preparing a nucleic acid molecule encoding the fusion protein will also be known to persons skilled in the art, based on knowledge of the genetic code, possibly including optimizing codons based on the nature of the host cell (e.g. microorganism) to be used for expressing and/or secreting the recombinant fusion protein. Suitable host cells will also be known to persons skilled in the art, illustrative examples of which include prokaryotic cells (e.g., *E. coli*) and eukaryotic cells (e.g., *P. pastoris*). Reference is made to "Short Protocols in Molecular Biology, 5th Edition, 2 Volume Set: A Compendium of Methods from Current Protocols in Molecular Biology" (by Frederick M. Ausubel (author, editor), Roger Brent (editor), Robert E. Kingston (editor), David D. Moore (editor), J. G. Seidman (editor), John A. Smith (editor), Kevin Struhl (editor), J Wiley & Sons, London).

As used herein, the terms "encode," "encoding" and the like refer to the capacity of a nucleic acid to provide for another nucleic acid or a polypeptide. For example, a nucleic acid sequence is said to "encode" a polypeptide if it can be transcribed and/or translated, typically in a host cell, to produce the polypeptide or if it can be processed into a form that can be transcribed and/or translated to produce the polypeptide. Such a nucleic acid sequence may include a coding sequence or both a coding sequence and a non-coding sequence. Thus, the terms "encode," "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product. In some embodiments, the nucleic acid sequence encoding the peptide sequences, as herein described, or the fusion proteins, as herein described, are codon-optimised for expression in a suitable host cell. For example, where the fusion protein is to be used for inducing a humoral response against PD1 in a human subject, the nucleic acid sequences can be human codon-optimised. Suitable methods for codon optimisation would be known to persons skilled in the art, such as using the "Reverse Translation" option of "Gene Design" tool located in "Software Tools" on the John Hopkins University Build a Genome website.

As noted elsewhere herein, the peptide sequences can be linked to one another within the fusion peptide by any means known to persons skilled in the art. The terms "link" and "linked" include direct linkage of two peptide sequences via a peptide bond; that is, the C-terminus of one peptide sequence is covalently bound via a peptide bond to the N-terminal of another peptide sequence. The terms "link" and "linked" also include within their meaning the linkage of two peptide sequences via an interposed linker element. It will be understood by persons skilled in the art that, where coupling of the a fusion protein to the carrier protein is via a linker, it is preferable to effect such linker-mediated coupling from the C-terminus of the fusion protein, since linker coupling from the N-terminus may, in some instances, have a negative influence on the desired immune response to be elicited.

In an embodiment disclosed herein, the at least two peptide sequences in a fusion protein are linked to one another via a non-native linker peptide sequence.

Where the immunogen comprises at least two peptide sequences, the peptide sequences may be linked to one another within the fusion peptide in such a way as to ensure the fusion protein comprises an amino acid sequence that is not identical to a continuous stretch of at least 40, preferably at least 50, amino acid residues of native PD1.

By linking at least two peptide sequences in a single fusion protein, wherein each of the at least two peptide sequences induces an antibody response in which the antibody binds to a B cell epitope of a native checkpoint antigen, a homogeneous formulation can be achieved in which only one kind of fusion protein is present. The elements of the fusion protein (i.e. the peptide sequences capable of inducing antibody responses in which the antibodies bind to B cell epitopes of native PD1) may be the same in every fusion protein and can be chosen (or chosen and modified) such that undesired intra- and inter-polypeptide interactions are minimized.

The ratio of the at least two peptide sequences present in the vaccine composition may ultimately be dictated by the ratio of these peptides in the fusion peptide. This means that any desired ratio for eliciting an antibody response to PD1 can be easily and reliably fixed at the level of fusion protein construction and design.

It is to be understood that a fusion peptide may comprise an amino acid sequence of any suitable length, as long as the fusion peptide retains the ability or capacity to induce an antibody response in vivo in which the antibody binds to a B cell epitope of native PD1. In an embodiment, the fusion peptide is at least 16 (e.g., 16, 17, 18, 19, 20, 21, 22, 23, 24, 25, 26, 27, 28, 29, 30, 31, 32, 33, 34, 35, 36, 37, 38, 39, 40 or more) amino acids in length. In an embodiment, the fusion peptide is from about 16 amino acids to about 40 amino acids in length. In an embodiment, the fusion peptide is from about 16 amino acids to about 36 amino acids in length. In an embodiment, the fusion peptide is from about 16 amino acids to about 24 amino acids in length. In an embodiment, the fusion peptide is about 24 amino acids in length.

As used herein, the term "B cell epitope" refers to a part of a molecule that is recognized by an antibody. Thus, a "B cell epitope" is to be understood as being a smaller subsequence of an antigen that is capable of being recognized (bound) by an antibody. It is to be understood that an antigen may contain multiple B cell epitopes, and therefore may be bound by multiple distinct antibodies. A single epitope may also be bound by multiple antibodies having different antigen-binding specificity and/or affinity. Multiple antibodies of different subclasses may also bind to the same epitope.

The immunogen will comprise at least one peptide sequence that, when administered to a subject, will induce an antibody response such that the antibody binds to a B cell epitope of PD1, preferably to a B cell epitope of a native PD1 molecule; that is, to the PD1 antigen as it exists in nature. Preferably, the at least one peptide sequence of the immunogen will induce an antibody response such that the antibody binds to a B cell epitope of the extracellular domain of a native PD1 molecule. Preferably, the B cell epitope to which an antibody is raised will be an epitope located within the extracellular domain of the native antigen. In an embodiment, the immunogen comprises an autologous B cell epitope of PD1; that is, a B cell epitope of PD1 having an amino acid sequence derived from a PD1 molecule of the same species as the subject to be treated.

As used herein, the terms "native" and "natural" refer to the form of a molecule as normally occurring in nature. In an embodiment, the native sequence of PD1 comprises the amino acid sequence of SEQ ID NO:1. Conversely, a "non-native" sequence, including a "non-native linker" is any amino acid sequence not belonging to native sequence of PD1.

The present disclosure also extends to PD1 isoforms of non-human species, including non-human primate, canine, feline, equine, bovine, porcine and murine isoforms of PD1. In an embodiment disclosed herein, the non-human PD1 isoform is a mouse PD1, an illustrative example of which comprises the amino acid sequence of Uniprot No. Q02242, incorporated herein by reference in its entirety.

A peptide sequence having at least 70% sequence identity to any one of SEQ ID NOs:9, 10, 14, 24, 28, 29, 42, 43 and 49, as herein described, is also referred to herein as a "functional variant". It is to be understood that a "functional variant", as used herein, means a peptide sequence that has a different amino acid sequence to a peptide to which it is compared (i.e., a comparator), which may include a natural (i.e., native) sequence or a synthetic variant thereof, yet retains the ability to induce an antibody response in vivo in which the antibody binds to a B cell epitope of PD1.

Suitable methods of determining whether a functional variant retains the ability to induce an antibody response in vivo in which the antibody binds to a B cell epitope of native PD1 will be familiar to persons skilled in the art, illustrative examples of which are described elsewhere herein. For instance, the antibody response elicited by a fusion protein comprising a non-derivatized, native B cell epitope of PD1 can be compared, using the same assay, to that elicited by a fusion protein comprising the variant of the native B cell epitope. If the immune response elicited by the fusion protein comprising the variant is as strong as that elicited by the fusion protein comprising the non-derivatized B cell epitope, then the amino acid substitution can be regarded as functionally equivalent. If the derivatized immune response is superior to the non-derivatized one, then the amino acid substitution can be regarded as improved.

A functional variant may include an amino acid sequence that differs from the native peptide sequence by one or more (e.g., 1, 2, 3, 4, 5, 6, 7, 8, 9 or more) amino acid substitutions, wherein said difference does not, or does not completely, abolish the capacity of the variant to induce an antibody response in which the antibody binds to a B cell epitope of PD1. In some embodiments, the functional variant may comprise amino acid substitutions that enhance the capacity of the peptide sequence to induce an antibody response in which the antibody binds to a B cell epitope of PD1, as compared to the native peptide sequence. In an embodiment, the functional variant differs from the native peptide sequence by one or more conservative amino acid substitutions. As used herein, the term "conservative amino acid substitution" refers to changing amino acid identity at a given position to replace it with an amino acid of approximately equivalent size, charge and/or polarity. Examples of natural conservative substitutions of amino acids include the following 8 substitution groups (designated by the conventional one-letter code): (1) M, I, L, V; (2) F, Y, W; (3) K, R, (4) A, G; (5) S, T; (6) Q, N; (7) E, D; and (8) C, S.

Reference to "at least 70%" includes 70%, 75%, 80%, 85%, 86%, 87%, 88%, 89%, 90%, 91%, 92%, 93%, 94%, 95%, 96%, 97%, 98%, 99% or 100% sequence identity any one of SEQ ID NOs:9, 10, 14, 24, 28, 29, 42, 43 and 49, for example, after optimal alignment or best fit analysis. In an embodiment, the functional variant has at least 70%, preferably at least 75%, preferably at least 80%, preferably at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, preferably at least 99% or preferably 100% sequence identity to any one of SEQ ID NOs:9, 10, 14, 24, 28, 29, 42, 43 and 49, for example, after optimal alignment or best fit analysis.

The terms "identity", "similarity", "sequence identity", "sequence similarity", "homology", "sequence homology" and the like, as used herein, mean that at any particular amino acid residue position in an aligned sequence, the amino acid residue is identical between the aligned sequences. The term "similarity" or "sequence similarity" as used herein, indicates that, at any particular position in the aligned sequences, the amino acid residue is of a similar type between the sequences. For example, leucine may be substituted for an isoleucine or valine residue. This may be referred to as conservative substitution. In an embodiment, the amino acid sequences may be modified by way of conservative substitution of any of the amino acid residues contained therein, such that the modification has no effect on the binding specificity or functional activity of the modified polypeptide when compared to the unmodified polypeptide.

In some embodiments, sequence identity with respect to a peptide sequence relates to the percentage of amino acid residues in the candidate sequence which are identical with the residues of the corresponding peptide sequence after aligning the sequences and introducing gaps, if necessary, to achieve the maximum percentage homology, and not considering any conservative substitutions as part of the sequence identity. Neither N- or C-terminal extensions, nor insertions shall be construed as reducing sequence identity or homology. Methods and computer programs for performing an alignment of two or more amino acid sequences and determining their sequence identity or homology are well known to persons skilled in the art. For example, the percentage of identity or similarity of two amino acid sequences can be readily calculated using algorithms, for example, BLAST, FASTA, or the Smith-Waterman algorithm.

Techniques for determining an amino acid sequence "similarity" are well known to persons skilled in the art. In general, "similarity" means an exact amino acid to amino acid comparison of two or more peptide sequences or at the appropriate place, where amino acids are identical or possess similar chemical and/or physical properties such as charge or hydrophobicity. A so-termed "percent similarity" then can be determined between the compared peptide sequences. In general, "identity" refers to an exact amino acid to amino acid correspondence of two peptide sequences.

Two or more peptide sequences can also be compared by determining their "percent identity". The percent identity of two sequences may be described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). Suitable programs for calculating the percent identity or similarity between sequences are generally known in the art.

Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., "Current Protocols in Molecular Biology", John Wiley & Sons Inc, 1994-1998, Chapter 15.

In an embodiment, a functional variant includes amino acid substitutions and/or other modifications in order to increase the stability of the immunogen and/or to increase the solubility of the immunogen to enhance its ability to induce an antibody response in vivo. Suitable modifications will be familiar to persons skilled in the art, illustrative examples of which are described elsewhere herein.

Peptide sequences disclosed herein can be synthetically produced by chemical synthesis methods which are well known in the art, either as an isolated peptide sequence or as a part of another peptide or polypeptide. Alternatively, peptide sequences can be produced in a microorganism which produces the (recombinant) peptide sequence or sequences, which can then be isolated and, if desired, further purified. The peptide sequences can be produced in microorganisms such as bacteria, yeast or fungi, in eukaryote cells such as a mammalian or an insect cell, or in a recombinant virus vector such as adenovirus, poxvirus, herpesvirus, Simliki forest virus, baculovirus, bacteriophage, sindbis virus or sendai virus. Suitable bacteria for producing the peptide sequences will be familiar to persons skilled in the art, illustrative examples of which include *E. coli, B. subtilis* or any other bacterium that is capable of expressing the peptide sequences. Illustrative examples of suitable yeast types for expressing the peptide sequences include *Saccharomyces cerevisiae, Schizosaccharomyces pombe, Candida, Pichia pastoris* or any other yeast capable of expressing peptides. Corresponding methods are well known in the art. Also methods for isolating and purifying recombinantly produced peptide sequences are well known in the art and include, for example, gel filtration, affinity chromatography and ion exchange chromatography.

To facilitate isolation of a synthetic or recombinant peptide sequence, a fusion polypeptide may be made wherein the at least one peptide sequence is translationally fused (covalently linked) to a heterologous polypeptide which enables isolation by affinity chromatography. Typical heterologous polypeptides are His-Tag (e.g. His$_6$. 6 histidine residues), GST-Tag (Glutathione-S-transferase) etc. The fusion polypeptide facilitates not only the purification of the immunogen but can also prevent the polypeptide from being degraded during purification. If it is desired to remove the heterologous polypeptide after purification the fusion polypeptide may comprise a cleavage site at the junction between the peptide sequence and the heterologous polypeptide. The cleavage site consists of an amino acid sequence that is cleaved with an enzyme specific for the amino acid sequence at the site (e.g. proteases).

The peptide sequences disclosed herein may be suitably modified at or nearby their N- and/or C-termini so that at said positions a cysteine residue is bound thereto.

For preparing peptide sequences, phage libraries and/or peptide libraries are also suitable, for instance, produced by means of combinatorial chemistry or obtained by means of high throughput screening techniques for the most varying structures (see, for example, *Display: A Laboratory Manual* by Carlos F. Barbas (Editor), et al.; and Willats W G *Phage display: practicalities and prospects. Plant Mol. Biol.* 2002 December; 50(6):837-54).

An illustrative example of a suitable functional variant is the peptide sequence of SEQ ID NO:61, noting that SEQ ID NO:61 differs from the corresponding native human PD1 peptide fragment (SEQ ID NO:42) by substituting the cysteine residue at position 3 of SEQ ID NO:42 with a serine residue. Thus, in an embodiment, the functional variant comprises, consists or consists essentially of an amino acid sequence of SEQ ID NO:61.

The antibody response to the peptide sequences disclosed herein may be further enhanced by incorporating into the immunogen a Th cell epitope that promotes the release of cytokines that assist in bypassing MHC restriction (i.e., a promiscuous Th cell epitope). Thus, in an embodiment disclosed herein, the immunogen further comprises a promiscuous T helper (Th) cell epitope. Suitable promiscuous Th cell epitopes will be known to persons skilled in the art, illustrative examples of which include measles virus fusion protein (MVF; KLLSLIKGVIVHRLEGVE; SEQ ID NO:110), tetanus toxoid (TT; NSVDDALINSTIYSYFPSV; SEQ ID NO:111), TT1 (PGINGKAIHLVNNQSSE; SEQ ID NO:112); TT peptide P2 (QYIKANSKFIGITEL; SEQ ID NO:113); TT peptide P30 (FNNFTVSFWLRVPKVSASHLE; SEQ ID NO:114); MVF' (LSEIKGVIVHRLEGV; SEQ ID NO:115); Hepatitis B virus (HBV; FFLLTRILTIPQSLN; SEQ ID NO:116); circumsporozoite protein (CSP; TCGVGVRVRSRV-NAANKKPEl; SEQ ID NO:117), and those described in WO2000/046390, the entire contents of which is incorporated herein by reference. In an embodiment, the promiscuous Th epitope is from about 8 to about 36, preferably from about 8 to about 24, more preferably from about 8 to 22, most preferably from about 8 to about 22 amino acids in length. In an embodiment, the promiscuous Th cell epitope is linked to a peptide sequences or fusion protein, as herein described, to form a chimeric peptide. Suitable linkers will be familiar to persons skilled in the art, illustrative examples of which are described elsewhere herein.

An immunogen will typically comprise at least one peptide sequence (e.g., 1, 2, 3, 4, 5, 6, 7, 8, 9, 10, 11 or more peptide sequences) that induces an antibody response in vivo in which the antibody binds to a B cell epitope of PD1, preferably to a B cell epitope of a native PD1 molecule. The at least one peptide sequence may comprise (i) a B cell epitope of PD1, or a functional variant thereof, (ii) a mimotope of a PD1 B cell epitope or (iii) a combination of any of the foregoing In an embodiment, the immunogen comprises at least one B cell epitope of PD1, or a functional variant thereof. By "at least one" is meant 1, 2, 3, 4, 5, 6, 7, 8, 9, 10, 11 or more. In an embodiment, the immunogen comprises at least 2, preferably at least 3, preferably at least 4, preferably at least 5, preferably at least 6, preferably at least 7, preferably at least 8, preferably at least 9, preferably at least 10, preferably at least 11 or more preferably at least 12 non-contiguous B cell epitopes of PD1, or functional variants thereof. In an embodiment, the immunogen comprises, consists or consists essentially of one B cell epitope of PD1, or a functional variant thereof. In another embodiment, the immunogen comprises, consists or consists essentially of two non-contiguous B cell epitopes of PD1, or functional variants thereof. In another embodiment disclosed herein, the immunogen comprises, consists or consists essentially of three non-contiguous B cell epitopes of PD1, or functional variants thereof.

As used herein, the term "B cell epitope" refers to a part of a molecule that is recognized by an antibody. Thus, a "B cell epitope" is to be understood as being a smaller subsequence of an antigen that is capable of being recognized (bound) by an antibody. It is to be understood that an antigen may contain multiple B cell epitopes, and therefore may be bound by multiple distinct antibodies. A single epitope may also be bound by multiple antibodies having different antigen-binding specificity and/or affinity. Multiple antibodies of different subclasses may also bind to the same epitope.

The immunogen will comprise at least one peptide sequence that, when administered to a subject, will induce an antibody response such that the antibody binds to a B cell epitope of a native PD1 molecule; that is, to the PD1 antigen as it exists in nature. Preferably, the at least one peptide sequence of the immunogen will induce an antibody response such that the antibody binds to a B cell epitope of the extracellular domain of a native PD1 molecule. Preferably, the B cell epitope to which an antibody is raised will be an epitope located within the extracellular domain of the native antigen. In an embodiment, the immunogen comprises an autologous B cell epitope of PD1; that is, a B cell epitope of PD1 having an amino acid sequence derived from a PD1 molecule of the same species as the subject to be treated.

Methods of determining the B cell epitope of PD1 will be familiar to persons skilled in the art. In an illustrative example, a sub-sequence of an antigen may be identified with a high degree of accuracy as being, or comprising, a B cell epitope by using established computer programs that compare the subsequence in question with a database of known sequences and/or partial sequences known to be recognized by antibodies encoded by the human or mouse germline. Alternatively, a B cell epitope may be identified by computer-aided analysis using various combinations of correlates of antigenicity such as surface accessibility, chain flexibility, hydropathy/hydrophilicity profiles, predicted secondary structure, etc. Alternatively, an antigen may be identified as comprising a B cell epitope by immunizing an animal with the antigen in question at least once, allowing a humoral immune response to mount and then testing the serum of the animal for antibodies that specifically bind to at least a part of the administered antigen using, for example, an enzyme linked immunosorbant assay (ELISA), a radioimmunoassay, a Western blot analysis or a dot-blot analysis.

In an embodiment, the B cell epitope is a B cell epitope of human PD1 (SEQ ID NO:1). Tables 1 and 2, above, set out illustrative examples of B cell epitopes of human PD1.

In an embodiment, the B cell epitope of PD1 is selected from the group consisting of SEQ ID NOs:2-109. In a further embodiment, the B cell epitope of PD1 is selected from the group consisting of SEQ ID NOs:9, 43 and 57. In another embodiment disclosed herein, the B cell epitope of PD1 is a functional variant of the B cell epitopes of PD1, illustrative examples of which are provided in Tables 1 and 2 herein (i.e., SEQ ID NOs:2-109).

The present disclosure also extends to PD1 isoforms of non-human species, including non-human primate, canine, feline, equine, bovine, porcine and murine isoforms of PD1. In an embodiment disclosed herein, the non-human PD1 isoform is a mouse PD1, an illustrative example of which comprises the amino acid sequence of Uniprot No. Q02242, incorporated herein by reference in its entirety.

As used herein, the term "functional variant" means a peptide sequence that has a different amino acid sequence to a peptide to which it is compared (i.e., a comparator), which may include a native sequence or an isoform thereof, yet retains the ability, when administered, to induce an antibody response in which the antibody binds to a B cell epitope of PD1. Functional variant include fragments of a PD1 B cell epitope. It is to be understood that a functional fragment of a PD1 B cell epitope can be any suitable length, as long as the fragment retains the ability to induce an antibody response in which the antibody binds to a B cell epitope of PD1, preferably an antibody response in which the antibody binds to a B cell epitope of native PD1.

In an embodiment, the functional variant is a fragment of the PD1 protein of SEQ ID NO:1 comprising, consisting or consisting essentially of the amino acid sequence selected from the group consisting of SEQ ID NOs: 2-109.

In another embodiment, the functional variant is a fragment of the PD1 protein of SEQ ID NO:1 comprising, consisting or consisting essentially of the amino acid sequence selected from the group consisting of SEQ ID NOs:9, 43 and 57.

Suitable methods of determining whether a variant of a B cell epitope of PD1 retains the ability to induce an antibody response in which the antibody binds to a B cell epitope of native PD1 will be familiar to persons skilled in the art, illustrative examples of which are described elsewhere herein. For instance, the antibody response elicited by a fusion protein comprising a non-derivatized, native B cell epitope of PD1 can be compared, using the same assay, to that elicited by a fusion protein comprising the variant of the native B cell epitope. If the immune response elicited by the fusion protein comprising the variant is as strong as that elicited by the fusion protein comprising the non-derivatized B cell epitope, then the amino acid substitution can be regarded as functionally equivalent. If the derivatized immune response is superior to the non-derivatized one, then the amino acid substitution can be regarded as improved.

The term "functional variant" also includes an amino acid sequence that differs from the native sequence by one or more (e.g., 1, 2, 3, 4, 5, 6, 7, 8, 9 or more) amino acid substitutions, wherein said difference does not, or does not completely, abolish the capacity of the variant to induce an antibody response in which the antibody binds to a B cell epitope of PD1. In some embodiments, the functional variant may comprise amino acid substitutions that enhance the capacity of the immunogen to induce an antibody response in which the antibody binds to a B cell epitope of PD1, as compared to the native sequence of that B cell epitope. In an embodiment, the functional variant differs from the native peptide sequence by one or more conservative amino acid substitutions. As used herein, the term "conservative amino acid substitution" refers to changing amino acid identity at a given position to replace it with an amino acid of approximately equivalent size, charge and/or polarity. Examples of natural conservative substitutions of amino acids include the following 8 substitution groups (designated by the conventional one-letter code): (1) M, I, L, V; (2) F, Y, W; (3) K, R, (4) A, G; (5) S, T; (6) Q, N; (7) E, D; and (8) C, S.

In an embodiment, the functional variant has at least 85% sequence identity to an amino acid sequence of a B cell epitope of a native PD1 antigen. Reference to "at least 85%" includes 85%, 86%, 87%, 88%, 89%, 90%, 91%, 92%, 93%, 94%, 95%, 96%, 97%, 98%, 99% or 100% sequence identity or similarity, for example, after optimal alignment or best fit analysis. Thus, in an embodiment, the sequence has at least 85%, preferably at least 86%, preferably at least 87%, preferably at least 88%, preferably at least 89%, preferably at least 90%, preferably at least 91%, preferably at least 92%, preferably at least 93%, preferably at least 94%, preferably at least 95%, preferably at least 96%, preferably at least 97%, preferably at least 98%, preferably at least 99% or preferably 100% sequence identity or sequence homology with the sequences identified herein, for example, after optimal alignment or best fit analysis.

In an embodiment, a functional variant includes amino acid substitutions and/or other modifications in order to increase the stability of the immunogen and/or to increase the solubility of the immunogen to enhance its ability to induce an antibody response in vivo. Suitable modifications will be familiar to persons skilled in the art, illustrative examples of which are described elsewhere herein.

It is to be understood that the immunogen may comprise a peptide sequence of any suitable length, as long as the peptide retains the ability or capacity, when administered to the subject in accordance with the methods disclosed herein, to induce an antibody response in which the antibody binds to a B cell epitope of native PD1. As noted elsewhere herein, methods of determining whether a peptide sequence retains the ability or capacity, when administered, to induce an antibody response in which the antibody binds to a B cell epitope of native PD1 will be familiar to persons skilled in the art. In an embodiment, the peptide sequence is at least 10 (e.g., 10, 11, 12, 13, 14, 15, 16, 17, 18, 19, 20, 21, 22, 23, 24, 25, 26, 27, 28, 29, 30 or more) amino acids in length. In an embodiment, the peptide sequence is from about 10 amino acids to about 40 amino acids in length. In an embodiment, the peptide sequence is from about 10 amino acids to about 35 amino acids in length. In an embodiment, the peptide sequence is from about 10 amino acids to about 30 amino acids in length. In an embodiment, the peptide sequence is from about 10 amino acids to about 25 amino acids in length. In an embodiment, the peptide sequence is from about 10 amino acids to about 20 amino acids in length. In an embodiment, the peptide sequence is from about 10 amino acids to about 15 amino acids in length.

As noted elsewhere herein, the immunogen will comprise at least one peptide sequence that is capable of inducing an antibody response in which the antibody binds to a B cell epitope of PD1, preferably of native PD1. This may be achieved by using peptide sequence comprising an amino acid sequence of a B cell epitope of PD1 (or a functional variant thereof), and/or a mimotope of a PD1 B cell epitope. In an embodiment disclosed herein, the immunogen comprises at least one mimotope of a B cell epitope of PD1.

As used herein, the term "mimotope" typically refers to a molecule that has a conformation that has a topology equivalent to the B cell epitope of which it is a mimic and binds to the same antigen-binding region of an antibody which binds immunospecifically to said B cell epitope. The mimotope will elicit an immunological response in a host that is reactive to the antigen to which it is a mimic.

Mimotopes of PD1 B cell epitopes preferably are antigenic polypeptides which, in their amino acid sequence, vary from the amino acid sequence of a native B cell epitope of PD1. The mimotope may not only comprise amino acid substitutions of one or more naturally occurring amino acid residues of a native PD1 molecule, but also of one or more non-natural amino acids (i.e. not from the 20 "classical" amino acids) or they may be completely assembled of such non-natural amino acids. Suitable mimotopes may be provided from commercially available peptide libraries. Preferably, these mimotopes are at least 7 amino acids in length (e.g., 7, 8, 9, 10, 11, 12, 13, 14, 15, 16, 17 or more amino acids in length). Preferred lengths may be up to 16, preferably up to 14 or 20 amino acids (e.g. 5 to 16 amino acid residues). Longer mimotopes may also be employed. In an embodiment, the mimotope may be part of a polypeptide and consequently comprising at their N- and/or C-terminus at least one further amino acid residue.

Peptide sequences disclosed herein can be synthetically produced by chemical synthesis methods which are well known in the art, either as an isolated peptide sequence or as a part of another peptide or polypeptide. Alternatively, peptide sequences can be produced in a microorganism which produces the (recombinant) peptide sequence or sequences, which can then be isolated and, if desired, further purified. The peptide sequences can be produced in microorganisms such as bacteria, yeast or fungi, in eukaryote cells such as a mammalian or an insect cell, or in a recombinant virus vector such as adenovirus, poxvirus, herpesvirus, Simliki forest virus, baculovirus, bacteriophage, sindbis virus or sendai virus. Suitable bacteria for producing the peptide sequences will be familiar to persons skilled in the art, illustrative examples of which include *E. coli, B. subtilis* or any other bacterium that is capable of expressing the peptide sequences. Illustrative examples of suitable yeast types for expressing the peptide sequences include *Saccharomyces cerevisiae, Schizosaccharomyces pombe, Candida, Pichia pastoris* or any other yeast capable of expressing peptides. Corresponding methods are well known in the art. Also methods for isolating and purifying recombinantly produced peptide sequences are well known in the art and include, for example, gel filtration, affinity chromatography and ion exchange chromatography.

To facilitate isolation of a synthetic or recombinant peptide sequence, a fusion polypeptide may be made wherein the at least one peptide sequence is translationally fused (covalently linked) to a heterologous polypeptide which enables isolation by affinity chromatography. Typical heterologous polypeptides are His-Tag (e.g. His$_6$, 6 histidine residues), GST-Tag (Glutathione-S-transferase) etc. The fusion polypeptide facilitates not only the purification of the mimotopes but can also prevent the polypeptide from being degraded during purification. If it is desired to remove the heterologous polypeptide after purification the fusion polypeptide may comprise a cleavage site at the junction between the peptide sequence and the heterologous polypeptide. The cleavage site consists of an amino acid sequence that is cleaved with an enzyme specific for the amino acid sequence at the site (e.g. proteases).

The peptide sequences disclosed herein may be suitably modified at or nearby their N- and/or C-termini so that at said positions a cysteine residue is bound thereto.

For preparing peptide sequences, phage libraries and/or peptide libraries are also suitable, for instance, produced by means of combinatorial chemistry or obtained by means of high throughput screening techniques for the most varying structures (see, for example, *Display: A Laboratory Manual* by Carlos F. Barbas (Editor), et al.; and Willats W G *Phage display: practicalities and prospects. Plant Mol. Biol.* 2002 December; 50(6):837-54).

Where the immunogen comprises two or more peptide sequences, the peptide sequences may be presented as a fusion protein. As used herein, the term "fusion protein" typically refers to a polypeptide composed of two or more peptide sequences linked to one another. In an embodiment, the fusion protein comprises is a non-native polypeptide sequence of two or more peptide sequences linked to one another. Suitable methods of linking peptide sequences will be familiar to persons skilled in the art, illustrative examples of which include peptide (amide) bonds and linkers.

The immunogens disclosed herein may suitably comprise a fusion protein comprising, consisting, or consisting essentially of any combination of two or more PD1 B cell epitopes and/or mimotopes thereof, as herein described. In an embodiment, the fusion protein comprises, consists, or consists essentially of at least two B cell epitopes of PD1, or functional variants thereof, as herein described. In another embodiment, the fusion protein comprises, consists, or consists essentially of at least two non-contiguous B cell epitopes of PD1, or functional variants thereof, as herein described. In another embodiment disclosed herein, the fusion protein comprises, consists, or consists essentially of at least three non-contiguous B cell epitopes of PD1, or functional variants thereof, as herein described.

In another embodiment, the fusion protein comprises, consists, or consists essentially of at least two mimotopes of B cell epitopes of PD1, as herein described. In another embodiment, the fusion protein comprises, consists, or consists essentially of at least three mimotopes of B cell epitopes of PD1, as herein described.

Also contemplated herein are immunogens comprising a fusion protein comprising, consisting of, or consisting essentially of at least one (e.g., 1, 2, 3, 4, 5, 6 or more) PD1 B cell epitope, or a functional variant thereof, as herein described, and at least one mimotope (e.g., 1, 2, 3, 4, 5, 6 or more) of a PD1 B cell epitope, as herein described. In an embodiment disclosed herein, the fusion protein comprises one B cell epitope of PD1, or a functional variant thereof, as herein described, and one mimotope of a PD1 B cell epitope, as herein described. In another embodiment, the fusion protein comprises two B cell epitopes of PD1, or functional variants thereof, as herein described, and one mimotope of a PD1 B cell epitope, as herein described. In another embodiment, the fusion protein comprises one B cell epitope of PD1, or a functional variant thereof, as herein described, and two mimotopes of a PD1 B cell epitope, as herein described. In another embodiment disclosed herein, the fusion protein comprises two B cell epitope of PD1, or a functional variant thereof, as herein described, and two mimotopes of a PD1 B cell epitope, as herein described. In another embodiment, the fusion protein comprises three B cell epitopes of PD1, or functional variants thereof, as herein described, and two mimotopes of a PD1 B cell epitope, as herein described. In another embodiment, the fusion protein comprises three B cell epitopes of PD1, or functional variants thereof, as herein described, and two mimotopes of a PD1 B cell epitope, as herein described.

Also disclosed herein are immunogens comprising a fusion protein comprising, consisting or consisting essentially of at least two mimotopes (e.g., at least 2, preferably at least 3, preferably at least 4, preferably at least 5, preferably at least 6, preferably at least 7, preferably at least 8, preferably at least 9, more preferably at least 10 mimotopes) of one or more PD1 B cell epitope.

It is to be understood that, where the fusion protein comprises more than one mimotope, the mimotopes may raise an antibody response in which the antibodies bind the same B cell epitope of PD1, or they may bind different B cell epitopes of PD1. Thus, in an embodiment, the fusion protein comprises at least two mimotopes capable of inducing an antibody response in vivo in which the antibodies bind at least two PD1 B cell epitopes (e.g., at least 2, preferably at least 3, preferably at least 4, preferably at least 5, preferably at least 6, preferably at least 7, preferably at least 8, preferably at least 9, preferably at least 10 or more PD1 B cell epitopes).

Also contemplated herein are fusion proteins comprising at least two peptide sequences, as herein described, concatenated two or more times in tandem repeat. For example, fusion proteins contemplated herein may comprise two or more tandem repeats of the peptide fragments listed in Tables 1 and 2 (i.e., SEQ ID NOs:2-109 or functional variants thereof).

Without being bound by theory or by a particular mode of application, it will be understood that incorporating two or more different B cell epitopes and/or mimotopes into the fusion peptide, as herein described, may generate a more beneficial immune response by eliciting a higher antibody titre as compared to an immunogen comprising a single B cell epitope of PD1 or a mimotope thereof.

Where the at least two peptide sequences comprise amino acid sequences found in nature (e.g., sequences derived from a B cell epitope of native PD1), the peptide sequences may be linked to one another within the fusion peptide in such a way as to ensure the fusion protein comprises an amino acid sequence that is not identical to a continuous stretch of at least 40 amino acid residues of native PD1. For example, where the at least two peptide sequences are B cell epitopes of human PD1 (e.g., SEQ ID NO:1), the fusion protein comprises a least two non-contiguous B cell epitopes of human PD1. Thus, where the fusion protein comprises at least two B cell epitopes of PD1 (e.g, 2, 3, 4, 5, 6, 7, 8, 9, 10, 11 or more non-contiguous B cell epitopes of PD1), the fusion protein may comprise at least two non-contiguous B cell epitopes of PD1 linked to one another, such that the at least two B cell epitopes of PD1 are non-contiguous in their native state; that is, in native PD1.

Carrier

The peptide sequence(s) of the immunogen, as herein described, may suitably be conjugated, coupled or otherwise attached to a carrier. Thus, in another embodiment disclosed herein, the immunogen comprises a carrier.

In an embodiment, the carrier is immunogenic. As used herein, the term "immunogenic" typically means that the carrier is capable of facilitating or enhancing a humoral immune response to the peptide sequence(s) to which it is conjugated, coupled or otherwise attached when compared to the absence of a carrier.

Suitable carriers will be known to persons skilled in the art, illustrative examples of which include keyhole limpet hemocyanin (KLH), tetanus toxoid (TT), B subunit of cholera toxin (CT, CTB), heat labile toxin (LT) of *E. coli* and mutants thereof, lactic acid bacteria (LAB)/probiotic bacteria, bacterial ghost, a parasite-derived antigen such as an antigen from Toxoplasma gondii (see, for example, Wagner et al. *Sci Rep.* (2017); 7(1):15211, and Wagner et al., *PLoS One.* (2016); 11(5):e0155081, the contents of which are incorporated herein by reference in their entirety), liposome, virus-like particles, chitosome, virosome, toll-like receptor agonists, lipid A, bacterial DNA (CpG), ISCOM, cytokines (GM-CSF), polymeric, inorganic micro- and nano-particles, and diphtheria toxin variant CRM-197. In an embodiment disclosed herein, the carrier is selected from the group consisting of keyhole limpet hemocyanin (KLH), tetanus toxoid (TT), B subunit of cholera toxin (CT, CTB), heat labile toxin (LT) of *E. coli* and mutants thereof, lactic acid bacteria (LAB)/probiotic bacteria, bacterial ghost, a parasite-derived antigen, liposome, chitosome, virosome, a virus-like particle, and diphtheria toxin variant CRM-197. In an embodiment, the carrier is not a virus-like particle. In an embodiment, the vaccine composition does not comprise a virus-like particle.

In an embodiment, the carrier is diphtheria toxin variant CRM-197 (SEQ ID NO:118). CRM-197 (GenBank Accession No. 1007216A; SEQ ID NO:118) is an enzymatically inactive and nontoxic form of diphtheria toxin that contains a single amino acid substitution (Gly-Glu) at amino acid residue 52. A single GCA mutation that leads to the Glu52 substitution distinguishes CRM-197 from its wild-type species. The absence of toxicity of CRM-197 appears to be due to the loss of enzymatic activity of its fragment A, which in the wild-type species catalyzes the chemical modification of elongation factor 2 (translocase) in infected cells that is essential for protein synthesis. This non-toxic property makes CRM-197 a suitable carrier protein for the preparation of conjugated vaccines.

```
(CRM-197; GenBank Accession No. 1007216A)
                                     SEQ ID NO: 118
GADDVVDSSKSFVMENFSSYHGTKPGYVDSIQKGIQKPKSGTQGNYDDD

WKEFYSTDNKYDAAGYSVDNENPLSGKAGGVVKVTYPGLTKVLALKVDN

AETIKKELGLSLTEPLMEQVGTEEFIKRFGDGASRVVLSLPFAEGSSSV

EYINNWEQAKALSVELEINFETRGKRGQDAMYEYMAQACAGNRVRRSVG

SSLSCINLDWDVIRDKTKTKIESLKEHGPIKNKMSESPNKTVSEEKAKQ

YLEEFHQTALEHPELSELKTVTGTNPVFAGANYAAWAVNVAQVIDSETA

DNLEKTTAALSILPGIGSVMGIADGAVHHNTEEIVAQSIALSSLMVAQA

IPLVGELVDIGFAAYNFVESIINLFQVVHNSYNRPAYSPGHKTQPFLHD

GYAVSWNTVEDSIIRTGFQGESGHDIKITAENTPLPIAGVLLPTIPGKL

DVNKSKTHISVNGRKIRMRCRAIDGDVTFCRPKSPVYVGNGVHANLHVA

FHRSSSEKIHSNEISSDSIGVLGYQKTVDHTKVNSKLSLFFEIKS
```

Methods by which the peptide sequences or fusion proteins, as disclosed herein, can be conjugated, coupled or otherwise attached to a carrier such as CRM-197 will be known to persons skilled in the art. Illustrative examples include those described by Chang et al. (1998, *FEBS Letters*, 427:362-366) and Berti et al. (2004, *Biophysical Journal*, 86:3-9).

Conjugation of the peptide sequence(s), as disclosed herein, to a carrier is typically achieved through activation of the lysyl residues using suitable crosslinkers. For instance, since CRM-197 contains 40 lysines residues, and many of them are available for crosslinking, the end products of CRM-197 conjugation are invariably heterogeneous. Without being bound by theory or a particular mod of action, it is generally understood that the ratio of the peptide sequence(s) to the carrier depends on the size or molecular weight of the peptide sequence(s). For instance, where the peptide sequence(s) is(are) relatively small (e.g., about 75 amino acids in length), it may be possible to produce a carrier that is conjugated with 20-39 peptide sequences. Conversely, for larger peptide sequence(s), the carrier may be conjugated with up to, or fewer than, 20 peptide sequences. In an embodiment described herein, the immunogen comprises from 2 to 39 peptide sequences conjugated, coupled or otherwise attached to the carrier. In another embodiment, the immunogen comprises at least 20 peptide sequences conjugated, coupled or otherwise attached to the carrier. In yet another embodiment, the immunogen comprises from 6 to 12 peptide sequences conjugated, coupled or otherwise attached to the carrier.

The peptide sequence(s) of the immunogen can be conjugated, coupled or otherwise attached to the carrier by a covalent bond. However, in some embodiments, the peptide sequence(s) may be coupled to the carrier by a non-covalent association. Where the peptide sequence(s) is(are) non-covalently associated with the carrier, the non-covalent association will typically involve an electromagnetic interaction between one or more atoms of the peptide sequence(s) with one or more atoms of the carrier. Illustrative examples include ionic bonding (i.e., the attraction formed between two oppositely charged ions by virtue of this opposite charge), Van der Weals forces (i.e., forces between permanent and/or induced dipoles of existing covalent bonds within the fusion protein and the carrier) and/or hydrophobic interactions (i.e., forces resulting from the tendency of hydrophobic/aliphatic portions within the peptide sequence(s) or fusion protein(s), as herein described, to associate with hydrophobic portions of the carrier).

In an embodiment disclosed herein, the peptide epitope is conjugated to a carrier.

It will be understood by persons skilled in the art that, where coupling of the a peptide epitope to the carrier protein is via a linker, it is preferable to effect such linker-mediated coupling from the C-terminus of the peptide epitope, since linker coupling from the N-terminus may, in some instances, have a negative influence on the desired immune response to be elicited.

In an embodiment disclosed herein, the carrier is immunogenic.

In an embodiment disclosed herein, the carrier is selected from the group consisting of keyhole limpet hemocyanin (KLH), tetanus toxoid (TT), B subunit of cholera toxin (CT, CTB), heat labile toxin (LT) of *E. coli* and mutants thereof, lactic acid bacteria (LAB), bacterial ghost, liposome, chitosome, virosome, virus-like particle, dendritic cell and diphtheria toxin variant CRM-197. In an embodiment, the carrier is not a virus-like particle. In an embodiment, the vaccine composition does not comprise a virus-like particle.

In an embodiment disclosed herein, the carrier is diphtheria toxin variant CRM-197 (SEQ ID NO:58).

CRM-197 (GenBank Accession No. 1007216A; SEQ ID NO:58) is an enzymatically inactive and nontoxic form of diphtheria toxin that contains a single amino acid substitution (Gly-Glu) at amino acid residue 52. A single GCA mutation that leads to the Glu52 substitution distinguishes CRM-197 from its wild-type species. The absence of toxicity of CRM-197 appears to be due to the loss of enzymatic activity of its fragment A, which in the wild-type species catalyzes the chemical modification of elongation factor 2 (translocase) in infected cells that is essential for protein synthesis. This non-toxic property makes CRM-197 a suitable carrier protein for the preparation of conjugated vaccines.

(CRM-197; GenBank Accession No. 1007216A)
SEQ ID NO: 58
GADDVVDSSKSFVMENFSSYHGTKPGYVDSIQKGIQKPKSGTQGNYDDD

WKEFYSTDNKYDAAGYSVDNENPLSGKAGGVVKVTYPGLTKVLALKVDN

AETIKKELGLSLTEPLMEQVGTEEFIKRFGDGASRVVLSLPFAEGSSSV

EYINNWEQAKALSVELEINFETRGKRGQDAMYEYMAQACAGNRVRRSVG

SSLSCINLDWDVIRDKTKTKIESLKEHGPIKNKMSESPNKTVSEEKAKQ

YLEEFHQTALEHPELSELKTVTGTNPVFAGANYAAWAVNVAQVIDSETA

DNLEKTTAALSILPGIGSVMGIADGAVHHNTEEIVAQSIALSSLMVAQA

IPLVGELVDIGFAAYNFVESIINLFQVVHNSYNRPAYSPGHKTQPFLHD

GYAVSWNTVEDSIIRTGFQGESGHDIKITAENTPLPIAGVLLPTIPGKL

DVNKSKTHISVNGRKIRMRCRAIDGDVTFCRPKSPVYVGNGVHANLHVA

FHRSSSEKIHSNEISSDSIGVLGYQKTVDHTKVNSKLSLFFEIKS

Methods by which a peptide epitope can be conjugated, coupled or otherwise attached to CRM-197 are known to persons skilled in the art. Illustrative examples include those described by Chang et al. (1998, *FEBS Letters*, 427:362-366) and Berti et al. (2004, *Biophysical Journal*, 86:3-9).

Conjugation of a peptide epitope, as herein described, to CRM-197 is typically achieved through activation of the lysyl residues using suitable crosslinkers. Since CRM-197 contains 40 lysines residues, and many of them are available for crosslinking, the end products of CRM-197 conjugation are invariably heterogeneous. Without being bound by theory or a particular mod of action, it is generally understood that the ratio of the immunogen to carrier protein depends on the size or molecular weight of the immunogen. For instance, where the immunogen is relatively small (e.g., 12-24 amino acids in length), it may be possible to produce a carrier that is conjugated with 20-39 immunogens. Conversely, for a larger immunogens, the carrier may be conjugated with up to, or fewer than, 20 immunogens. In an embodiment described herein, the carrier comprises from 2 to 39 immunogens. In another embodiment, the carrier comprises at least 20 immunogens. In yet another embodiment, the carrier comprises from 6 to 12 immunogens.

The immunogen can be coupled to the carrier by a covalent bond. However, in some embodiments, the immunogen may be coupled to the carrier by a non-covalent association. Where the immunogen is non-covalently associated with the carrier, the non-covalent association will typically involve an electromagnetic interaction between one or more atoms of the immunogen with one or more atoms of the carrier. Illustrative examples include ionic bonding (i.e., the attraction formed between two oppositely charged ions by virtue of this opposite charge), Van der Weals forces (i.e., forces between permanent and/or induced dipoles of existing covalent bonds within the peptide epitope and the carrier) and/or hydrophobic interactions (i.e., forces resulting from the tendency of hydrophobic/aliphatic portions within the peptide epitope (s), as herein described, to associate with hydrophobic portions of the carrier).

Adjuvant

The vaccine composition disclosed herein may suitably be formulated with an adjuvant to further enhance the antibody response to PD1. Thus, in an embodiment, the vaccine composition disclosed herein comprises an adjuvant.

As used herein, the term "adjuvant" typically refers to a class of substance that can increase the magnitude of the immune (antibody) response elicited by the immunogen beyond that which would be expected from the immunogen alone.

Suitable adjuvants will be known to persons skilled in the art, illustrative examples of which include aluminium salts (e.g. aluminium hydroxide, aluminium phosphate and potassium aluminium sulfate (also referred to as Alum)), liposomes, virosomes, water-in-oil or oil-in-water emulsions (e.g. Freund's incomplete adjuvant, Montanide®, MF59® and AS03), 3-O-desacyl-4'-monophosphoryl lipid A (MPL) and adjuvants containing MPL (e.g. AS01, AS02 and AS04), toll-like receptor agonists (see, e.g., Kaczanowska et al., 2013, *J. Leukoc. Biol.* 93(6):847-863; the entire contents of which are incorporated herein by reference), squalene and saponin-based adjuvants. Saponin-based adjuvants include saponins or saponin derivatives from, for example, *Quillaja saponaria, Panax ginseng Panax notoginseng, Panax quinquefolium, Platycodon grandiflorum, Polygala senega, Polygala tenuifolia, Quillaja brasiliensis, Astragalus membranaceus* and *Achyranthes bidentata*. Exemplary saponin-based adjuvants include iscoms, iscom matrix, ISCOMATRIX™ adjuvant, Matrix M™ adjuvant, Matrix C™ adjuvant, Matrix Q™ adjuvant, AbISCO®-100 adjuvant, AbISCO®-300 adjuvant, ISCOPREP™, an ISCOPREP™ derivative, adjuvant containing ISCOPREP™ or an ISCOPREP™ derivative, QS-21, a QS-21 derivative, and an adjuvant containing QS-21 or a QS21 derivative.

Other suitable adjuvants include cytokines, chemokines and growth factors, illustrative examples of which include GM-CSF, interleukins (e.g., IL-1, IL-2, IL-5, IL-7, IL-8, IL-10, IL-12, IL-15, IL-18 and IL-21), tumour necrosis factor (TNF), interferon (e.g., IFN-γ), transforming growth factor (e.g., TGF-β), RANTES, MIP1-α, MCP-1, heat-shock proteins (e.g., HSP70), C-type lectin receptor agonists (e.g., Mincle, Dectin-1, Dectin-2 and CLEC9A) and retinoic acid-inducible gene I (RIG-1)-like receptor ligands (e.g., RIG-I and melanoma differentiation-associated gene 5 (MDA5)) and Toll-like receptor ligands or agonists. Suitable Toll-like receptor ligands will be familiar to persons skilled in the art, illustrative examples of which include monophosphoryl lipid A (3-O-desacyl-4'-monophosphoryl lipid A; MPL), bacterial lipoprotein, $Pam_3CSK_4$, Poly J:C, Poly ICLC, glucopyranosyl lipid A-stable emulsions, and CpG ODN. Other examples of Toll-like receptor ligands are disclosed in Steinhagen et al. (2011, *Vaccine*, 29(17):3341-3355), the entire contents of which are incorporated herein by reference.

In an embodiment disclosed herein, the adjuvant is selected from the group consisting of aluminium hydroxide, aluminium phosphate, potassium aluminium sulfate, calcium phosphate hydroxide, a saponin, a TLR agonist, CRM197, a water-in-oil emulsion, an oil-in-water emulsion, Freund's incomplete adjuvant, MF59, a CpG oligonucleotide, iscoms, iscom matrix, monophosphoryl lipid A ((3-O-desacyl-4'-monophosphoryl lipid A; MPL), AS01 (a liposome-based formulation of MPL and QS-21), AS04 (a liposome-based formulation of MPL and aluminium hydroxide), QS-21, a QS-21 derivative, an adjuvant containing QS-21 or a QS21 derivative, and a combination of any of the foregoing.

In an embodiment disclosed herein, the adjuvant is a TLR-4 agonist. In an embodiment disclosed herein, the TLR-4 agonist is monophosphoryl lipid A. In an embodiment disclosed herein, the adjuvant is Montanide. In an embodiment disclosed herein, the TLR-4 agonist is AS01 (a liposome-based formulation of MPL and QS-21). In an embodiment disclosed herein, the adjuvant is AS04 (a liposome-based formulation of MPL and aluminium hydroxide). In another embodiment disclosed herein, the adjuvant is selected from the group consisting of aluminium hydroxide, aluminium phosphate and potassium aluminium sulfate.

Mixtures of two or more adjuvants within the same vaccine composition are also contemplated herein. The present disclosure also extends to the use of a combination of adjuvants and/or carriers.

In an embodiment disclosed herein, the composition further comprises an adjuvant.

As used herein, the term "adjuvant" typically refers to a class of substance that can increase the magnitude of the immune response elicited by the immunogen beyond that which would be expected, either from the immunogen alone or from the immunogen-carrier conjugate, as herein described, in the absence of an adjuvant.

Suitable adjuvants will be known to persons skilled in the art. Non-limiting examples of suitable adjuvants include aluminium salts (e.g. aluminium hydroxide, aluminium phosphate and potassium aluminium sulfate (also referred to as Alum)), liposomes, virosomes, water-in-oil or oil-in-water emulsions (e.g. Freund's adjuvant, Montanide®, MF59® and AS03), 3-O-desacyl-4'-monophosphoryl lipid A (MPL) and adjuvants containing MPL (e.g. AS01, AS02 and AS04) and saponin-based adjuvants. Saponin-based adjuvants include saponins or saponin derivatives from, for example, *Quillaja saponaria, Panax ginseng Panax notoginseng, Panax quinquefolium, Platycodon grandiflorum, Polygala senega, Polygala tenuifolia, Quillaja brasiliensis, Astragalus membranaceus* and *Achyranthes bidentata*. Exemplary saponin-based adjuvants include iscoms, iscom matrix, ISCOMATRIX™ adjuvant, Matrix M™ adjuvant, Matrix C™ adjuvant, Matrix Q™ adjuvant, AbISCO®-100 adjuvant, AbISCO®-300 adjuvant, ISCOPREP™, an ISCOPREP™ derivative, adjuvant containing ISCOPREP™ or an ISCOPREP™ derivative, QS-21, a QS-21 derivative, and an adjuvant containing QS-21 or a QS21 derivative. The vaccine composition as herein described can also be associated with immunomodulatory agents, including, for example, cytokines, chemokines and growth factors. Mixtures of two or more adjuvants within the same vaccine composition are also contemplated herein.

In an embodiment disclosed herein, the adjuvant is selected from the group consisting of aluminium hydroxide, aluminium phosphate, potassium aluminium sulfate, calcium phosphate hydroxide, a saponin, Freund's complete adjuvant, a TLR agonist, CRM197, Montanide®, Freund's incomplete adjuvant, MF59, a CpG oligonucleotide, iscoms, iscom matrix, ISCOMATRIX™ adjuvant, Matrix M™ adjuvant, Matrix C™ adjuvant, Matrix Q™ adjuvant, AbISCO®-100 adjuvant, AbISCO®-300 adjuvant, ISCOPREP™, an ISCOPREP™ derivative, adjuvant containing ISCOPREP™ or an ISCOPREP™ derivative, monophosphoryl lipid A ((3-O-desacyl-4'-monophosphoryl lipid A; MPL), AS01 (a liposome-based formulation of MPL and QS-21), AS04 (a liposome-based formulation of MPL and aluminium hydroxide), QS-21, a QS-21 derivative, an adjuvant containing QS-21 or a QS21 derivative, and a combination of any of the foregoing.

In an embodiment disclosed herein, the adjuvant is a TLR-4 agonist. In an embodiment disclosed herein, the TLR-4 agonist is monophosphoryl lipid A. In an embodiment disclosed herein, the adjuvant is Montanide. In an embodiment disclosed herein, the TLR-4 agonist is AS01 (a liposome-based formulation of MPL and QS-21). In an embodiment disclosed herein, the adjuvant is AS04 (a liposome-based formulation of MPL and aluminium hydroxide).

The present disclosure also extends to the use of a combination of adjuvants and/or carriers.

Treatment of Cancer

As noted elsewhere herein, the present inventors have surprisingly found that immunization with a peptide sequence of a B cell epitope of the checkpoint antigen PD1 is capable of raising an antibody response in which the antibodies bind to the native PD1 protein. It was also surprisingly found that immunization with the PD1-derived B cell epitope did not appear to give rise to adverse side effects that are sometimes evident with the passive administration of antibodies to checkpoint antigens. Thus, disclosed herein is a method of treating a cancer characterised by an involvement of programmed cell death protein 1 (PD1), the method comprising administering to a subject a vaccine composition for raising a humoral response to PD1, wherein the vaccine composition comprises an effective amount of an immunogen that induces an antibody response in which the antibody binds to a B cell epitope of PD1.

The terms "cancer" and "tumour" are used interchangeably herein and will be understood as comprising malignant cells; also referred to as neoplastic cells, cancer cells or tumour cells. By "malignant cell" is meant an abnormal cell that grows by uncontrolled cellular proliferation and will typically continues to grow after the initial growth stimulus has ceased.

By "cancer characterised by an involvement of PD1" is meant a cancer in which PD1 is involved, at least in part, in an endogenous inhibitory pathway responsible for down-regulating the immune response towards the cancer.

Persons skilled in the art will be familiar with the type of cancers that are characterised by an involvement of PD1. Illustrative examples include malignancies such as melanoma, non-small cell lung cancer, renal cell carcinoma, bladder cancer, Hodgkin's lymphoma, gastric cancer, pancreatic cancer, prostate cancer and salivary gland cancer. In an embodiment, the cancer is non-small cell lung cancer. In another embodiment, the cancer is melanoma. In another embodiment, the cancer is gastric cancer. As noted elsewhere herein, the methods described herein are directed to vaccine compositions for the treatment of a cancer characterised by an involvement of PD1. Other illustrative examples include leukemias, seminomas, teratomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer, and lung cancer, lung carcinomas, prostate carcinomas, colon carcinomas, cervical carcinomas and the metastases thereof.

In some embodiments, the cancer is characterized by the presence of malignant cells in which a cancer-associated antigen, as described elsewhere herein, is expressed or aberrantly expressed (e.g., overexpressed) by the malignant cells or tissue. Preferably, the cancer is characterized by surface expression of the cancer-associated antigen. By "aberrant" or "abnormal" expression is meant that expression of the cancer-associated antigen is altered, preferably increased, compared to the state in a non-malignant or normal cell or in a healthy individual (i.e., in an individual not having a disease associated with aberrant or abnormal expression of the antigen). In some embodiments, the increase in expression of the cancer-associated antigen refers to an increase by at least 10%, preferably by at least 20%, preferably by at least 50%, preferably by at least 100%, or more. In some embodiment, aberrant or abnormal expression of the cancer-associated antigen means that the antigen is only detectable on the cancer cells or tissue, while expression in normal or healthy tissue is undetectable.

The vaccine composition, as described herein, is formulated for administration to a subject in need thereof to provide the immunogen in an "effective amount"; that is, an amount effective to elicit any one or more inter alia of a therapeutic effect. Persons skilled in the art would be able, by routine experimentation, to determine an effective, non-toxic amount to administer for the desired outcome. In general, the vaccine composition, as disclosed herein, can be administered in a manner compatible with the route of administration and physical characteristics of the recipient (including health status) and in such a way that it elicits the desired effect(s) (i.e. therapeutic effect). For example, the appropriate dosage of a composition may depend on a variety of factors including, but not limited to, a subject's physical characteristics (e.g., age, weight, sex), whether the composition is being used as single agent or as part of adjunct therapy (e.g., with a second immunogen directed to a cancer-associated antigen, as described elsewhere herein), the progression (i.e., pathological state) of any underlying cancer, and other factors that may be recognized by persons skilled in the art. Other illustrative examples of general considerations that may be considered when determining, for example, an appropriate dosage of the compositions are discussed by Gennaro (2000, "Remington: The Science and Practice of Pharmacy", 20th edition, Lippincott, Williams, & Wilkins; and Gilman et al., (Eds), (1990), "Goodman And Gilman's: The Pharmacological Bases of Therapeutics", Pergamon Press).

It is expected that the effective amount will fall in a relatively broad range that can be determined through methods known to persons skilled in the art, having regard to some of the considerations outlined above.

An effective amount of the immunogen to be administered will generally be in a range of from about 5 µg to about 1.0 mg of immunogen per subject, from about 10 µg to about 500 µg of immunogen per subject, or from about 15 µg to about 60 µg of immunogen per subject. An effective amount can be ascertained, for example, by standard methods involving measurement of antigen-specific antibody titres. The level of immunity provided by the compositions herein described can be monitored to determine the need, if any, for boosters. For instance, following an assessment of an antigen-specific antibody titre in the serum, typically days or weeks following the first administration of the composition in a subject, optional booster immunisations may be required and/or desired.

It will be apparent to persons skilled in the art that the optimal quantity and spacing of individual dosages, if required to induce the desired immune response, can be determined, for example, by the form, route and site of administration, and the nature of the particular subject to be treated, as is described elsewhere herein. Optimum conditions can be determined using conventional techniques known to persons skilled in the art. In some instances, it may be desirable to have several or multiple administrations of the vaccine and/or pharmaceutical compositions, as herein described. For example, the compositions may be administered 1, 2, 3, 4, 5, 6, 7, 8, 9, 10, or more times. The administrations may be from about one day intervals to about twelve week intervals, and in certain embodiments from about one to about four week intervals. Periodic re-administration may be required to achieve a desirable therapeutic result, such as a reduction in tumour size and/or a reduction in the occurrence of metastases. It will also be apparent to persons skilled in the art that the optimal course of administration can be ascertained using conventional course of treatment or efficacy or immune status determination tests.

It will be understood that "inducing" an immune or antigen-specific antibody response, as contemplated herein, includes eliciting or stimulating an immune response and/or enhancing a previously existing immune response to obtaining a desired therapeutic effect, such as a reduction in tumour size, a slowing of tumour growth and/or a reduction in the occurrence of metastases. The effect can also be prophylactic in terms of, for example, completely or partially preventing the occurrence of metastases.

As used herein, the terms "administration" or "administering" typically refer to the step of introducing the vaccine and/or pharmaceutical compositions, as herein described, into a patient's body so that the patient's immune system mounts a response to the peptide sequences within the fusion protein. As used herein, a "subject in need thereof" includes an individual who has been diagnosed with cancer. In its broadest sense, the term "a patient in need thereof" therefore encompasses individuals with an already present need, as well as individuals who are at risk of developing cancer.

The terms "treating", "treatment" and the like, are also used interchangeably herein to mean relieving, reducing, alleviating, ameliorating or otherwise inhibiting the progression of cancer in a subject, including one or more symptoms thereof. The terms "treating", "treatment" and the like are also used interchangeably herein to mean preventing cancer from occurring or delaying the onset or subsequent progression of cancer in a subject that may be predisposed to, or at risk of, cancer, but has not yet been diagnosed as having it. In that context, the terms "treating", "treatment" and the like are used interchangeably with terms such as "prophylaxis", "prophylactic" and "preventive". As used herein, a medicament which "treats" cancer will ideally eliminate the disease altogether by eliminating its underlying cause so that, upon cessation of administration of the composition, the disease does not re-develop, but remains in remission. As used herein, a medicament which "ameliorates" cancer does not eliminate the underlying cause of the disease, but reduces the severity of the disease as measured by any established grading system and/or as measured by an improvement in the patient's well-being, e.g. decrease in pain and/or discomfort.

Also contemplated herein are adjunct therapies for treating cancer by using one or more additional therapeutic agents. Without being bound by theory or by a particular mode of application, it will generally be understood that the use of a second immunogen, as herein described, can provide an enhance immune response for the treatment of a cancer in the subject. In an embodiment, the methods disclosed herein further comprise administering to the subject a second immunogen in an effective amount to induce an immune response against a checkpoint antigen other than PD1. In an embodiment, the methods disclosed herein further comprise administering to the subject a second immunogen in an effective amount to induce an immune response against a cancer-associated antigen.

The immune response induced by the second immunogen may suitably comprise a T cell response (e.g., CTL), a B cell response, or both. For example, the second immunogen may comprise at least one B cell epitope of a checkpoint antigen other than PD1 and/or of a cancer-associated antigen (and/or mimotopes thereof), such that when administered to the subject in an effective amount, is capable of inducing an antibody (B cell) response against the checkpoint antigen and/or the cancer-associated antigen. In an embodiment, the second immunogen is administered to the subject in an effective amount to induce an antibody (B cell) response. In an embodiment, the second immunogen is administered to the subject in an effective amount to induce an antibody response in which the antibody binds to a B cell epitope of a cancer-associated antigen. In another embodiment, the second immunogen is administered to the subject in an effective amount to induce an antibody response in which the antibody binds to a B cell epitope of a checkpoint antigen other than PD1. In an embodiment, the second immunogen comprises at least one B cell epitope of a checkpoint antigen other than PD1 and/or of a cancer-associated antigen. In another embodiment, the second immunogen comprises a mimotope that is capable of inducing an antibody response in which the antibody binds to a B cell epitope of a checkpoint antigen other than PD1 and/or of a cancer-associated antigen.

Alternatively, or in addition, the second immunogen may comprise at least one T cell epitope of a checkpoint antigen other than PD1 and/or of a cancer-associated antigen, such that when administered to the subject in an effective amount, is capable of inducing a T cell (e.g., CTL) response against the checkpoint antigen and/or the cancer-associated antigen. Thus, in an embodiment, the second immunogen is administered to the subject in an effective amount to induce a T cell response against checkpoint antigen other than PD1. In another embodiment, the second immunogen is administered to the subject in an effective amount to induce a T cell response against a cancer-associated antigen. In an embodiment, the second immunogen comprises at least one T cell epitope of a cancer-associated antigen. In another embodiment, the second immunogen comprises at least one T cell epitope of a checkpoint antigen other than PD1.

In other embodiments, the second immunogen comprises at least one B cell epitope of a cancer-associated antigen, or a mimotope thereof, and at least one T cell epitope of a cancer-associated antigen, such that when administered to the subject in an effective amount, is capable of inducing an antibody response and a T cell response against the cancer-associated antigen. The at least one T cell epitope and the at least one B cell epitope, or mimotope thereof, may suitably be derived from the same cancer-associated antigen, such that when the second immunogen is administered to the subject in an effective amount, it is capable of inducing an antibody response and a T cell response against the same cancer-associated antigen. Alternatively, or in addition, the at least one T cell epitope and the at least one B cell epitope, or mimotope thereof, may suitably be derived from different cancer-associated antigens, such that when the second immunogen is administered to the subject in an effective amount, it is capable of inducing an antibody response and a T cell response against each of the different cancer-associated antigens.

Suitable checkpoint antigens other than PD1 will be familiar to persons skilled in the art, illustrative examples of which are discussed by Pardoll (2012, *Nature Reviews Cancer* 12:252-64). Other illustrative examples of suitable checkpoint antigens include CTLA-4 (cytotoxic T lymphocyte antigen-4) and its ligands CD80 and CD86; PD-L1 (programmed cell death ligand 1), PD-L2 (programmed cell death ligand 2), LAG-3 (lymphocyte activation gene-3) and its ligand MHC class I or II, TIM-3 (T cell immunoglobulin and mucin protein-3) and its ligand GAL-9, B- and T-lymphocyte attenuator (BTLA) and its ligand herpes virus entry mediator (HVEM) and several others, as discussed, for example, by Nirschl & Drake (2013 *Clin Cancer Res* 19:4917-24). In an embodiment disclosed herein, the checkpoint antigen other than PD1 is selected from the group consisting of PD-L1, PD-L2, CTLA-4, LAG-3, OX40, OX40L, TIM-3 and GAL-9.

The term "checkpoint antigen" is understood to mean an antigen that is involved in endogenous inhibitory pathways for immune system function, such as those that act to maintain self-tolerance and modulate the duration and extent of immune response to antigenic stimulation.

The terms "cancer-associated antigen", "antigen associated with cancer, "tumour-associated antigen", "tumour antigen", "cancer antigen" and the like are used interchangeably herein to mean an antigen that is aberrantly expressed in cancer cells or tissue. In some embodiments, the antigen may be expressed under normal conditions in a limited number of tissues and/or organs or in specific developmental stages. For example, the antigen may be specifically expressed under normal conditions in stomach tissue and is expressed or aberrantly expressed (e.g., overexpressed) in one or more cancer cells. The expression of antigen may be reactivated in cancer cells or tissue irrespective of the origin of the cancer. In some embodiments, the cancer-associated antigen includes differentiation antigens, preferably cell type-specific differentiation antigens (i.e., proteins that are specifically expressed under normal conditions in a certain cell type at a certain differentiation stage), cancer/testis antigens (i.e., proteins that are specifically expressed under normal conditions in testis and sometimes in placenta), and germline specific antigens.

In an embodiment, the antigen associated with cancer is expressed on the cell surface of a cancer cell and is preferably not or only rarely expressed on normal cells and tissues. Preferably, the antigen or the aberrant expression of the antigen identifies cancer cells, preferably tumour cells. In some embodiments, the antigen that is expressed by a cancer cell in a subject (e.g., a patient suffering from cancer) is a self-protein. It will be understood, however, that no autoantibodies directed against the antigen are typically found in a detectable level under normal conditions in a subject carrying the antigen (typically a healthy patient that does not have cancer) or such autoantibodies can only be found in an amount below a threshold concentration that would be necessary to damage the tissue or cells carrying the antigen. Suitable cancer-associated antigens will be known to persons skilled in the art, illustrative examples of which include EGFR (e.g., Her2/neu, Her-1), BAGE (B melanoma antigen), CEA (carcinoembryonic antigen), Cpg (cytosine-phosphate diesterguanine), Gp100 (glycoprotein 100), h-TERT (telomerase transcriptase), MAGE (melanoma antigen-encoding gene), Melan-A (melanoma antigen recognized by T cells) and MUC-1 (mucin-1). Thus, in an embodiment, the cancer-associated antigen is selected from the group consisting of EGFR (e.g., Her2/neu, Her-1), BAGE (B melanoma antigen), CEA (carcinoembryonic antigen), CpG (cytosine-phosphate diesterguanine), Gp100 (glycoprotein 100), h-TERT (telomerase transcriptase), MAGE (melanoma antigen-encoding gene), Melan-A (melanoma antigen recognized by T cells) and MUC-1 (mucin-1). It will also be understood that the choice of antigen that is to be the target of the vaccine composition produced by the methods disclosed herein will typically depend on the intended use of the vaccine composition. For example, if the vaccine composition is intended to treat subjects with breast cancer, then the antigen will typically be an antigen that is associated with (e.g., overexpressed by) the breast cancer. Suitable examples of antigens associated with breast cancer will be familiar to persons skilled in the art, illustrative examples of which include the epidermal growth factor receptors Her2/neu and Her1.

In some embodiments, the amino acid sequence of the checkpoint antigen other than PD1 and/or the cancer-associated antigen is identical between the antigen as it is expressed in normal tissues and the antigen as it is expressed in cancer cells or tissue. In other embodiments, the amino acid sequence of the checkpoint antigen other than PD1 and/or the cancer-associated antigen comprises a mutation in its amino acid sequence when compared to the amino acid sequence of the native antigen as it would otherwise be expressed in normal tissue or cells.

It will also be understood that the ability of the second immunogen, as herein described, to improve the efficacy of the vaccine composition by raising an immune response to the checkpoint antigen other than PD1 and/or the cancer-associated antigen does not require the second immunogen to be present in the vaccine composition with the PD1-targeted immunogen, or to be administered simultaneously with the PD1-targeted immunogen to a subject in need thereof. Thus, the second immunogen, as herein described, can be administered prior, or subsequent, to the administration of the PD1-targeted immunogen, wherein the period of time between administering the PD1-targeted immunogen and administering the second immunogen can be optimised to provide the desired synergistic or additive effect.

The terms "normal tissue" or "normal conditions" typically refer to healthy tissue or the conditions in a healthy subject; that is, non-pathological conditions, wherein "healthy" preferably means non-tumorigenic or non-cancerous.

The term "specifically expressed" typically means that the antigen is only, or predominantly, expressed in a specific tissue or organ. For example, a antigen specifically expressed in breast tissue means that the antigen is primarily expressed in breast tissue and is not expressed in other tissues or is not expressed to a significant extent in other tissue or organs. Thus, an antigen that is exclusively expressed in cells of breast tissue and to a significantly lesser extent in any other tissue, such as the gastric mucosa, is specifically expressed in cells of breast tissue. In some embodiments, the antigen may also be specifically expressed under normal conditions in more than one tissue type or organ (e.g., 2, 3, 4, 5, 6 or more) tissue types or organs. For example, if an antigen associated with cancer is expressed under normal conditions to an approximately equal extent in breast and stomach tissue, the antigen is considered to be specifically expressed in breast and stomach tissue.

As used herein, the term "self protein" means a protein that is encoded by the genome of the subject and that is under normal conditions (i.e., non-pathological conditions) optionally expressed in certain normal tissue types or at certain stages of development.

Also contemplated herein are methods of treating a cancer characterised by an involvement of PD1 in which the vaccine composition disclosed herein is administered together (either simultaneously or sequentially) with one or more additional therapeutic agents that specifically target the cancer. Thus, in another embodiment, the method further comprises administering to the subject one or more additional therapeutic agents that specifically target a malignant cell.

In another embodiment, the vaccine compositions described herein further comprise one or more additional therapeutic agents or compounds that specifically target a malignant cell. Suitable additional therapeutic agents will be known to persons skilled in the art, illustrative examples of which include antibodies that specifically bind to a checkpoint antigen and/or a cancer-associated antigen, or an antigen-binding fragment thereof. Thus, in an embodiment, the methods disclosed herein further comprises administering to the subject an antibody that specifically binds to a cancer-associated antigen, or an antigen-binding fragment thereof, as described elsewhere herein. In yet another embodiment, the methods disclosed herein further comprise administering to the subject an antibody that specifically binds to a checkpoint antigen, or an antigen-binding fragment thereof, as described elsewhere herein. In an embodiment, the antibody or an antigen-binding fragment specifically binds to a checkpoint antigen other than PD1. Alternatively, or in addition, the antibody or an antigen-binding fragment specifically binds to PD1.

In another aspect of the present disclosure, there is provided use of a vaccine composition in the preparation of a medicament for the treatment of a cancer characterised by an involvement of PD1, wherein the vaccine composition comprises an effective amount of an immunogen for inducing an antibody response in which the antibody binds to a B cell epitope of PD1, as herein described.

In another aspect of the present disclosure, there is provided a vaccine composition for use in treating a cancer characterised by an involvement of PD1, wherein the vaccine composition comprises an effective amount of an immunogen for inducing an antibody response in which the antibody binds to a B cell epitope of PD1, as herein described.

In another aspect of the present disclosure, there is provided a vaccine composition for raising a humoral response to PD1, wherein the vaccine composition comprises an effective amount of an immunogen for inducing an antibody response in which the antibody binds to a B cell epitope of PD1, as herein described.

In an embodiment, the vaccine pharmaceutical compositions described herein comprise a pharmaceutically acceptable excipient. Suitable pharmaceutically acceptable excipients (e.g. carriers, diluents, etc.). will be known to persons skilled in the art. For example, a variety of aqueous (pharmaceutically acceptable) excipients may be used, such as buffered water, 0.4% saline, 0.3% glycine, hyaluronic acid and the like. These compositions may be sterilized by conventional, well known sterilization techniques or may be sterile-filtered. The resulting aqueous solutions may be packaged for use as is or lyophilized, the lyophilized preparation being combined with a sterile solution prior to administration. The compositions may further comprise pharmaceutically acceptable auxiliary substances as required to approximate physiological conditions, such as pH-adjusting and buffering agents, tonicity-adjusting agents, wetting agents and the like, for example sodium acetate, sodium lactate, sodium chloride, potassium chloride, calcium chloride, sorbitan monolaurate, triethanolamine oleate, sucrose or other carbohydrates, among many others. Suitable methods for preparing parenterally administrable compounds will be known or apparent to those skilled in the art and are described in more detail in, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7.sup.th ed., Lippincott, Williams, & Wilkins; and Handbook of Pharmaceutical Excipients (2000) A. H. Kibbe et al., eds., 3.sup.rd ed. Amer. Pharmaceutical Assoc.

The vaccine composition may be prepared in a form suitable for parenteral administration (e.g., subcutaneous, intramuscular or intravenous injection) or in an aerosol form suitable for administration by inhalation, such as by intranasal inhalation or oral inhalation.

The vaccine compositions described herein may also be provided in a kit. The kit may comprise additional components to assist in performing the methods as herein described, such as administration device(s), excipients(s), carrier(s) and/or diluent(s). The kits may include containers for housing the various components and instructions for using the kit components in such methods.

In an embodiment disclosed herein, the vaccine composition further comprises a second immunogen in an effective amount for inducing an immune response against a checkpoint antigen other than PD1 and/or a cancer-associated antigen, as described elsewhere herein.

In another embodiment, the vaccine composition further comprises an antibody that specifically binds to a checkpoint antigen and/or a cancer-associated antigen, or an antigen-binding fragment thereof, as described elsewhere herein.

In another embodiment, the vaccine composition further comprises one or more additional therapeutic agents that specifically target a malignant cell, as described elsewhere herein.

Cancer-Associated Antigens

With a view to improving the efficacy of the peptide epitope disclosed herein in the treatment of a condition characterised by an involvement of PD1, where that condition is cancer, the vaccine composition may further comprise at least one B cell epitope and/or mimotope of a cancer-associated antigen.

In an embodiment disclosed herein, the vaccine composition further comprises at least one B cell epitope and/or mimotope of a cancer-associated antigen such that the peptide epitope and the at least one B cell epitope and/or mimotope of a cancer-associated antigen are present in the same composition. It will be understood, however, that the ability of the at least one B cell epitope and/or mimotope of a cancer-associated antigen to improve the efficacy of the peptide epitope disclosed herein, by raising an antibody response to the cancer-associated antigen, does not require the at least one B cell epitope and/or mimotope of a cancer-associated antigen to be present in the vaccine composition with the peptide epitope or to be administered simultaneously to a subject in need thereof. Thus, in some embodiments, as described elsewhere herein, the at least one B cell epitope and/or mimotope of a cancer-associated antigen can be administered prior or subsequent to the administration of the peptide epitope, wherein the period of time between administering the vaccine composition and administering the at least one B cell epitope and/or mimotope of a cancer-associated antigen can be optimised to provide the desired synergistic or additive effect.

As noted elsewhere herein, the terms "cancer-associated antigen", "antigen associated with cancer, "tumour-associated antigen", "tumour antigen", "cancer antigen" and the like are used interchangeably herein to mean an antigen that is aberrantly expressed in cancer cells or tissue. In some embodiments, the antigen may be expressed under normal conditions in a limited number of tissues and/or organs or in specific developmental stages. For example, the antigen may be specifically expressed under normal conditions in stomach tissue and is expressed or aberrantly expressed (e.g., overexpressed) in one or more cancer cells. The expression of antigen may be reactivated in cancer cells or tissue irrespective of the origin of the cancer. In some embodiments, the cancer-associated antigen includes differentiation antigens, preferably cell type-specific differentiation antigens (i.e., proteins that are specifically expressed under normal conditions in a certain cell type at a certain differentiation stage), cancer/testis antigens (i.e., proteins that are specifically expressed under normal conditions in testis and sometimes in placenta), and germline specific antigens. In an embodiment, the antigen associated with cancer is expressed on the cell surface of a cancer cell and is preferably not or only rarely expressed on normal cells and tissues. Preferably, the antigen or the aberrant expression of the antigen identifies cancer cells, preferably tumour cells. In some embodiments, the antigen that is expressed by a cancer cell in a subject (e.g., a patient suffering from cancer) is a self-protein. It will be understood, however, that no autoantibodies directed against the antigen are typically found in a detectable level under normal conditions in a subject carrying the antigen (typically a healthy patient that does not have cancer) or such autoantibodies can only be found in an amount below a threshold concentration that would be necessary to damage the tissue or cells carrying the antigen.

In some embodiments, the amino acid sequence of the cancer-associated antigen is identical between the antigen as it is expressed in normal tissues and the antigen as it is expressed in cancer cells or tissue. In other embodiments, the cancer-associated antigen comprises a mutation in its amino acid sequence when compared to the amino acid sequence of the cancer-associated antigen as it would otherwise be expressed in normal tissue or cells.

It will be understood that the methods described herein are applicable to producing a vaccine composition for the treatment of any cancer, as long as the cancer is considered treatable by a targeted antibody response induced by the PD1 peptide epitope, alone or in combination with a targeted antibody response induced by the at least one B cell epitope and/or mimotope of a cancer-associated antigen, as herein described. Illustrative examples of suitable cancers include leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer, and lung cancer, lung carcinomas, prostate carcinomas, colon carcinomas, renal cell carcinomas, cervical carcinomas and the metastases thereof.

As used herein, the term "mimotope" typically refers to a molecule that has a conformation that has a topology equivalent to the B cell epitope of which it is a mimic and binds to the same antigen-binding region of an antibody which binds immunospecifically to said B cell epitope. The mimotope will elicit an immunological response in a host that is reactive to the antigen to which it is a mimic.

Mimotopes of a cancer-associated antigen are preferably antigenic polypeptides that, in their amino acid sequence, vary from the amino acid sequence of a native cancer-associated antigen. The mimotope may not only comprise amino acid substitutions of one or more naturally occurring amino acid residues of a native cancer-associated antigen, but also of one or more non-natural amino acids (i.e. not from the 20 "classical" amino acids) or they may be completely assembled of such non-natural amino acids. Suitable mimotopes may be provided from commercially available peptide libraries. Preferably, these mimotopes are at least 7 amino acids in length (e.g., 7, 8, 9, 10, 11, 12, 13, 14, 15, 16, 17 or more amino acids in length). Preferred lengths may be up to 16, preferably up to 14 or 20 amino acids (e.g. 5 to 16 amino acid residues). Longer mimotopes may also be employed. In an embodiment, the mimotope may be part of a polypeptide and consequently comprising at their N- and/or C-terminus at least one further amino acid residue.

Pharmaceutical Composition

In yet another aspect of the present disclosure, there is provided a pharmaceutical composition comprising the vaccine composition as herein described and a pharmaceutically acceptable excipient.

Suitable pharmaceutically acceptable excipients (e.g. carriers, diluents, etc.). will be known to persons skilled in the art. For example, a variety of aqueous (pharmaceutically acceptable) excipients may be used, such as buffered water, 0.4% saline, 0.3% glycine, hyaluronic acid and the like. These compositions may be sterilized by conventional, well known sterilization techniques or may be sterile-filtered. The resulting aqueous solutions may be packaged for use as is or lyophilized, the lyophilized preparation being combined with a sterile solution prior to administration. The compositions may further comprise pharmaceutically acceptable auxiliary substances as required to approximate physiological conditions, such as pH-adjusting and buffering agents, tonicity-adjusting agents, wetting agents and the like, for example sodium acetate, sodium lactate, sodium chloride, potassium chloride, calcium chloride, sorbitan monolaurate, triethanolamine oleate, sucrose or other carbohydrates, among many others. Suitable methods for preparing parenterally administrable compounds will be known or apparent to those skilled in the art and are described in more detail in, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7.sup.th ed., Lippincott, Williams, & Wilkins; and Handbook of Pharmaceutical Excipients (2000) A. H. Kibbe et al., eds., 3.sup.rd ed. Amer. Pharmaceutical Assoc.

The pharmaceutical composition may be in a form suitable for parenteral administration (e.g., subcutaneous, intramuscular or intravenous injection) or in an aerosol form suitable for administration by inhalation, such as by intranasal inhalation or oral inhalation.

The pharmaceutical compositions described herein may also be provided in a kit. The kit may comprise additional components to assist in performing the methods as herein described, such as administration device(s), excipients(s), carrier(s) and/or diluent(s). The kits may include containers for housing the various components and instructions for using the kit components in such methods.

In an embodiment disclosed herein, the pharmaceutic composition further comprises a checkpoint antigen or a checkpoint inhibitor, as herein described.

Uses and Methods of Treatment

In another aspect of the present disclosure, there is provided a method of treating a condition characterised by an involvement of PD1, the method comprising administering to a subject in need thereof the vaccine composition as herein described or the pharmaceutical composition as herein described.

The present disclosure also extends to use of the vaccine composition, as herein described, in the manufacture of a medicament for treating a condition characterized by an involvement of PD1 in a subject in need thereof.

The present disclosure also extends to the vaccine composition, as herein described, or the pharmaceutical composition, as herein described, for use in treating a condition characterized by an involvement of PD1 in a subject in need thereof.

Persons skilled in the art will be familiar with the type of conditions that are characterised by an involvement of PD1, illustrative examples of which include autoimmunity, cancer, chronic viral infection, and transplantation rejection. In an embodiment, the condition characterised by an involvement of PD1 is cancer. Illustrative examples include malignancies such as melanoma, non-small cell lung cancer, renal cell carcinoma, bladder cancer, Hodgkin's lymphoma, gastric cancer, pancreatic cancer, prostate cancer and salivary gland cancer. In an embodiment, the cancer is non-small cell lung cancer. In another embodiment, the cancer is melanoma. In another embodiment, the cancer is gastric cancer.

The vaccine or pharmaceutical compositions, as described herein, are typically administered in an "effective amount"; that is, an amount effective to elicit any one or more inter alia of a therapeutic effect. Persons skilled in the art would be able, by routine experimentation, to determine an effective, non-toxic amount to administer for the desired outcome. In general, the vaccine and/or pharmaceutical compositions, as disclosed herein, can be administered in a manner compatible with the route of administration and physical characteristics of the recipient (including health status) and in such a way that it elicits the desired effect(s) (i.e. therapeutic effect). For example, the appropriate dosage of a composition may depend on a variety of factors including, but not limited to, a subject's physical characteristics (e.g., age, weight, sex), whether the composition is being used as single agent or as part of adjunct therapy (e.g., with a checkpoint antigen or checkpoint inhibitor), the progression (i.e., pathological state) of any underlying cancer, and other factors that may be recognized by persons skilled in the art. Other illustrative examples of general considerations that may be considered when determining, for example, an appropriate dosage of the compositions are discussed by Gennaro (2000, "Remington: The Science and Practice of Pharmacy", 20th edition, Lippincott, Williams, & Wilkins; and Gilman et al., (Eds), (1990), "Goodman And Gilman's: The Pharmacological Bases of Therapeutics", Pergamon Press).

It is expected that the effective amount will fall in a relatively broad range that can be determined through methods known to persons skilled in the art, having regard to some of the considerations outlined above.

An effective amount of the peptide epitope to be administered will generally be in a range of from about 5 µg to about 5.0 mg of peptide sequence per subject, preferably from about 500 µg to about 5.0 mg of peptide epitope per subject, preferably from about 10 µg to about 500 µg of peptide epitope per subject, or from about 15 µg to about 60 µg of peptide epitope per subject. An effective amount can be ascertained, for example, by standard methods involving measurement of antigen-specific antibody titres. The level of immunity provided by the compositions herein described can be monitored to determine the need, if any, for boosters. For instance, following an assessment of an antigen-specific antibody titre in the serum, typically days or weeks following the first administration of the composition in a subject, optional booster immunisations may be required and/or desired. As noted elsewhere herein the use of a promiscuous Th cell epitope may enhance the antibody response that is raised by the immunogen described herein and, as such, a lower dose of the immunogen may be required. Where the immunogen comprises a promiscuous Th cell epitope, the immunogen may be administered to the subject in a range from about 5 g to about 5.0 mg of immunogen per subject, preferably from about 500 µg to about 5.0 mg of immunogen per subject, or preferably from about 1 mg to about 5 mg of immunogen per subject.

The vaccine and/or pharmaceutical compositions, as described herein, can be administered to a subject in need thereof in isolation or in combination with additional therapeutic agent(s); that is, as part of an adjunct therapy. In the context of adjunct therapy, the administration may be simultaneous or sequential; that is, the vaccine and/or pharmaceutical composition is administered first, followed by administration of the additional therapeutic and/or prophylactic agent(s), or the vaccine and/or pharmaceutical composition is administered following the administration of the additional therapeutic agent(s). Thus, where two or more entities are administered to a subject "in conjunction", they may be administered in a single composition at the same time, or in separate compositions at the same time, or in separate compositions separated in time.

The additional therapeutic agent(s) may comprise a checkpoint inhibitor. As noted elsewhere herein, the term "checkpoint antigen" typically means an antigen that is involved in endogenous inhibitory pathways for immune system function, such as those that act to maintain self-tolerance and modulate the duration and extent of immune response to antigenic stimulation. Studies have shown, however, checkpoint antigens reduce the effectiveness of a host's immune response towards the cancer, resulting in tumour growth (see Nirschl & Drake, 2013, *Clin Cancer Res* 19:4917-24). Suitable checkpoint antigens will be familiar to persons skilled in the art, illustrative examples of which are discussed by Pardoll (2012, *Nature Reviews Cancer* 12:252-64). Other illustrative examples of suitable checkpoint antigens include CTLA-4 (cytotoxic T lymphocyte antigen-4) and its ligands CD80 and CD86; PD-L1 (programmed cell death ligand 1), PD-L2 (programmed cell death ligand 2), LAG-3 (lymphocyte activation gene-3) and its ligand MHC class I or II, TIM-3 (T cell immunoglobulin and mucin protein-3) and its ligand GAL-9, B- and T-lymphocyte attenuator (BTLA) and its ligand herpes virus entry mediator (HVEM) and several others, as discussed, for example, by Nirschl & Drake (2013 *Clin Cancer Res* 19:4917-24).

The vaccine composition may target multiple antigens; that is, in addition to PD1. For example, the peptide epitope may further comprise one or more B cell epitopes and/or mimotopes of one or more cancer-associated antigens such that the peptide epitope, when administered, will induce an antibody response to PD1 and the one or more cancer-associated antigens (e.g., 2, 3, 4, 5, 6, 7 or more cancer-associated antigens). In yet another embodiment, the peptide epitope comprises one or more B cell epitopes and/or mimotopes of one or more additional checkpoint antigen (other than PD1) such that the peptide epitope, when administered, will induce an antibody response directed against the one or more additional checkpoint antigen (e.g., 1, 2, 3, 4, 5, 6, 7 or more checkpoint antigens other than PD1).

Thus, in an embodiment, the methods disclosed herein further comprise administering to the subject an antibody that specifically binds to a cancer-associated antigen, or an antigen-binding fragment thereof. In an embodiment, the cancer-associated antigen is selected from the group consisting of Her2/neu, Her-1, B melanoma antigen (BAGE), carcinoembryonic antigen (CEA), cytosine-phosphate diesterguanine (CpG), glycoprotein 100 (Gp100), telomerase transcriptase (h-TERT), melanoma antigen-encoding gene (MAGE), melanoma antigen recognized by T cells (Melan-A) and mucin-1 (MUC-1).

In an embodiment, the antibody or antigen-binding fragment thereof is administered to the subject subsequent to the administration of the vaccine composition.

It will be apparent to persons skilled in the art that the optimal quantity and spacing of individual dosages, if required to induce the desired immune response, can be determined, for example, by the form, route and site of administration, and the nature of the particular subject to be treated, as is described elsewhere herein. Optimum conditions can be determined using conventional techniques known to persons skilled in the art.

In some instances, it may be desirable to have several or multiple administrations of the vaccine and/or pharmaceutical compositions, as herein described. For example, the compositions may be administered 1, 2, 3, 4, 5, 6, 7, 8, 9, 10, or more times. The administrations may be from about one day intervals to about twelve week intervals, and in certain embodiments from about one to about four week intervals. Periodic re-administration may be required to achieve a desirable therapeutic result, such as a reduction in tumour size and/or a reduction in the occurrence of metastases. It will also be apparent to persons skilled in the art that the optimal course of administration can be ascertained using conventional course of treatment or efficacy or immune status determination tests.

It will be understood that "inducing" an immune or antigen-specific antibody response, as contemplated herein, includes eliciting or stimulating an immune response and/or enhancing a previously existing immune response to obtaining a desired therapeutic effect, such as a reduction in tumour size, a slowing of tumour growth and/or a reduction in the occurrence of metastases. The effect can also be prophylactic in terms of, for example, completely or partially preventing the occurrence of metastases.

As used herein, the terms "administration" or "administering" typically refer to the step of introducing the vaccine and/or pharmaceutical compositions, as herein described, into a patient's body so that the patient's immune system mounts a response to the peptide sequences within the peptide epitope. As used herein, a "subject in need thereof" includes an individual who has been diagnosed with cancer. In its broadest sense, the term "a patient in need thereof" therefore encompasses individuals with an already present need, as well as individuals who are at risk of developing cancer.

As used herein, a medicament which "treats" cancer will ideally eliminate the disease altogether by eliminating its underlying cause so that, upon cessation of administration of the composition, the disease does not re-develop, but remains in remission. As used herein, a medicament which "ameliorates" cancer does not eliminate the underlying cause of the disease, but reduces the severity of the disease as measured by any established grading system and/or as measured by an improvement in the patient's well-being, e.g. decrease in pain and/or discomfort.

All patents, patent applications and publications mentioned herein are hereby incorporated by reference in their entireties.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

As noted elsewhere herein, the vaccine compositions, as described herein, can be administered to a subject in need thereof in isolation or in combination with one or more additional therapeutic agents; that is, as part of an adjunct therapy. In the context of adjunct therapy, the administration may be simultaneous or sequential; that is, the vaccine composition is administered first, followed by administration of one or more additional therapeutic agents, or the vaccine composition is administered following the administration of the additional therapeutic agent(s). Thus, where two or more entities are administered to a subject "in conjunction", they may be administered in a single composition at the same time, or in separate compositions at the same time, or in separate compositions separated in time.

All patents, patent applications and publications mentioned herein are hereby incorporated by reference in their entireties.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Example 1—Identification and In Vitro Characterization of Mouse PD1 (mPD1) B Cell Epitopes A. Generation and Expression of Overlapping Peptides In order to test the efficacy of immunization against PD1 on tumour growth in vivo, experiments were performed to identify a mouse PD1 epitope as a surrogate to a human PD1 epitope, or a mimotope thereof, which would allow for subsequent tests to be conducted in a syngeneic mouse tumour model, as outlined in Example 3, below.

The protein sequence corresponding to the extracellular domain of mouse PD-1 (Q02242; Uniprot) was electronically back-translated into DNA sequences (ATG:Biosynthetics GmbH; Merzhausen, Germany). The protein-coding DNA sequences were partitioned into uniformly sized peptide-CDS as overlapping peptides in 15 amino acids (aa) length, with an offset of 3 aa, and the resulted DNA sequences were inserted into the expression vector pEPX-1 (ATG:Biosynthetics GmbH; Merzhausen, Germany). The DNA sequences were inserted downstream to the Glutathione S-transferases (GST)-coding gene, which, upon induction, resulted in a protein containing GST (26 kDa) fused to the N-terminus of the individual overlapping peptide. Expression vectors were used for transformation of E. coli strain BL21. Colonies (clones) of E. coli harbouring the expression vectors were picked from plates supplemented with Kanamycin and used for screening by colony blot assay. A colony harbouring the expression vector with no insert (i.e. control) was also picked.

B. Colony Blot Assay for Detection of Clones Expressing Specific Overlapping Peptide The clones of interest were replicated onto nitrocellulose membranes and lysed with lysis solution (Tris-HCl pH 8.0 50 mM, Lysozyme 200 µg/ml), followed by three cycles of freezing at −80C and thawing at 37C. After the last step of thawing, the membranes were incubated with the blocking solution containing PBS-5% skim milk. The blocking solution was discarded and the membranes were incubated for 2 h at RT with rat anti-mouse PD1 monoclonal antibody (mAb) (Biolegend, clone 29F.1A12). The membranes were then washed three times with PBS-Tween 0.0.5%, and incubated for 2 h at RT with the secondary antibody Goat Anti-rat IgG conjugated to Alkaline Phosphatase (Santa Cruz Biotechnology). After additional washing as above, the signals were developed using the substrate solution '1-Step NBT/BCIP' (Thermo Scientific). The following PD1 B cell epitope was identified as being reactive to the rat anti-mouse PD1 monoclonal antibody:

ISLHPKAKIEESPGA (amino acid residues 126-140 of mouse PD1 (mPD1); Uniprot No: Q02242; SEQ ID NO:119).

C. Dot Blot Assay for Detection of B Cell Epitopes in Bacterial Lysates

Bacterial culture of a clone expressing the B cell epitope candidate was used for preparation of cytosolic and total fraction of bacterial lysates. Two equal portions of the bacterial culture were centrifuged, and the bacterial pellets were lysed as above. Lysed bacteria were either further centrifuged and the supernatant was used as cytosolic fraction, or the lysed bacteria were used directly as total fraction.

The examined lysates were spotted onto nitrocellulose membranes for use in a dot blot assay. After blocking of the membranes with PBS-2% skim milk, the membranes were reacted with the monoclonal antibody (mAb), which had been used for detection of the positive clones in the colony blot assay, and the remaining procedures for detection were also as similar to the colony blot assay.

D. Purification of GST-Fused B Cell Epitope for Downstream Characterizations

The 0.22 µm-filtrated cytosolic fraction containing the GST-fused B cell epitope of interest was used for purification using 5 ml Glutathione Sepharose 4B (GSTrap; GE Healthcare), using freshly prepared elution buffer (50 mM Tris-HCl pH 8.0, containing 10 mM of reduced glutathione). The eluted material was examined by dot blot analysis as described as above and the purity of the materials as visualized by SDS-PAGE analysis.

E. SDS-Page Analysis

Figure 8:
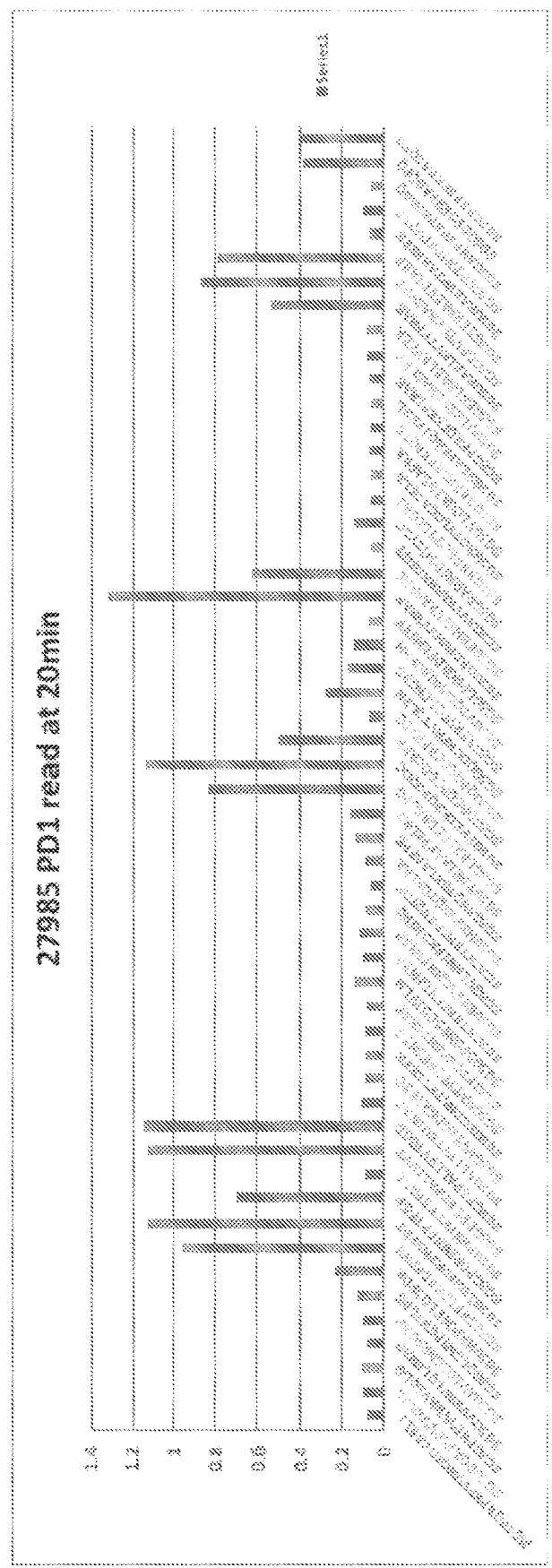
FIG. 8 shows the binding of a polyclonal anti-PD1 antibody (Sino Biological Inc.; Cat. No. 10377-RP03) to each of the 12-mer linear peptide fragments of human PD1. The amino acid sequences of the fragments (peptide sequences) are shown along the x-axis and represent (from left to right of the x-axis) SEQ ID NOs:2-54 and 62 of Table 1. The data show the optical density (OD) readings (y-axis) from the enzyme-linked immunosorbent assay (ELISA) at 450 nm.

A portion of the purified GST-B cell epitope combined with NuPage LDS Sample Buffer and NuPAGE Reducing Agent (Thermo Scientific) was run in NuPAGE 4-12% Bis-Tris gels for 35 min at 200 Voltage. The gel was then stained using Simply Blue Safe Stain (Thermo Scientific). The results are shown in FIG. 8.

F. Competitive ELISA

Figure 9:
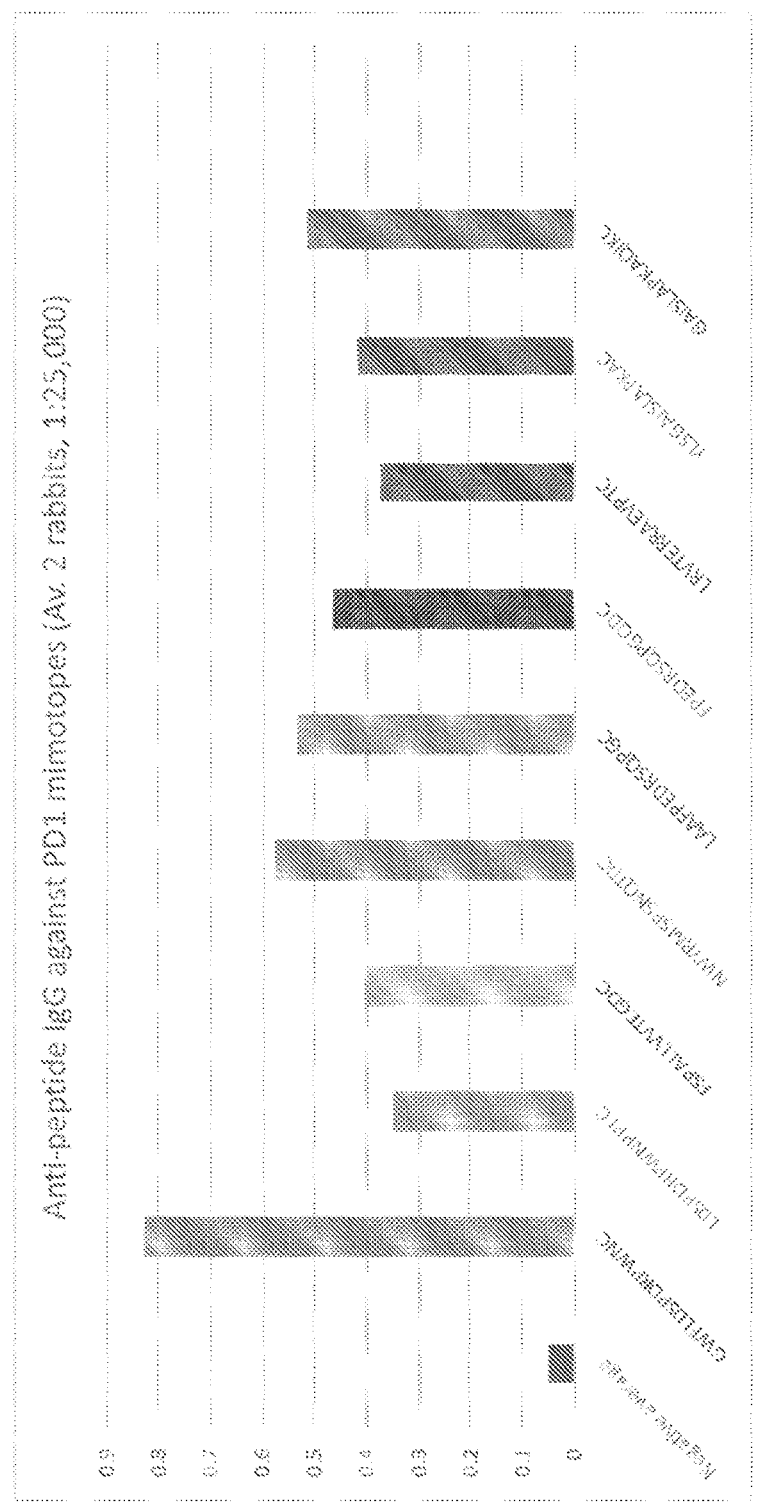
FIG. 9 shows the binding of affinity purified anti-peptide sequence antibodies (from immunised rabbit antisera, diluted 1:25,000) to native human PD1. The linear peptide fragments to which the rabbits were immunized are shown along the x-axis. The data show the optical density (OD) readings (y-axis) at 450 nm.

A competitive ELISA was employed to examine the capacity of the identified B cell epitope in inhibiting the binding of the anti-mouse-PD1 mAb to recombinant mouse PD1 used as coating antigen, onto which preincubated mixtures containing different concentrations of the mimotope and the mAb were applied. Anti-mouse PD-1 mAb bound to the coated recombinant mPD1 was detected using the secondary antibody mouse anti-Rat IgG (H+L) (Jackson Immunoresearch Laboratories; HRP-conjugated), and using TMB staining for detection (ELISA OD values, 450 nm). The results are shown in FIG. 9.

G. PD1 Expressing T Cell Lines

To produced T cells expressing mouse PD-1, Jurkat E6.1 NF-κB::eGFP reporter T cell line and the K562 stimulator cell line were cultured as previously described (Battin et al. *PLoS One*, 2017, 12(5):e0178220; PMID: 28542462). JE6.1 NF-kB::eGFP reporter cells expressing mouse PD-1 have been previously described (Jutz et al. *Oncotarget*, 2017, 8(39):64892-64906; PMID: 29029399). T cell stimulator cells, based on the K562 cell line (K562S), were generated by retrovirally transducing a CD5L-OKT3scFv-CD14 construct encoding an anti-human CD3 single chain fragment fused to human CD14 (Leitner et al. *J. Immunol. Methods*, 2010, 362(1-2):131-141; PMID: 20858499). K562S stimulate human T cells and T cell lines by ligating their TCR-CD3 complex. In order to separate stimulator cells from reporter cells, K562S were engineered to constitutively express a red fluorescent protein (RFP). Single cell clones were established to assure homogenous and comparable expression of the respective molecules. To confirm cell surface expression of respective molecules, a PE-conjugated anti-mPD-1 antibody (29F.1A12) from Biolegend (San Diego, CA) was used. Membrane-bound anti-CD3 fragment on K562S cells was detected with a PE-conjugated goat-anti-mouse IgG (H+L) antibody (Jackson ImmunoResearch, West Grove, PA). Acquisition of flow cytometry data was performed using FACS Calibur with CellQuest software (both BD Biosciences, San Jose, CA). Data was analysed using FlowJo software (version 10.0.8., Tree Star, Ashland, OR) and Graphpad Prism (version 5, GraphPad Software, Inc., La Jolla, CA).

H. Establishment of Tumour-Grafted Balb/C Mice

Mouse mammary carcinoma cells, without (D2F2) or transfected for stable expression of Her-2 (D2F2/E2), were used for establishing an in vivo setting involving mice developing tumours within 2-3 weeks and evaluating the effect of the mouse PD1 B cell epitope in tumor progression. Female Balb/C mice (Charles River, Sulzfeld, Germany; 6-8 week of age at the time of delivery) were grafted with different amounts of the cells:

Group-A: 0.5×E6/D2F2 cells/mouse s.c. (n=4)
Group-B: 1×E6/D2F2 cells/mouse s.c. (n=4)
Group-C: 2×E6/D2F2 cells/mouse s.c. (n=4)
Group-D: 0.5×E6/D2F2/E2 cells/mouse s.c. (n=4)
Group-E: 1×E6/D2F2/E2 cells/mouse s.c. (n=4)
Group-F: 2×E6/D2F2/E2 cells/mouse s.c. (n=4)

The size of the tumours was measured during the experiment and after the mice were sacrificed, with the results showing a significant increase in tumour size over the study period.

Figure 5:
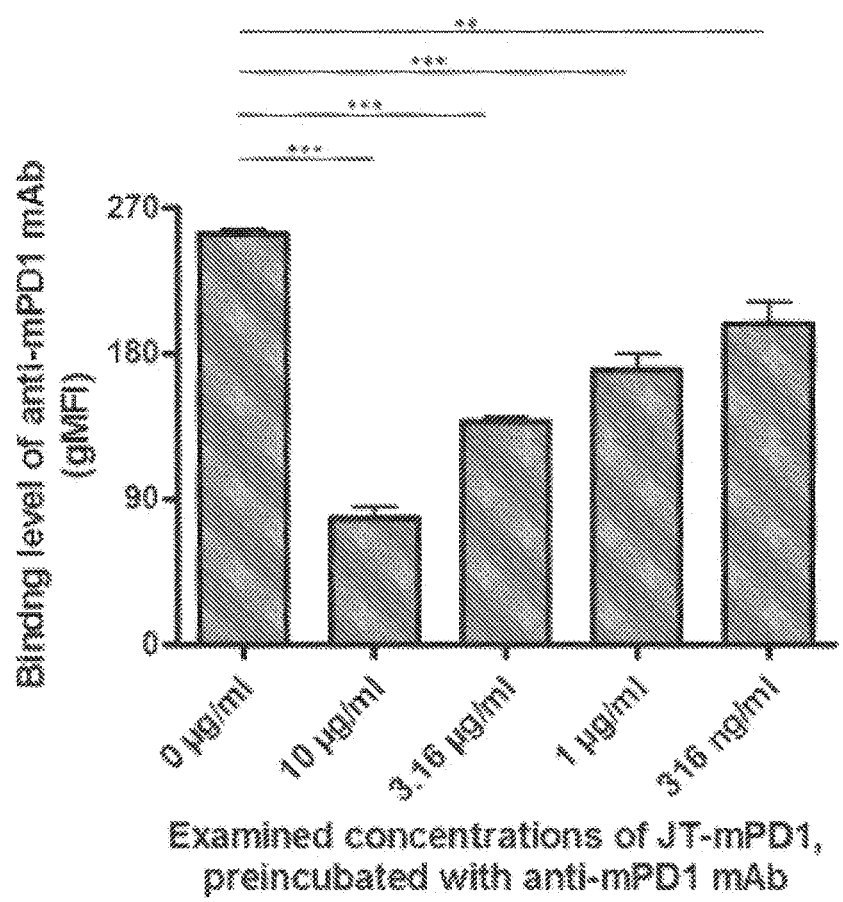
FIG. 5 shows the inhibitory activity of JT-mPD1 in a cellular assay. Jurkat T cells expressing mPD1 were used in a binding assay to examine the binding of an anti-mPD1 mAb alone or after pre-incubation with different concentrations of JT-mPD1. Significant differences are denoted by asterisks.

Example 2—Binding of Anti-mPD1 Monoclonal Antibodies to mPD1 is Inhibited in the Presence of the Mouse PD1 B Cell Epitope, JT-mPD1 (SEQ ID NO:119)

The ability of JT-mPD1 to inhibit binding of anti-mouse PD1 mAb was examined in the cell-based assay using mPD1-positive Jurkat T cells (see Example 1G). The anti-mouse PD1 mAb was tested alone and after pre-incubation with different concentrations of JT-mPD1. A maximal binding of the anti-mPD1 mAb was evident in the absence of JT-mPD1. This binding activity was dose-dependently inhibited in the presence of JT-mPD1 (see FIGS. 3 and 5).

Example 3—Immunization of Balb/C Mice and Characterization of Humoral and Cellular Responses to mPD1

Female Balb/C mice (Charles River, Sulzfeld, Germany; 6-8 week of age at the time of delivery) were used in an experimental setting including intraperitoneal administration of CRM-conjugated B cell epitope (Provepharm), together with Alum as adjuvant. The conjugated PD1 B cell epitope was diluted with NaCl solution and mixed with Alum prior injection. Six immunizations were carried out in 3 weeks intervals, and blood samples were taken prior each immunization and three weeks after the last immunization when the mice were sacrificed. The immunization experiment included the groups of naïve mice (n=4), mice immunized with 50 μg CRM (n=6), 10 μg of mPD1 B cell epitope-CRM conjugate (n=6) or 50 μg of mPD1-B cell epitope-CRM conjugate (n=6). Briefly, mice received a $1^{st}$ intraperitoneal dose of CRM alone or the mPD1 B cell epitope-CRM conjugate (10 μg or 50 μg) at day 1. Subsequent doses of CRM alone or the mPD1 B cell epitope-CRM conjugate were administered on day 21 ($2^{nd}$ dose), day 42 ($3^{rd}$ dose), day 63 ($4^{th}$ dose), and day 84 ($5^{th}$ dose). Blood samples were taken from the mice on day 0 (Pre Bleeding-BAG), day 41 (BA1), day 62 (BA2), day 83 (BA3), and day 104 (BA4). Animals were sacrificed on day 105.

Mice immunised with the mPD1 B cell epitope-CRM conjugate showed a clear antibody response to the mPD1-CRM conjugate, as illustrated by an increased titre of anti-mPD1 IgG antibodies at 41 days (BA1), 62 days (BA2), 83 days (BA3) and 104 days (BA4) after the first immunization at day 0 (FIG. 4). The mice immunised with either CRM alone or the mPD1 B cell epitope-CRM conjugate showed no adverse side effects, changes in body weight or any sign of inflammation.

Example 4—Specific IgG Antibodies Raised Against JT-mPD1 Block the mPD1/mPDL1 Interaction In Vitro The mPD1 B cell epitope (SEQ ID NO:119; JT-mPD1) was investigated to examine whether antibodies raised against this peptide can bind to native mPD1 and inhibit its interaction with mouse PDL1.

Briefly, rabbits were immunized at Charles River (France) by subcutaneous administration of 200 μg of the mPD1 B cell epitope (JT-mPD1) conjugated to keyhole limpet hemocyanin (KLH), followed by three additional doses at three weeks intervals. The rabbits were sacrificed two weeks after the fourth and final dose. Total and JT-PD1-specific IgG were isolated from the sera of immunised rabbits at Squarix (Germany).

The ability of isolated anti-JT-mPD1 IgG to bind to T cells expressing mPD1 was examined in a cellular assay using human Jurkat T cells expressing recombinant mPD1. The cells were incubated with anti-mouse PD1 mAb alone or after pre-incubation with increasing concentrations of JT-mPD1 peptide. As shown in FIG. 5, maximal binding of the anti-mouse PD1 mAb to recombinant mPD1-positive (mPD1+) Jurkat T cells was evident in the absence of JT-mPD1 IgG, whereas binding of the anti-mouse PD1 mAb to mPD1+ Jurkat T cells was inhibited dose-dependently by pre-incubation with JT-mPD1 (FIG. 5).

Figure 6:
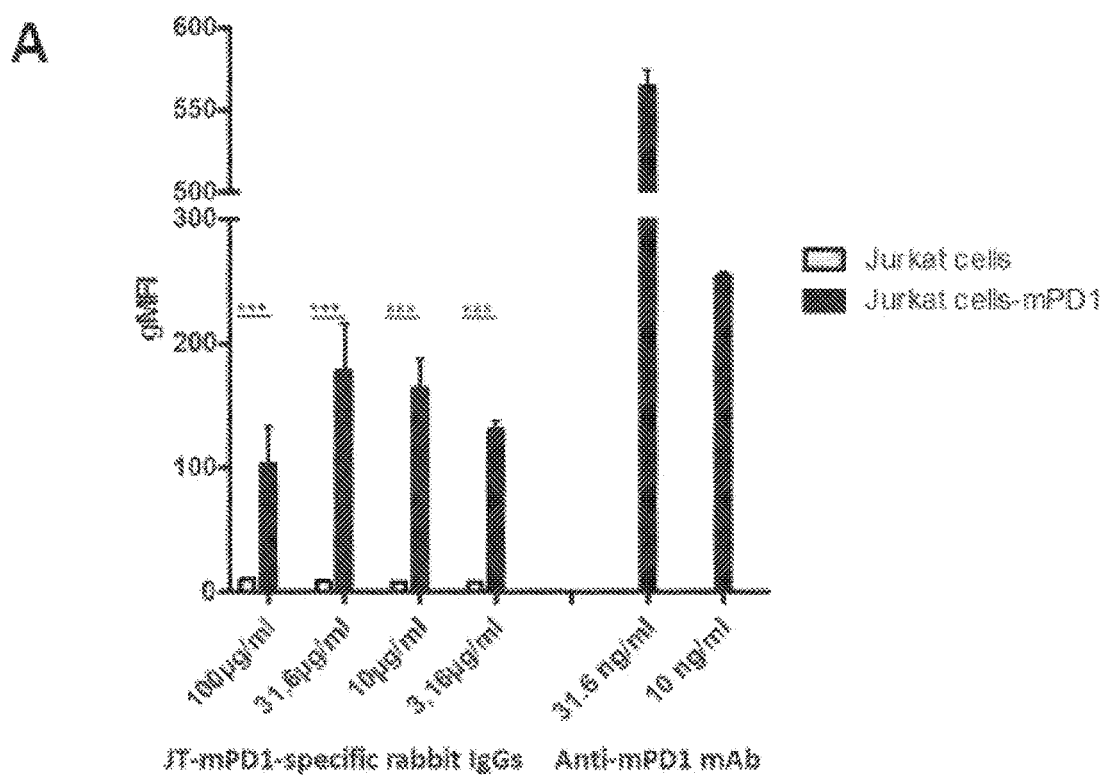
FIG. 6 shows binding of anti-JT-mPD1-IgG to recombinant mPD1 expressed on Jurkat T cells. A) Jurkat T cells expressing recombinant mPD1 were used in a binding assay, using different concentrations of the anti-JT-mPD1 IgG or anti-mPD1 mAb. B) Competitive ELISA, showing the binding of anti-mPD1 mAb (0.2 µg/ml) to mPD1 coated onto ELISA plates, before or after pre-incubation with different concentrations of (i) anti-JT-mPD1 IgG isolated from rabbits immunosed with JT-mPD1-KLH or (ii) total IgG isolated from PBS control rabbits (500 µg/ml). C) Competitive ELISA, showing the binding of recombinant mPDL1-Fc to mPD1-coated ELISA plates, before or after pre-incubation with different concentrations of anti-JT-mPD1 IgG or total IgG isolated from PBS control rabbits (500 µg/ml). Results are representative of repeated experiments. Significant differences are denoted by asterisks.
Figure 6:
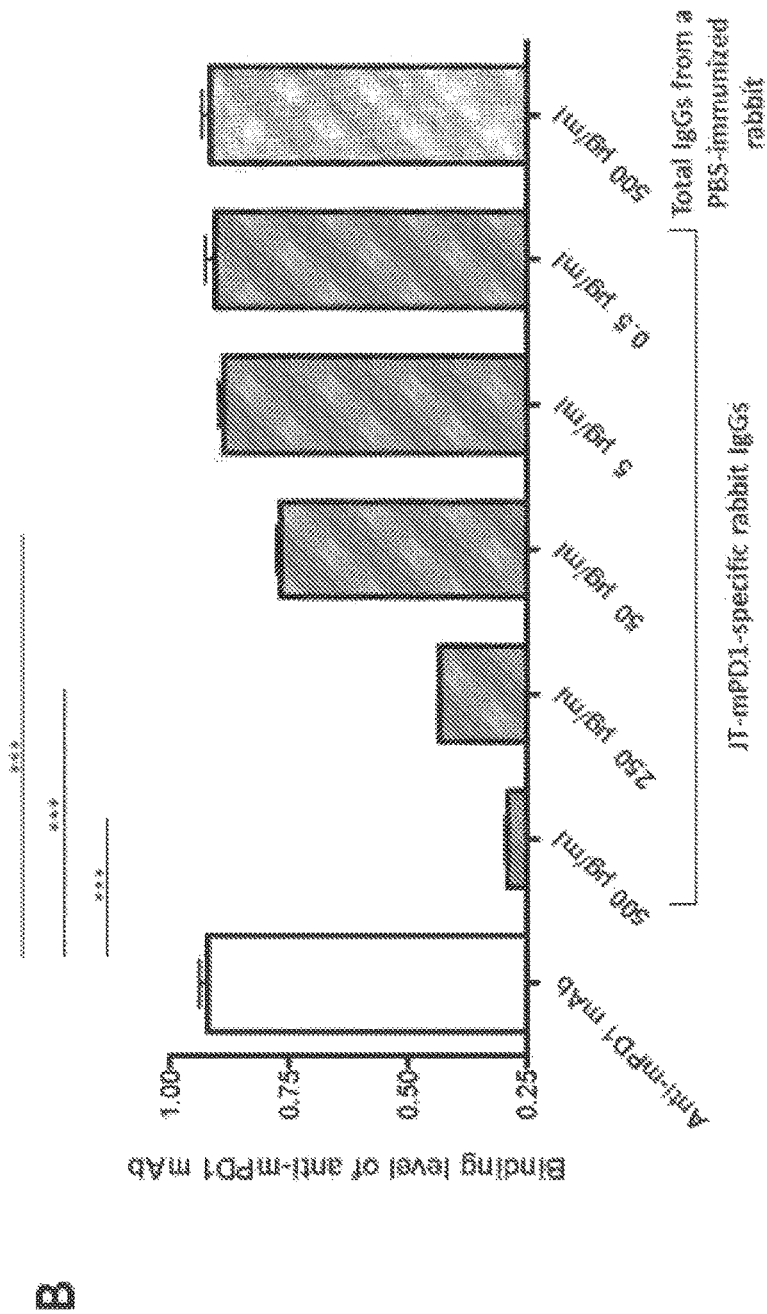
Figure 6:
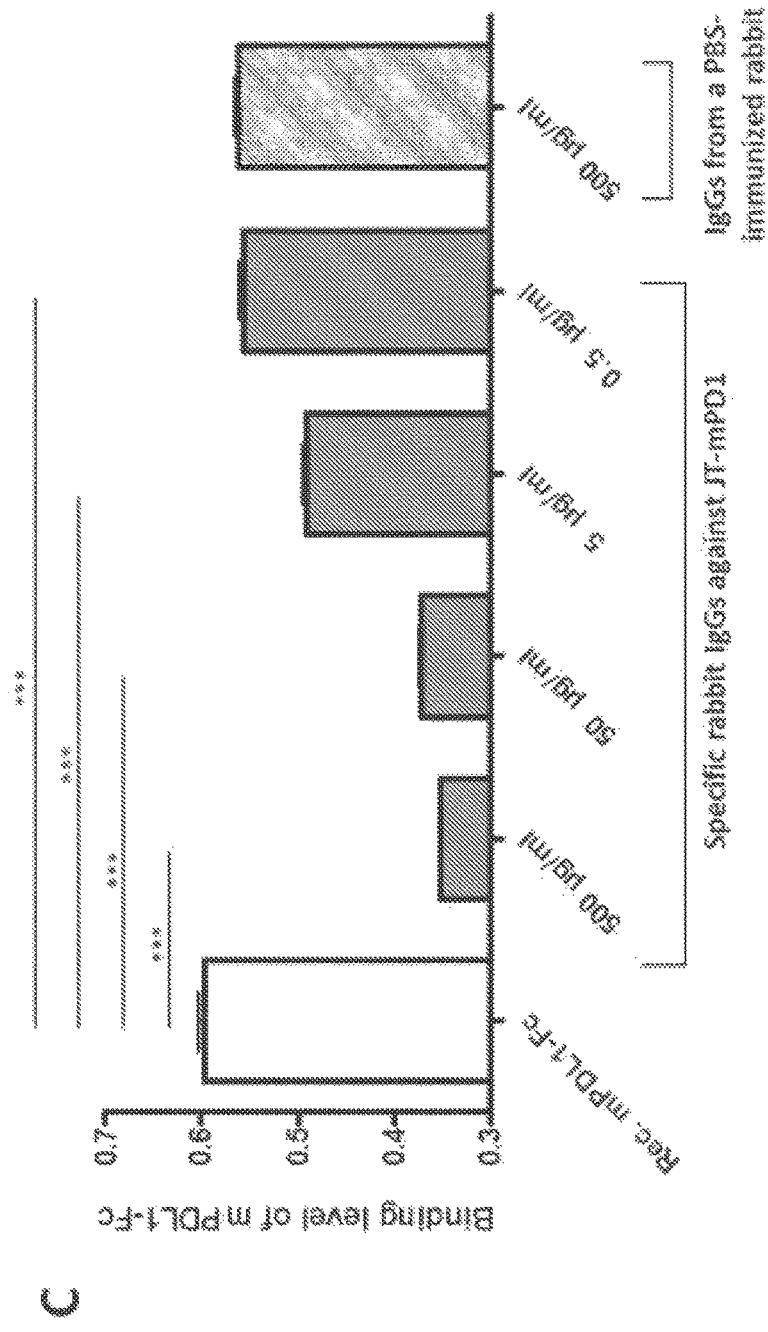

The mPD1 B cell epitope (JT-mPD1; SEQ ID NO:119) was further investigated to determine whether antibodies raised against this peptide can bind to mPD1 and inhibit the interaction of mPD1 with its ligand, mouse PDL1. As shown in FIG. 6A, anti-JT-mPD1 IgG did not bind to control (mPD1-negative) Jurkat cells, whereas the anti-JT-mPD1 IgG dose-dependently bound to mPD1+ Jurkat cells. These data demonstrate the specificity of antibodies raised against JT-mPD1 and their capacity in binding to native mPD1 on T cells. When the binding of the anti-JTmPD1 IgG was compared to the binding of the anti-mPD1 mAb, it was noted that stronger binding was evident with the anti-mPD1 mAb (FIG. 6A).

The capacity of the anti-JT-mPD1 IgG to inhibit the binding of anti-mPD1 mAb to mPD1 was also examined using a competitive ELISA. As shown in FIG. 6B, while the anti-mPD1 mAb alone bound to recombinant mPD1, pre-incubation with anti-JT-mPD1 IgG dose-dependently inhibited the binding of the anti-mPD1 mAb to recombinant mPD1. By contrast, pre-incubation with rabbit IgG raised isolated from non-immunised rabbits (PBS controls) had no inhibitory activity on anti-PD1 mAb binding to recombinant mPD1 in this assay. These results demonstrate that the anti-JT-mPD1 IgG and anti-mPD1 mAb bind to the same epitope on mPD1.

To examine whether anti-JT-mPD1 IgG can inhibit the interaction between mPD1 and mPDL1, a further competitive ELISA was performed. As shown in FIG. 6C, while rabbit IgG isolated from non-immunized (PBS control) rabbits at a concentration of 500 µg/ml had minimal effect on binding of mouse PDL1 to mPD1, the anti-JT-mPD1 IgG were shown to significantly and dose-dependently inhibit the binding of mouse PDL1 to mPD1.

Example 5—IgG Antibodies Against JT-mPD1 Confer Inhibition of Tumor Growth In Vivo This study sought to examine whether the anti-JT-mPD1 IgG can inhibit the interaction of mPD1/mPDL1 and reduce tumor growth in vivo.

Figure 7:
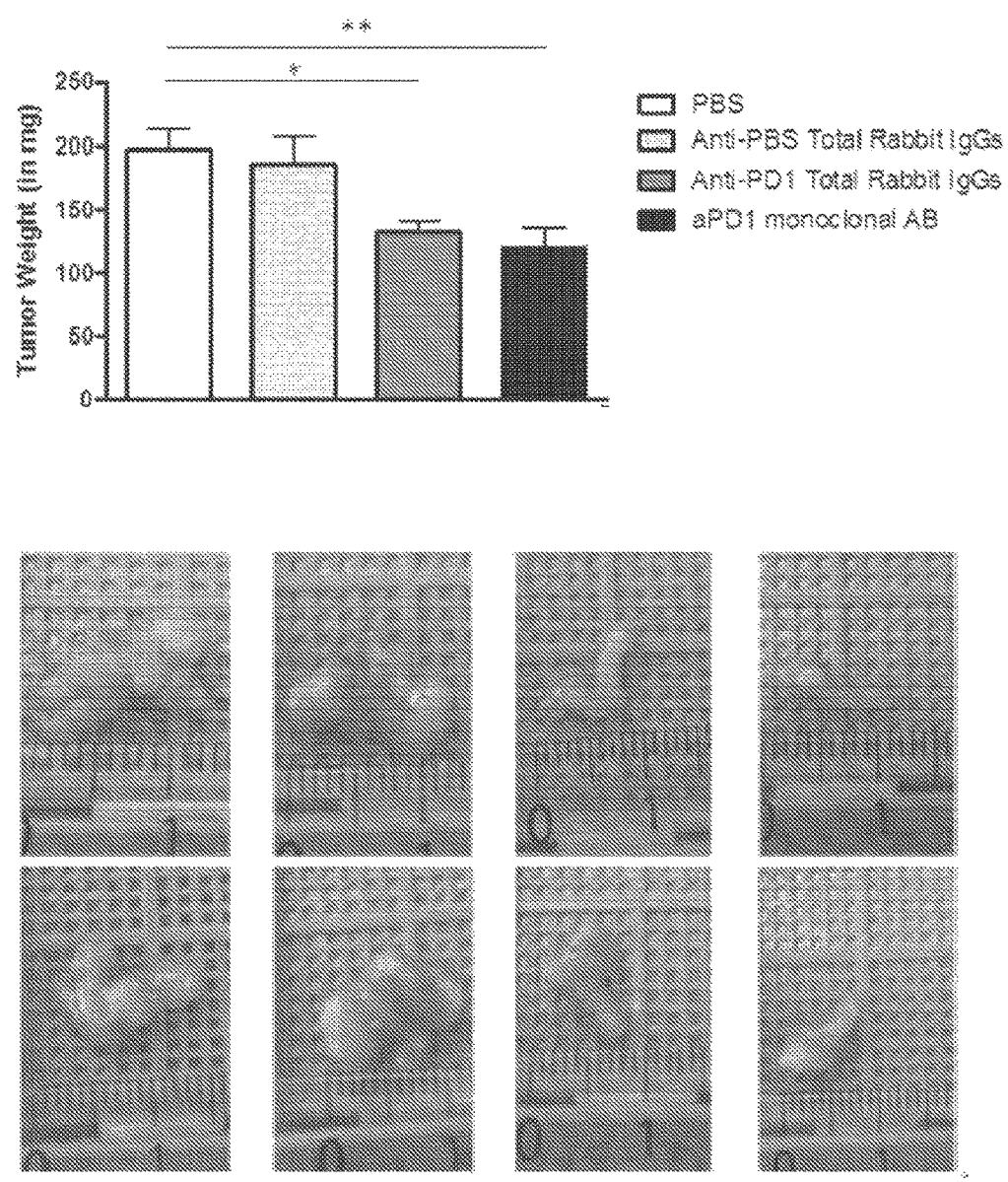
FIG. 7 shows anti-tumor activity of anti-JT-mPD1 IgG in a syngeneic mouse tumor model. BLAB/c mice were grafted with Her-2-expressing mammary carcinoma D2F2/E2 cells. The bars indicate the average weight of the tumors explanted from mice in each group at sacrifice. Corresponding macroscopic images of representative explanted tumors are shown below each bar. Significant differences are denoted by asterisks.

Briefly, BALB/c mice were grafted with mammary carcinoma cell line D2F2/E2, as described in Example 3, above. Animals then received either PBS (PBS controls), total rabbit IgG isolated from non-immunised rabbits (IgG controls) or anti-JT-mPD1 IgG. As shown in FIG. 7, while similar tumor weights were observed in PBS- or rabbit IgG-treated mice, a significant reduction in tumor weight was observed in the mice treated with anti-JT-mPD1 or with anti-mPD1 mAb. These results show that PD1 B cell epitopes can be used in a vaccine composition to raise an anti-PD1 antibody response in vivo, wherein the anti-PD1 antibodies inhibit the growth of established tumors.

Example 6: Screening a Library of Peptide Sequences by ELISA for B Cell Epitopes of PD1

A library of biotinylated peptide fragments of those listed in Table 1 (SEQ ID NOs:2-54 and 62) was generated and subsequently screened by enzyme-linked immunosorbent assays (ELISA) on streptavidin-coated plates using a polyclonal anti-PD1 antibody to identify peptide fragments to which the anti-PD1 antibody bound.

Biotinylated peptide fragments were supplied as a dry powder and reconstituted in 200 µL of either a pure solvent (e.g. dimethyl sulfoxide or dimethyl formamide) or solvent/water mixture. Each biotinylated peptide fragment was diluted just before use to a working concentration of 1:1000 in phosphate buffered saline (PBS) containing 0.1% bovine serum albumin (BSA) and 0.1% sodium azide.

To react the streptavidin coated, BSA blocked plates with the biotinylated peptide fragments, 100 µL of each of the diluted biotinylated peptide fragment solutions were transferred into the corresponding well positions of the plate and incubated on a shaker for a period of about 1 hr at 20° C.

The plates were then washed four times with PBS (0.01M sodium phosphate in 0.15M sodium chloride, pH7.2) containing 0.1% v/v Tween 20. After the washing steps, excess wash buffer was removed from the wells. The plates were then allowed to dry at 37° C.

The anti-PD1 polyclonal antibody (Sino Biological Inc.; Cat. No. 10377-RP03; a rabbit polyclonal antibody raised against recombinant human PD1/CD279) was diluted in 2% BSA/PBS containing 0.1% sodium azide. Approximately 100 µL of the diluted antibody was placed into each of the wells of the plate containing the captured biotinylated peptide fragments and incubated on a shaker for around 1 hr at 20° C. (or alternatively overnight at 4° C.). The plates were then washed four times with PBS/0.1% v/v Tween 20 and excess wash buffer was removed from each well.

Approximately 100 µL of a horseradish peroxidase-labeled anti-rabbit antibody was then added to each well and incubated for around 1 hr at 20° C. The plates were then washed four times with PBS/0.1% v/v Tween 20 and excess wash buffer was removed from each well. The plates were then washed twice with PBS only, to remove traces of Tween remaining from the washing buffer.

To detect the presence of horseradish peroxidase-labeled, anti-rabbit antibody, 100 µL of 1-Step™ ABTS (Pierce Cat. No. 37615) was added to each well and incubated for up to 45 min at 20° C. The absorbance of any colour change in each well was read using a microtitre Titertek Multiskan MC plate reader in the dual wavelength mode at 405 nm against a reference wavelength of 492 nm and compared to appropriate negative controls, such as the colour change observed in a well to which no biotinylated peptide fragment was added, to which no anti-PD1 polyclonal antibody was added and/or to which no horseradish peroxidase-labeled, anti-rabbit antibody was added.

The detection of a colour change (as compared to the appropriate controls) was indicative of the presence of the anti-PD1 polyclonal antibody bound to the biotinylated peptide fragment. The ELISA data are shown in FIG. 8. Thirteen peptide sequences were subsequently selected for immunisation studies—SEQ ID NOs: 9, 10, 13, 14, 28, 29, 36, 42, 43, 49 and 58-61.

Example 7—Immunization Protocol for Screening a Library of Peptide Fragments Capable of Raising an Antibody Response to PD1

A. Immunization of Rabbits

The thirteen peptide sequences identified and selected from the screening assay of Example 6, above, were subsequently conjugated to a carrier protein, Keyhole limpet hemocyanin (KLH). See Table 3:

TABLE 3

| Peptide Sequence | Carrier Protein | SEQ ID NO: |
|---|---|---|
| H-GWFLDSPDRPWNC-NH$_2$ | KLH | 9 |
| H-LDSPDRPWNPPTC-NH$_2$ | KLH | 10 |
| H-PPTFSPALLVVTC-NH$_2$ | KLH | 13 |
| H-FSPALLVVTEGDC-NH$_2$ | KLH | 14 |
| H-LAAFPEDRSQPGC-NH$_2$ | KLH | 28 |
| H-FPEDRSQPGQDC-NH$_2$ | KLH | 29 |
| H-GRDFHMSVVRARC-NH$_2$ | KLH | 36 |
| H-LRVTERRAEVPTC-NH$_2$ | KLH | 49 |
| H-FVLNWYRMSPSNC-NH$_2$ | KLH | 58 |
| H-NWYRMSPSNQTDC-NH$_2$ | KLH | 59 |
| H-RMSPSNQTDKLAC-NH$_2$ | KLH | 60 |
| H-YLSGAISLAPKAC-NH$_2$ | KLH | 61 |
| H-GAISLAPKAQIKC-NH$_2$ | KLH | 43 |

Approximately 250-500 µg of each KLH-conjugated peptide fragment was diluted with saline and subsequently emulsified in complete or incomplete Freund's adjuvant at a mass ratio of 1:1. The emulsified solution was administered to rabbits by subcutaneous injection around the shoulders and intramuscular injection into the legs in accordance with the following immunization protocol:

i. Day 00—Serum collected 2 ml (for 0.5-1.0 ml pre-immune serum;
ii. Day 01—1$^{st}$-immunization, complete Freund's adjuvant, 500 µg peptide fragment;
iii. Day 15—2$^{nd}$-immunization, complete Freund's adjuvant, 500 µg peptide fragment;
iv. Day 29—3$^{rd}$-immunization, incomplete Freund's adjuvant, 250 µg peptide fragment;
v. Day 35—Serum collected, 2-3 ml for assessment of anti-PD1 antibody titre by ELISA;
vi. Day 36—4$^{th}$-immunization, incomplete Freund's adjuvant, 250 µg peptide fragment (optional);
vii. Day 43—5$^{th}$-immunization, incomplete Freund's adjuvant. 250 µg peptide fragment (optional);
viii. Day 50—6$^{th}$-immunization, incomplete Freund's adjuvant 250 µg peptide fragment (optional);
ix. Day 57—7$^{th}$-immunization, incomplete Freund's adjuvant 250 µg peptide fragment (optional);
x. Day 63—Blood sample is collected from the immunised rabbits.

B. Assessment of Anti-PDJ Antibody Titre in Immunised Rabbits by ELISA

An enzyme-linked immunosorbent assays (ELISA) was used to measure the anti-PD1 antibody titre in the blood samples collected from the immunized rabbits. Briefly, microtiter plates were coated with PD1 (SEQ ID NO:1) conjugated to a His tag. After blocking the wells of the microtiter plates with BSA to minimise non-specific binding, diluted sera from the immunized rabbits were added to the plates and incubated on a shaker for around 1 hr at 20° C. (or alternatively overnight at 4° C.). The plates were then washed four times with PBS/0.1% v/v Tween 20 and excess wash buffer was removed from each well.

Approximately 100 µL of a horseradish peroxidase-labeled anti-rabbit antibody was then added to each well and incubated for around 1 hr at 20° C. The plates were then washed four times with PBS/0.1% v/v Tween 20 and excess wash buffer was removed from each well. The plates were then washed twice with PBS only, to remove traces of Tween remaining from the washing buffer.

To detect the presence of horseradish peroxidase-labeled, anti-rabbit antibody, 100 µL of 1-Step™ ABTS (Pierce Cat. No. 37615) was added to each well and incubated for up to 45 min at 20° C. The absorbance of any colour change in each well was read using a microtitre Titertek Multiskan MC plate reader in the dual wavelength mode at 405 nm against a reference wavelength of 492 nm and compared to appropriate negative controls, such as the colour change observed in a well to which no PD1 was added, to which no immunised rabbit sera was added and/or to which no horseradish peroxidase-labeled, anti-rabbit antibody was added.

The detection of a colour change (as compared to the appropriate controls) was indicative that an immune response was raised in the immunised rabbit to the peptide fragment. The peptide sequences that were identified as raising an anti-PD1 antibody response in the immunized rabbits are shown in Table 4, below. They were identified as SEQ ID NO:9 (sera no. 2809001), SEQ ID NO:10 (sera no. 2809003), SEQ ID NO:14 (sera no. 2809007), SEQ ID NO:28 (sera no. 2809009), SEQ ID NO:29 (sera no. 2809011), SEQ ID NO:49 (sera no. 2809015), SEQ ID NO:59 (sera no. 2809019), SEQ ID NO:61 (sera no. 2809023) and SEQ ID NO:43 (sera no. 2809025):

TABLE 4

| Protein ID | Sequence | Sera |
|---|---|---|
| PD1 | GWFLDSPORPWNC | 2809001 |
| PD1 | LDSPDRPWNPPTC | 2809003 |
| PD1 | FSPALLVVTEGDC | 2809007 |
| PD1 | LAAFPEDRSQPGC | 2808009 |
| PD1 | FPEDRSQPGQDC | 2809011 |
| PD1 | LRVTERRAEVPTC | 2809015 |
| PD1 | NWYRMSPSNQTDC | 2809019 |
| PD1 | YLSGAISLAPKAC | 2809023 |
| PD1 | GAISLAPKAQIKC | 2809025 |

The absorbance (OD) readings from the ELISA assays are shown in Tables 5 and 6, below, derived from two separate ELISA assays:

TABLE 5

ELISA assay no.1

| Protein ID | Sequence | Sera | Plate Protein | | | | | | | |
|---|---|---|---|---|---|---|---|---|---|---|
| | | | Rabbit 1 | | | | Rabbit 2 | | | |
| | | | 1/10 | 1/20 | PD1 1/40 | 1/80 | 1/10 | 1/20 | 1/40 | 1/80 |
| PD1 | GWFLDSPDRPWNC | 2809001 | 1.32 | 1.189 | 0.942 | 0.736 | 1.822 | 1.347 | 1.07 | 0.782 |
| PD1 | LDSPDRPWNPPTC | 2809003 | 0.198 | 0.144 | 0.126 | 0.095 | 0.293 | 0.21 | 0.184 | 0.121 |
| PD1 | PPTFSPALLVVTC | 2809005 | 0.499 | 0.371 | 0.23 | 0.151 | 0.713 | 0.445 | 0.283 | 0.205 |
| PD1 | FSPALLVVTEGDC | 2809007 | 0.223 | 0.188 | 0.135 | 0.101 | 0.307 | 0.177 | 0.146 | 0.105 |
| PD1 | LAAFPEDRSQPGC | 2809009 | 0.215 | 0.157 | 0.123 | 0.109 | 0.3 | 0.179 | 0.133 | 0.102 |
| PD1 | FPEDRSQPGQDC | 2809011 | 0.301 | 0.252 | 0.164 | 0.119 | 0.418 | 0.257 | 0.175 | 0.117 |
| PD1 | GRDFHMSVVRARC | 2809013 | 0.238 | 0.159 | 0.121 | 0.101 | 0.305 | 0.162 | 0.124 | 0.099 |
| PD1 | LRVTERRAEVPTC | 2809015 | 1.216 | 0.306 | 0.17 | 0.13 | 0.491 | 0.206 | 0.148 | 0.107 |
| PD1 | FVLNWYRMSPSNC | 2809017 | 0.623 | 0.203 | 0.112 | 0.084 | 0.41 | 0.167 | 0.123 | 0.09 |
| PD1 | NWYRMSPSNQTDC | 2809019 | 0.319 | 0.199 | 0.159 | 0.119 | 0.294 | 0.182 | 0.139 | 0.103 |
| PD1 | RMSPSNQTDKLAC | 2809021 | 0.296 | 0.163 | 0.133 | 0.1 | 0.304 | 0.176 | 0.142 | 0.107 |
| PD1 | YLSGAISLAPKAC | 2809023 | 0.519 | 0.299 | 0.214 | 0.16 | 0.45 | 0.238 | 0.179 | 0.132 |
| PD1 | GAISLAPKAQIKC | 2809025 | 2.22 | 2.025 | 1.914 | 1.871 | 2.259 | 1.951 | 2.012 | 2.05 |

TABLE 6

ELISA assay no.2

| Rabbit number | 28090 | PD1 coated plate | | | | | | | |
|---|---|---|---|---|---|---|---|---|---|
| | | −1 | −3 | −7 | −9 | −11 | −15 | −19 | −23 | −25 |
| Rabbit 1 | 1/100 | 1.67 | 1.941 | 0.261 | 1.172 | 1.02 | 1.78 | 0.065 | 0.136 | 0.519 |
| | 1/200 | 1.527 | 1.852 | 0.182 | 1.13 | 0.931 | 1.823 | 0.049 | 0.073 | 0.365 |
| | 1/400 | 1.77 | 1.73 | 0.131 | 1.481 | 0.878 | 1.743 | 0.039 | 0.059 | 0.299 |
| | 1/800 | 1.651 | 1.605 | 0.09 | 1.197 | 0.867 | 1.628 | 0.036 | 0.047 | 0.286 |
| Rabbit 2 | 1/100 | 1.744 | 2.038 | 0.385 | 1.47 | 1.317 | 1.766 | 0.062 | 0.108 | 0.594 |
| | 1/200 | 1.816 | 2.011 | 0.215 | 1.219 | 1.052 | 1.815 | 0.041 | 0.063 | 0.412 |
| | 1/400 | 1.78 | 1.941 | 0.136 | 1.269 | 1.02 | 1.873 | 0.036 | 0.049 | 0.31 |
| | 1/800 | 1.755 | 1.848 | 0.104 | 1.508 | 0.867 | 1.705 | 0.036 | 0.041 | 0.224 |

Example 8—Immunization Protocol with Fusion Peptides of SEQ ID NOs:9 and 43

Peptide sequences SEQ ID NOs: 9 and 43 were combined to form 2 different fusion peptides—SEQ ID NO:56 and SEQ ID NO:57—which were then conjugated to KLH. See Table 7 (SEQ ID NO:9 is underlined):

TABLE 7

| Peptide Sequence | Carrier Protein |
|---|---|
| H-GWFLDSPDRPWNGAISLAPKAQIKC-NH₂ | KLH |
| H- GAISLAPKAQIKGWFLDSPDRPWN-NH₂ | KLH |

Approximately 250-500 μg of each KLH-conjugated fusion peptides were diluted with saline and subsequently emulsified in complete or incomplete Freund's adjuvant at a mass ratio of 1:1. The emulsified solutions were administered to rabbits by subcutaneous injection around the shoulders and intramuscular injection into the legs in accordance with the immunization protocol of Example 2, above.

An enzyme-linked immunosorbent assays (ELISA) was used to measure the anti-PD1 antibody titre in the blood samples collected from the immunized rabbits, in accordance with the methodology set out in Example 2 above. The absorbance readings from the ELISA assay are shown in Table 8, below (SEQ TD NO:9 is underlined):

TABLE 8

| PD1 fusion | GWFLDSPDRPWNGAISLAPKAQIKC | 2916501 |
|---|---|---|
| PD1 fusion | GAISLAPKAQIKGWFLDSPDRPWNC | 2916503 |

| | PD1 coated plate | |
|---|---|---|
| | 2916501 | 2916503 |
| Rabbit number | 1.612 | 1.566 |
| Rabbit 1 | 1.685 | 1.838 |
| | 1.482 | 1.704 |
| | 1.068 | 1.477 |
| | 1.841 | 1.53 |
| Rabbit 2 | 1.919 | 1.856 |
| | 1.777 | 1.695 |
| | 1.521 | 1.742 |

Example 9—Cross-Reactivity of Anti-PD1 Antibodies Derived from Immunized Rabbits to PD1 of Other Species To assess whether or not the anti-human PD1 antibodies raised in the immunised rabbits would cross-react with PD1 of other species, the anti-PD1 antisera from the Examples 7 and 8, above, were screened in an ELISA assay for binding to mouse, rhesus monkey, canine and rat PD1 proteins. The OD readings from the ELISA assays are shown in Table 9, below:

TABLE 9

Affinity purified anti-PD1 antibodies, raised to the peptides of SEQ ID NO: 9 (sera no. 2809001), SEQ ID NO: 10 (sera no. 2809003), SEQ ID NO: 14 (sera no. 2809007), SEQ ID NO: 28 (sera no. 2809009), SEQ ID NO: 29 (sera no. 2809011), SEQ ID NO: 49 (sera no. 2809015), SEQ ID NO: 59 (sera no. 2809019), SEQ ID NO: 61 (sera no. 2809023), SEQ ID NO: 43 (sera no. 2809025), SEQ ID NO: 56 (sera no. 2916501) and SEQ ID NO: 57 (sera no. 2916503), were screened for binding to PD1 protein of different species. All antibodies were diluted 1/100.

| Rabbit number | 2809001 | 2809003 | 2809007 | 2809009 | 2809011 | 2809015 | 2809019 | 2809023 |
|---|---|---|---|---|---|---|---|---|
| Rabbit 1 | 0.193 | 0.112 | 0.091 | 0.139 | 0.105 | 0.092 | 0.069 | 0.101 |
| Rabbit 2 | 0.213 | 0.168 | 0.109 | 0.207 | 0.107 | 0.096 | 0.067 | 0.088 |
| Rabbit 1 | 1.67 | 1.941 | 0.261 | 1.172 | 1.02 | 1.78 | 0.065 | 0.136 |
| Rabbit 2 | 1.744 | 2.038 | 0.385 | 1.47 | 1.317 | 1.766 | 0.062 | 0.108 |
| Rabbit 1 | 1.194 | 1.504 | 0.139 | 0.839 | 0.886 | 2.597 | 0.08 | 0.141 |
| Rabbit 2 | 1.326 | 1.552 | 0.203 | 0.93 | 0.96 | 1.925 | 0.074 | 0.127 |
| Rabbit 1 | 1.628 | 1.058 | 0.098 | 0.188 | 0.091 | 0.431 | 0.068 | 0.094 |
| Rabbit 2 | 1.901 | 1.308 | 0.116 | 0.306 | 0.115 | 0.417 | 0.065 | 0.084 |
| Rabbit 1 | 0.263 | 0.103 | 0.084 | 0.109 | 0.078 | 0.08 | 0.079 | 0.093 |
| Rabbit 2 | 0.141 | 0.113 | 0.084 | 0.132 | 0.096 | 0.079 | 0.063 | 0.071 |

| Rabbit number | 2809025 | 2916501 | 2916503 | conjugate only | Species | Supplier |
|---|---|---|---|---|---|---|
| Rabbit 1 | 0.081 | 0.084 | 0.112 | 0.066 | Mouse | |
| Rabbit 2 | 0.09 | 0.098 | 0.113 | 0.064 | Mouse | Sino |
| Rabbit 1 | 0.519 | 1.612 | 1.566 | | Human | |
| Rabbit 2 | 0.594 | 1.841 | 1.53 | | Human | Sino |
| Rabbit 1 | 0.739 | 1.428 | 0.998 | 0.063 | Rhesus | |
| Rabbit 2 | 0.748 | 1.781 | 1.193 | 0.058 | Rhesus | Sino |
| Rabbit 1 | 0.071 | 1.008 | 1.636 | 0.059 | Canine | |
| Rabbit 2 | 0.079 | 1.244 | 1.926 | 0.06 | Canine | Sino |
| Rabbit 1 | 0.118 | 0.102 | 0.075 | — | Rat | |
| Rabbit 2 | 0.105 | 0.109 | 0.087 | 0.055 | Rat | Sino |

His tagged PD1, for each species, bound to nickel coated plates at 2.5 µg/ml

Example 10—Comparison of the Cross-Reactivity of Anti-PD1 Antibodies Derived from Immunized Rabbits to PD1 of Other Species A further ELISA assay was performed to make a direct comparison of the cross-reactivity of anti-human PD1 antibodies raised in the immunised rabbits (Rabbits 1 and 2) to PD1 proteins of different species. The OD readings are shown in Table 10, below:

TABLE 10

Affinity purified anti-PD1 antibodies, raised to the peptides and fusion peptides of SEQ ID NO: 9 (sera no. 2809001), SEQ ID NO: 43 (sera no. 2809025) and SEQ ID NO: 57 (sera no. 2916503), were screened for binding to PD1 protein of different species (all antibodies were diluted 1/100).

| Species PD1 protein | Rabbit 1 2916503 | Rabbit 2 2916503 | Rabbit 1 2809001 | Rabbit 2 2809001 | Rabbit 1 2809025 | Rabbit 2 2809025 |
|---|---|---|---|---|---|---|
| Mouse | 0.156 | 0.117 | 0.493 | 0.386 | 0.12 | 0.102 |
| Human | 0.835 | 0.72 | 0.847 | 0.82 | 0.561 | 0.453 |
| Rhesus | 1.042 | 1.268 | 0.917 | 0.779 | 1.075 | 0.958 |
| Cynomolgus | 0.584 | 0.533 | 0.634 | 0.621 | 0.502 | 0.482 |
| Canine | 0.972 | 0.73 | 1.121 | 1.236 | 0.118 | 0.125 |
| Rat | 0.128 | 0.108 | 0.348 | 0.306 | 0.153 | 0.143 |
| background | 0.044 | 0.042 | 0.045 | 0.041 | 0.047 | 0.042 |

SUMMARY

Using anti-PD1 polyclonal antibodies, the inventors screened a library of 54 linear peptide fragments of human PD1 (12-mer, offset by 3 amino acids) and identified a total of 13 peptide sequences to which the anti-PD1 polyclonal antibodies bound. The 13 peptide sequences were each conjugated to a carrier protein (KLH) and the KLH-conjugated peptides were subsequently injected into rabbits. Antisera from the immunised rabbits were collected and anti-PD1 antibodies were affinity purified from the antisera and screened for binding to native human PD1. The inventors unexpectedly found that of the 13 peptide conjugates that were used to immunised the rabbits, only 9 conjugates generated sufficient anti-PD1 antibody titres—SEQ ID NOs: 9, 10, 14, 28, 29, 49, 59, 61 and 43. Of the 9 peptide sequences that raised a marked anti-PD1 antibody titre in the immunised rabbits, SEQ ID NO:9 generated the highest anti-PD1 antibody titre. Anti-PD1 antibodies were also raised in animals immunized with fusion peptides comprising SEQ ID NO:9 and SEQ ID NO:43 (SEQ ID NO:56 and SEQ ID NO:57).

The affinity-purified, anti-PD1 antibodies from animals immunised with peptide sequences SEQ ID NOs:9, 10, 14, 28, 29, 49, 59, 61, 43, 56 and 57 showed at least some cross-reactivity with PD1 protein from other species—mouse, rat, Rhesus monkey, Cynomolgus monkey and canine—with greatest cross-reactivity to PD1 protein from Rhesus and Cynomolgus monkeys.

These data show that small linear peptides of PD1 can be used in a vaccine composition to raise an antibody response in vivo, where the antibodies bind to native PD1 in that subject, and can therefore be used for the treatment of conditions characterised by an involvement of PD1, such as cancer.

The invention claimed is:

1. A method of treating a cancer, the method comprising administering to a human subject having a cancer characterized by an involvement of programmed cell death protein 1 (PD1) a vaccine composition comprising an effective amount of an immunogen that induces an antibody response in which the antibody binds to a B cell epitope of PD1, wherein the immunogen comprises a B cell epitope of PD1, wherein the B cell epitope of PD1 consists of an amino acid sequence selected from the group consisting of SEQ ID NOs: 9, 10, 14, 24, 28, 29, 42, 43, 49, and a combination of two or more of the foregoing, and wherein the amino acid sequence of the immunogen is not identical to a continuous stretch of at least 50 amino acid residues of PD1.

2. The method of claim 1, wherein the B cell epitope of PD1 consists of an amino acid sequence selected from the group consisting of SEQ ID NOs: 9, 43, 56 and 57.

3. The method of claim 1, further comprising administering to the subject an antibody, or an antigen-binding fragment thereof, that specifically binds to a cancer-associated antigen.

4. The method of claim 1, wherein the immunogen comprises a carrier.

5. The method of claim 4, wherein the carrier is diphtheria toxin variant CRM-197 (SEQ ID NO:118).

6. The method of claim 1, wherein the vaccine composition comprises an adjuvant.

7. The method of claim 6, wherein the adjuvant is a TLR-4 agonist.

8. The method of claim 6, wherein the adjuvant is a water in oil emulsion.

9. A vaccine composition for raising a humoral response to PD1, wherein the vaccine composition comprises an immunogen that induces an antibody response in which the antibody binds to a B cell epitope of PD1, wherein the immunogen comprises a B cell epitope of PD1, wherein the B cell epitope of PD1 consists of an amino acid sequence selected from the group consisting of SEQ ID NOs: 9, 10, 14, 24, 28, 29, 42, 43, and 49, and a combination of two or more of any of the foregoing, wherein the amino acid sequence of the immunogen is not identical to a continuous stretch of at least 50 amino acid residues of PD1, and wherein the vaccine composition further comprises an adjuvant.

10. The vaccine composition of claim 9, wherein the B cell epitope of PD1 consists of the amino acid sequence selected from the group consisting of SEQ ID NO: 9 and SEQ ID NO: 43.

11. The vaccine composition of claim 9, wherein the immunogen further comprises a promiscuous T helper cell epitope.

12. The vaccine composition of claim 9, wherein the B cell epitope of PD1 consists of a fusion of two or more of SEQ ID NOs: 9, 10, 14, 24, 28, 29, 42, 43, and 49.

13. The vaccine composition of claim 9, wherein the B cell epitope of PD1 consists of an amino acid sequence selected from the group consisting of SEQ ID NO: 56 and SEQ ID NO: 57.

14. A pharmaceutical composition comprising the vaccine composition of claim 9 and a pharmaceutically acceptable excipient.

15. A method of treating cancer, the method comprising administering to a subject having a cancer characterised by an involvement of PD1 the vaccine composition of claim 9.

16. The method of claim 15, further comprising administering to the subject an antibody that specifically binds to a cancer-associated antigen, or an antigen-binding fragment thereof.

* * * * *

SEQUENCE LISTING

<160> NUMBER OF SEQ ID NOS: 119

<210> SEQ ID NO 1
<211> LENGTH: 170
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val
                165                 170

<210> SEQ ID NO 2
<211> LENGTH: 12
<212> TYPE: PRT
<213> ORGANISM: Homo sapiens

<400> SEQUENCE: 2

Met Gln Ile Pro Gln Ala Pro Trp Pro Val Val Trp
1               5                   10

<210> SEQ ID NO 3
<211> LENGTH: 12
<212> TYPE: PRT
<213> ORGANISM: Homo sapiens

<400> SEQUENCE: 3

Pro Gln Ala Pro Trp Pro Val Val Trp Ala Val Leu
1               5                   10

<210> SEQ ID NO 4
<211> LENGTH: 12
<212> TYPE: PRT
<213> ORGANISM: Homo sapiens

<400> SEQUENCE: 4

Pro Trp Pro Val Val Trp Ala Val Leu Gln Leu Gly
1               5                   10

<210> SEQ ID NO 5
<211> LENGTH: 12

<212> TYPE: PRT
<213> ORGANISM: Homo sapiens

<400> SEQUENCE: 5

Val Val Trp Ala Val Leu Gln Leu Gly Trp Arg Pro
1               5                   10

<210> SEQ ID NO 6
<211> LENGTH: 12
<212> TYPE: PRT
<213> ORGANISM: Homo sapiens

<400> SEQUENCE: 6

Ala Val Leu Gln Leu Gly Trp Arg Pro Gly Trp Phe
1               5                   10

<210> SEQ ID NO 7
<211> LENGTH: 12
<212> TYPE: PRT
<213> ORGANISM: Homo sapiens

<400> SEQUENCE: 7

Gln Leu Gly Trp Arg Pro Gly Trp Phe Leu Asp Ser
1               5                   10

<210> SEQ ID NO 8
<211> LENGTH: 12
<212> TYPE: PRT
<213> ORGANISM: Homo sapiens

<400> SEQUENCE: 8

Trp Arg Pro Gly Trp Phe Leu Asp Ser Pro Asp Arg
1               5                   10

<210> SEQ ID NO 9
<211> LENGTH: 12
<212> TYPE: PRT
<213> ORGANISM: Homo sapiens

<400> SEQUENCE: 9

Gly Trp Phe Leu Asp Ser Pro Asp Arg Pro Trp Asn
1               5                   10

<210> SEQ ID NO 10
<211> LENGTH: 12
<212> TYPE: PRT
<213> ORGANISM: Homo sapiens

<400> SEQUENCE: 10

Leu Asp Ser Pro Asp Arg Pro Trp Asn Pro Pro Thr
1               5                   10

<210> SEQ ID NO 11
<211> LENGTH: 12
<212> TYPE: PRT
<213> ORGANISM: Homo sapiens

<400> SEQUENCE: 11

Pro Asp Arg Pro Trp Asn Pro Pro Thr Phe Ser Pro
1               5                   10

<210> SEQ ID NO 12
<211> LENGTH: 12
<212> TYPE: PRT
<213> ORGANISM: Homo sapiens

```
<400> SEQUENCE: 12

Pro Trp Asn Pro Pro Thr Phe Ser Pro Ala Leu Leu
1               5                   10

<210> SEQ ID NO 13
<211> LENGTH: 12
<212> TYPE: PRT
<213> ORGANISM: Homo sapiens

<400> SEQUENCE: 13

Pro Pro Thr Phe Ser Pro Ala Leu Leu Val Val Thr
1               5                   10

<210> SEQ ID NO 14
<211> LENGTH: 12
<212> TYPE: PRT
<213> ORGANISM: Homo sapiens

<400> SEQUENCE: 14

Phe Ser Pro Ala Leu Leu Val Val Thr Glu Gly Asp
1               5                   10

<210> SEQ ID NO 15
<211> LENGTH: 12
<212> TYPE: PRT
<213> ORGANISM: Homo sapiens

<400> SEQUENCE: 15

Ala Leu Leu Val Val Thr Glu Gly Asp Asn Ala Thr
1               5                   10

<210> SEQ ID NO 16
<211> LENGTH: 12
<212> TYPE: PRT
<213> ORGANISM: Homo sapiens

<400> SEQUENCE: 16

Val Val Thr Glu Gly Asp Asn Ala Thr Phe Thr Cys
1               5                   10

<210> SEQ ID NO 17
<211> LENGTH: 12
<212> TYPE: PRT
<213> ORGANISM: Homo sapiens

<400> SEQUENCE: 17

Glu Gly Asp Asn Ala Thr Phe Thr Cys Ser Phe Ser
1               5                   10

<210> SEQ ID NO 18
<211> LENGTH: 12
<212> TYPE: PRT
<213> ORGANISM: Homo sapiens

<400> SEQUENCE: 18

Asn Ala Thr Phe Thr Cys Ser Phe Ser Asn Thr Ser
1               5                   10

<210> SEQ ID NO 19
<211> LENGTH: 12
<212> TYPE: PRT
<213> ORGANISM: Homo sapiens

<400> SEQUENCE: 19
```

```
Phe Thr Cys Ser Phe Ser Asn Thr Ser Glu Ser Phe
1               5                   10

<210> SEQ ID NO 20
<211> LENGTH: 12
<212> TYPE: PRT
<213> ORGANISM: Homo sapiens

<400> SEQUENCE: 20

Ser Phe Ser Asn Thr Ser Glu Ser Phe Val Leu Asn
1               5                   10

<210> SEQ ID NO 21
<211> LENGTH: 12
<212> TYPE: PRT
<213> ORGANISM: Homo sapiens

<400> SEQUENCE: 21

Asn Thr Ser Glu Ser Phe Val Leu Asn Trp Tyr Arg
1               5                   10

<210> SEQ ID NO 22
<211> LENGTH: 12
<212> TYPE: PRT
<213> ORGANISM: Homo sapiens

<400> SEQUENCE: 22

Glu Ser Phe Val Leu Asn Trp Tyr Arg Met Ser Pro
1               5                   10

<210> SEQ ID NO 23
<211> LENGTH: 12
<212> TYPE: PRT
<213> ORGANISM: Homo sapiens

<400> SEQUENCE: 23

Val Leu Asn Trp Tyr Arg Met Ser Pro Ser Asn Gln
1               5                   10

<210> SEQ ID NO 24
<211> LENGTH: 12
<212> TYPE: PRT
<213> ORGANISM: Homo sapiens

<400> SEQUENCE: 24

Trp Tyr Arg Met Ser Pro Ser Asn Gln Thr Asp Lys
1               5                   10

<210> SEQ ID NO 25
<211> LENGTH: 12
<212> TYPE: PRT
<213> ORGANISM: Homo sapiens

<400> SEQUENCE: 25

Met Ser Pro Ser Asn Gln Thr Asp Lys Leu Ala Ala
1               5                   10

<210> SEQ ID NO 26
<211> LENGTH: 12
<212> TYPE: PRT
<213> ORGANISM: Homo sapiens

<400> SEQUENCE: 26

Ser Asn Gln Thr Asp Lys Leu Ala Ala Phe Pro Glu
```

```
                        1               5                       10

<210> SEQ ID NO 27
<211> LENGTH: 12
<212> TYPE: PRT
<213> ORGANISM: Homo sapiens

<400> SEQUENCE: 27

Thr Asp Lys Leu Ala Ala Phe Pro Glu Asp Arg Ser
1               5                       10

<210> SEQ ID NO 28
<211> LENGTH: 12
<212> TYPE: PRT
<213> ORGANISM: Homo sapiens

<400> SEQUENCE: 28

Leu Ala Ala Phe Pro Glu Asp Arg Ser Gln Pro Gly
1               5                       10

<210> SEQ ID NO 29
<211> LENGTH: 12
<212> TYPE: PRT
<213> ORGANISM: Homo sapiens

<400> SEQUENCE: 29

Phe Pro Glu Asp Arg Ser Gln Pro Gly Gln Asp Cys
1               5                       10

<210> SEQ ID NO 30
<211> LENGTH: 12
<212> TYPE: PRT
<213> ORGANISM: Homo sapiens

<400> SEQUENCE: 30

Asp Arg Ser Gln Pro Gly Gln Asp Cys Arg Phe Arg
1               5                       10

<210> SEQ ID NO 31
<211> LENGTH: 12
<212> TYPE: PRT
<213> ORGANISM: Homo sapiens

<400> SEQUENCE: 31

Gln Pro Gly Gln Asp Cys Arg Phe Arg Val Thr Gln
1               5                       10

<210> SEQ ID NO 32
<211> LENGTH: 12
<212> TYPE: PRT
<213> ORGANISM: Homo sapiens

<400> SEQUENCE: 32

Gln Asp Cys Arg Phe Arg Val Thr Gln Leu Pro Asn
1               5                       10

<210> SEQ ID NO 33
<211> LENGTH: 12
<212> TYPE: PRT
<213> ORGANISM: Homo sapiens

<400> SEQUENCE: 33

Arg Phe Arg Val Thr Gln Leu Pro Asn Gly Arg Asp
1               5                       10
```

```
<210> SEQ ID NO 34
<211> LENGTH: 12
<212> TYPE: PRT
<213> ORGANISM: Homo sapiens

<400> SEQUENCE: 34

Val Thr Gln Leu Pro Asn Gly Arg Asp Phe His Met
1               5                   10

<210> SEQ ID NO 35
<211> LENGTH: 12
<212> TYPE: PRT
<213> ORGANISM: Homo sapiens

<400> SEQUENCE: 35

Leu Pro Asn Gly Arg Asp Phe His Met Ser Val Val
1               5                   10

<210> SEQ ID NO 36
<211> LENGTH: 12
<212> TYPE: PRT
<213> ORGANISM: Homo sapiens

<400> SEQUENCE: 36

Gly Arg Asp Phe His Met Ser Val Val Arg Ala Arg
1               5                   10

<210> SEQ ID NO 37
<211> LENGTH: 12
<212> TYPE: PRT
<213> ORGANISM: Homo sapiens

<400> SEQUENCE: 37

Phe His Met Ser Val Val Arg Ala Arg Arg Asn Asp
1               5                   10

<210> SEQ ID NO 38
<211> LENGTH: 12
<212> TYPE: PRT
<213> ORGANISM: Homo sapiens

<400> SEQUENCE: 38

Ser Val Val Arg Ala Arg Arg Asn Asp Ser Gly Thr
1               5                   10

<210> SEQ ID NO 39
<211> LENGTH: 12
<212> TYPE: PRT
<213> ORGANISM: Homo sapiens

<400> SEQUENCE: 39

Arg Ala Arg Arg Asn Asp Ser Gly Thr Tyr Leu Cys
1               5                   10

<210> SEQ ID NO 40
<211> LENGTH: 12
<212> TYPE: PRT
<213> ORGANISM: Homo sapiens

<400> SEQUENCE: 40

Arg Asn Asp Ser Gly Thr Tyr Leu Cys Gly Ala Ile
1               5                   10

<210> SEQ ID NO 41
```

```
<211> LENGTH: 12
<212> TYPE: PRT
<213> ORGANISM: Homo sapiens

<400> SEQUENCE: 41

Ser Gly Thr Tyr Leu Cys Gly Ala Ile Ser Leu Ala
1               5                   10

<210> SEQ ID NO 42
<211> LENGTH: 12
<212> TYPE: PRT
<213> ORGANISM: Homo sapiens

<400> SEQUENCE: 42

Tyr Leu Cys Gly Ala Ile Ser Leu Ala Pro Lys Ala
1               5                   10

<210> SEQ ID NO 43
<211> LENGTH: 12
<212> TYPE: PRT
<213> ORGANISM: Homo sapiens

<400> SEQUENCE: 43

Gly Ala Ile Ser Leu Ala Pro Lys Ala Gln Ile Lys
1               5                   10

<210> SEQ ID NO 44
<211> LENGTH: 12
<212> TYPE: PRT
<213> ORGANISM: Homo sapiens

<400> SEQUENCE: 44

Ser Leu Ala Pro Lys Ala Gln Ile Lys Glu Ser Leu
1               5                   10

<210> SEQ ID NO 45
<211> LENGTH: 12
<212> TYPE: PRT
<213> ORGANISM: Homo sapiens

<400> SEQUENCE: 45

Pro Lys Ala Gln Ile Lys Glu Ser Leu Arg Ala Glu
1               5                   10

<210> SEQ ID NO 46
<211> LENGTH: 12
<212> TYPE: PRT
<213> ORGANISM: Homo sapiens

<400> SEQUENCE: 46

Gln Ile Lys Glu Ser Leu Arg Ala Glu Leu Arg Val
1               5                   10

<210> SEQ ID NO 47
<211> LENGTH: 12
<212> TYPE: PRT
<213> ORGANISM: Homo sapiens

<400> SEQUENCE: 47

Glu Ser Leu Arg Ala Glu Leu Arg Val Thr Glu Arg
1               5                   10

<210> SEQ ID NO 48
<211> LENGTH: 12
<212> TYPE: PRT
```

```
<213> ORGANISM: Homo sapiens

<400> SEQUENCE: 48

Arg Ala Glu Leu Arg Val Thr Glu Arg Arg Ala Glu
1               5                   10

<210> SEQ ID NO 49
<211> LENGTH: 12
<212> TYPE: PRT
<213> ORGANISM: Homo sapiens

<400> SEQUENCE: 49

Leu Arg Val Thr Glu Arg Arg Ala Glu Val Pro Thr
1               5                   10

<210> SEQ ID NO 50
<211> LENGTH: 12
<212> TYPE: PRT
<213> ORGANISM: Homo sapiens

<400> SEQUENCE: 50

Thr Glu Arg Arg Ala Glu Val Pro Thr Ala His Pro
1               5                   10

<210> SEQ ID NO 51
<211> LENGTH: 12
<212> TYPE: PRT
<213> ORGANISM: Homo sapiens

<400> SEQUENCE: 51

Arg Ala Glu Val Pro Thr Ala His Pro Ser Pro Ser
1               5                   10

<210> SEQ ID NO 52
<211> LENGTH: 12
<212> TYPE: PRT
<213> ORGANISM: Homo sapiens

<400> SEQUENCE: 52

Val Pro Thr Ala His Pro Ser Pro Ser Pro Arg Pro
1               5                   10

<210> SEQ ID NO 53
<211> LENGTH: 12
<212> TYPE: PRT
<213> ORGANISM: Homo sapiens

<400> SEQUENCE: 53

Ala His Pro Ser Pro Ser Pro Arg Pro Ala Gly Gln
1               5                   10

<210> SEQ ID NO 54
<211> LENGTH: 12
<212> TYPE: PRT
<213> ORGANISM: Homo sapiens

<400> SEQUENCE: 54

Ser Pro Ser Pro Arg Pro Ala Gly Gln Phe Gln Leu
1               5                   10

<210> SEQ ID NO 55
<211> LENGTH: 11
<212> TYPE: PRT
<213> ORGANISM: Homo sapiens
```

```
<400> SEQUENCE: 55

Pro Arg Pro Ala Gly Gln Phe Gln Thr Leu Val
1               5                   10

<210> SEQ ID NO 56
<211> LENGTH: 24
<212> TYPE: PRT
<213> ORGANISM: Homo sapiens

<400> SEQUENCE: 56

Gly Trp Phe Leu Asp Ser Pro Asp Arg Pro Trp Asn Gly Ala Ile Ser
1               5                   10                  15

Leu Ala Pro Lys Ala Gln Ile Lys
            20

<210> SEQ ID NO 57
<211> LENGTH: 24
<212> TYPE: PRT
<213> ORGANISM: Homo sapiens

<400> SEQUENCE: 57

Gly Ala Ile Ser Leu Ala Pro Lys Ala Gln Ile Lys Gly Trp Phe Leu
1               5                   10                  15

Asp Ser Pro Asp Arg Pro Trp Asn
            20

<210> SEQ ID NO 58
<211> LENGTH: 12
<212> TYPE: PRT
<213> ORGANISM: Homo sapiens

<400> SEQUENCE: 58

Phe Val Leu Asn Trp Tyr Arg Met Ser Pro Ser Asn
1               5                   10

<210> SEQ ID NO 59
<211> LENGTH: 12
<212> TYPE: PRT
<213> ORGANISM: Homo sapiens

<400> SEQUENCE: 59

Asn Trp Tyr Arg Met Ser Pro Ser Asn Gln Thr Asp
1               5                   10

<210> SEQ ID NO 60
<211> LENGTH: 12
<212> TYPE: PRT
<213> ORGANISM: Homo sapiens

<400> SEQUENCE: 60

Arg Met Ser Pro Ser Asn Gln Thr Asp Lys Leu Ala
1               5                   10

<210> SEQ ID NO 61
<211> LENGTH: 12
<212> TYPE: PRT
<213> ORGANISM: Homo sapiens

<400> SEQUENCE: 61

Tyr Leu Ser Gly Ala Ile Ser Leu Ala Pro Lys Ala
1               5                   10

<210> SEQ ID NO 62
```

```
<211> LENGTH: 12
<212> TYPE: PRT
<213> ORGANISM: Homo sapiens

<400> SEQUENCE: 62

Pro Ser Pro Ser Pro Arg Pro Ala Gly Gln Phe Gln
1               5                   10

<210> SEQ ID NO 63
<211> LENGTH: 18
<212> TYPE: PRT
<213> ORGANISM: Homo sapiens

<400> SEQUENCE: 63

Gly Ala Ile Ser Leu Ala Pro Lys Ala Gln Ile Lys Glu Ser Leu Arg
1               5                   10                  15

Ala Glu

<210> SEQ ID NO 64
<211> LENGTH: 15
<212> TYPE: PRT
<213> ORGANISM: Homo sapiens

<400> SEQUENCE: 64

Ile Ser Leu Ala Pro Lys Ala Gln Ile Lys Glu Ser Leu Arg Ala
1               5                   10                  15

<210> SEQ ID NO 65
<211> LENGTH: 15
<212> TYPE: PRT
<213> ORGANISM: Homo sapiens

<400> SEQUENCE: 65

Pro Gly Trp Phe Leu Asp Ser Pro Asp Arg Pro Trp Asn Pro Pro
1               5                   10                  15

<210> SEQ ID NO 66
<211> LENGTH: 15
<212> TYPE: PRT
<213> ORGANISM: Homo sapiens

<400> SEQUENCE: 66

Phe Leu Asp Ser Pro Asp Arg Pro Trp Asn Pro Pro Thr Phe Ser
1               5                   10                  15

<210> SEQ ID NO 67
<211> LENGTH: 15
<212> TYPE: PRT
<213> ORGANISM: Homo sapiens

<400> SEQUENCE: 67

Ser Pro Asp Arg Pro Trp Asn Pro Pro Thr Phe Ser Pro Ala Leu
1               5                   10                  15

<210> SEQ ID NO 68
<211> LENGTH: 15
<212> TYPE: PRT
<213> ORGANISM: Homo sapiens

<400> SEQUENCE: 68

Arg Pro Trp Asn Pro Pro Thr Phe Ser Pro Ala Leu Leu Val Val
1               5                   10                  15

<210> SEQ ID NO 69
```

```
<211> LENGTH: 15
<212> TYPE: PRT
<213> ORGANISM: Homo sapiens

<400> SEQUENCE: 69

Asn Pro Pro Thr Phe Ser Pro Ala Leu Leu Val Val Thr Glu Gly
1               5                   10                  15

<210> SEQ ID NO 70
<211> LENGTH: 15
<212> TYPE: PRT
<213> ORGANISM: Homo sapiens

<400> SEQUENCE: 70

Thr Phe Ser Pro Ala Leu Leu Val Val Thr Glu Gly Asp Asn Ala
1               5                   10                  15

<210> SEQ ID NO 71
<211> LENGTH: 15
<212> TYPE: PRT
<213> ORGANISM: Homo sapiens

<400> SEQUENCE: 71

Pro Ala Leu Leu Val Val Thr Glu Gly Asp Asn Ala Thr Phe Thr
1               5                   10                  15

<210> SEQ ID NO 72
<211> LENGTH: 15
<212> TYPE: PRT
<213> ORGANISM: Homo sapiens

<400> SEQUENCE: 72

Leu Val Val Thr Glu Gly Asp Asn Ala Thr Phe Thr Cys Ser Phe
1               5                   10                  15

<210> SEQ ID NO 73
<211> LENGTH: 15
<212> TYPE: PRT
<213> ORGANISM: Homo sapiens

<400> SEQUENCE: 73

Thr Glu Gly Asp Asn Ala Thr Phe Thr Cys Ser Phe Ser Asn Thr
1               5                   10                  15

<210> SEQ ID NO 74
<211> LENGTH: 15
<212> TYPE: PRT
<213> ORGANISM: Homo sapiens

<400> SEQUENCE: 74

Asp Asn Ala Thr Phe Thr Cys Ser Phe Ser Asn Thr Ser Glu Ser
1               5                   10                  15

<210> SEQ ID NO 75
<211> LENGTH: 15
<212> TYPE: PRT
<213> ORGANISM: Homo sapiens

<400> SEQUENCE: 75

Thr Phe Thr Cys Ser Phe Ser Asn Thr Ser Glu Ser Phe Val Leu
1               5                   10                  15

<210> SEQ ID NO 76
<211> LENGTH: 15
<212> TYPE: PRT
```

<213> ORGANISM: Homo sapiens

<400> SEQUENCE: 76

Cys Ser Phe Ser Asn Thr Ser Glu Ser Phe Val Leu Asn Trp Tyr
1               5                   10                  15

<210> SEQ ID NO 77
<211> LENGTH: 15
<212> TYPE: PRT
<213> ORGANISM: Homo sapiens

<400> SEQUENCE: 77

Ser Asn Thr Ser Glu Ser Phe Val Leu Asn Trp Tyr Arg Met Ser
1               5                   10                  15

<210> SEQ ID NO 78
<211> LENGTH: 15
<212> TYPE: PRT
<213> ORGANISM: Homo sapiens

<400> SEQUENCE: 78

Ser Glu Ser Phe Val Leu Asn Trp Tyr Arg Met Ser Pro Ser Asn
1               5                   10                  15

<210> SEQ ID NO 79
<211> LENGTH: 15
<212> TYPE: PRT
<213> ORGANISM: Homo sapiens

<400> SEQUENCE: 79

Phe Val Leu Asn Trp Tyr Arg Met Ser Pro Ser Asn Gln Thr Asp
1               5                   10                  15

<210> SEQ ID NO 80
<211> LENGTH: 15
<212> TYPE: PRT
<213> ORGANISM: Homo sapiens

<400> SEQUENCE: 80

Asn Trp Tyr Arg Met Ser Pro Ser Asn Gln Thr Asp Lys Leu Ala
1               5                   10                  15

<210> SEQ ID NO 81
<211> LENGTH: 15
<212> TYPE: PRT
<213> ORGANISM: Homo sapiens

<400> SEQUENCE: 81

Arg Met Ser Pro Ser Asn Gln Thr Asp Lys Leu Ala Ala Phe Pro
1               5                   10                  15

<210> SEQ ID NO 82
<211> LENGTH: 15
<212> TYPE: PRT
<213> ORGANISM: Homo sapiens

<400> SEQUENCE: 82

Pro Ser Asn Gln Thr Asp Lys Leu Ala Ala Phe Pro Glu Asp Arg
1               5                   10                  15

<210> SEQ ID NO 83
<211> LENGTH: 15
<212> TYPE: PRT
<213> ORGANISM: Homo sapiens

<400> SEQUENCE: 83

Gln Thr Asp Lys Leu Ala Ala Phe Pro Glu Asp Arg Ser Gln Pro
1               5                   10                  15

<210> SEQ ID NO 84
<211> LENGTH: 15
<212> TYPE: PRT
<213> ORGANISM: Homo sapiens

<400> SEQUENCE: 84

Lys Leu Ala Ala Phe Pro Glu Asp Arg Ser Gln Pro Gly Gln Asp
1               5                   10                  15

<210> SEQ ID NO 85
<211> LENGTH: 15
<212> TYPE: PRT
<213> ORGANISM: Homo sapiens

<400> SEQUENCE: 85

Ala Phe Pro Glu Asp Arg Ser Gln Pro Gly Gln Asp Cys Arg Phe
1               5                   10                  15

<210> SEQ ID NO 86
<211> LENGTH: 15
<212> TYPE: PRT
<213> ORGANISM: Homo sapiens

<400> SEQUENCE: 86

Glu Asp Arg Ser Gln Pro Gly Gln Asp Cys Arg Phe Arg Val Thr
1               5                   10                  15

<210> SEQ ID NO 87
<211> LENGTH: 15
<212> TYPE: PRT
<213> ORGANISM: Homo sapiens

<400> SEQUENCE: 87

Ser Gln Pro Gly Gln Asp Cys Arg Phe Arg Val Thr Gln Leu Pro
1               5                   10                  15

<210> SEQ ID NO 88
<211> LENGTH: 15
<212> TYPE: PRT
<213> ORGANISM: Homo sapiens

<400> SEQUENCE: 88

Gly Gln Asp Cys Arg Phe Arg Val Thr Gln Leu Pro Asn Gly Arg
1               5                   10                  15

<210> SEQ ID NO 89
<211> LENGTH: 15
<212> TYPE: PRT
<213> ORGANISM: Homo sapiens

<400> SEQUENCE: 89

Cys Arg Phe Arg Val Thr Gln Leu Pro Asn Gly Arg Asp Phe His
1               5                   10                  15

<210> SEQ ID NO 90
<211> LENGTH: 15
<212> TYPE: PRT
<213> ORGANISM: Homo sapiens

<400> SEQUENCE: 90

```
Arg Val Thr Gln Leu Pro Asn Gly Arg Asp Phe His Met Ser Val
1               5                   10                  15
```

<210> SEQ ID NO 91
<211> LENGTH: 15
<212> TYPE: PRT
<213> ORGANISM: Homo sapiens

<400> SEQUENCE: 91

```
Gln Leu Pro Asn Gly Arg Asp Phe His Met Ser Val Val Arg Ala
1               5                   10                  15
```

<210> SEQ ID NO 92
<211> LENGTH: 15
<212> TYPE: PRT
<213> ORGANISM: Homo sapiens

<400> SEQUENCE: 92

```
Asn Gly Arg Asp Phe His Met Ser Val Val Arg Ala Arg Arg Asn
1               5                   10                  15
```

<210> SEQ ID NO 93
<211> LENGTH: 15
<212> TYPE: PRT
<213> ORGANISM: Homo sapiens

<400> SEQUENCE: 93

```
Asp Phe His Met Ser Val Val Arg Ala Arg Arg Asn Asp Ser Gly
1               5                   10                  15
```

<210> SEQ ID NO 94
<211> LENGTH: 15
<212> TYPE: PRT
<213> ORGANISM: Homo sapiens

<400> SEQUENCE: 94

```
Met Ser Val Val Arg Ala Arg Arg Asn Asp Ser Gly Thr Tyr Leu
1               5                   10                  15
```

<210> SEQ ID NO 95
<211> LENGTH: 15
<212> TYPE: PRT
<213> ORGANISM: Homo sapiens

<400> SEQUENCE: 95

```
Val Arg Ala Arg Arg Asn Asp Ser Gly Thr Tyr Leu Cys Gly Ala
1               5                   10                  15
```

<210> SEQ ID NO 96
<211> LENGTH: 15
<212> TYPE: PRT
<213> ORGANISM: Homo sapiens

<400> SEQUENCE: 96

```
Arg Arg Asn Asp Ser Gly Thr Tyr Leu Cys Gly Ala Ile Ser Leu
1               5                   10                  15
```

<210> SEQ ID NO 97
<211> LENGTH: 15
<212> TYPE: PRT
<213> ORGANISM: Homo sapiens

<400> SEQUENCE: 97

```
Asp Ser Gly Thr Tyr Leu Cys Gly Ala Ile Ser Leu Ala Pro Lys
1               5                   10                  15
```

<210> SEQ ID NO 98
<211> LENGTH: 15
<212> TYPE: PRT
<213> ORGANISM: Homo sapiens

<400> SEQUENCE: 98

Thr Tyr Leu Cys Gly Ala Ile Ser Leu Ala Pro Lys Ala Gln Ile
1               5                   10                  15

<210> SEQ ID NO 99
<211> LENGTH: 15
<212> TYPE: PRT
<213> ORGANISM: Homo sapiens

<400> SEQUENCE: 99

Cys Gly Ala Ile Ser Leu Ala Pro Lys Ala Gln Ile Lys Glu Ser
1               5                   10                  15

<210> SEQ ID NO 100
<211> LENGTH: 15
<212> TYPE: PRT
<213> ORGANISM: Homo sapiens

<400> SEQUENCE: 100

Ile Ser Leu Ala Pro Lys Ala Gln Ile Lys Glu Ser Leu Arg Ala
1               5                   10                  15

<210> SEQ ID NO 101
<211> LENGTH: 15
<212> TYPE: PRT
<213> ORGANISM: Homo sapiens

<400> SEQUENCE: 101

Ala Pro Lys Ala Gln Ile Lys Glu Ser Leu Arg Ala Glu Leu Arg
1               5                   10                  15

<210> SEQ ID NO 102
<211> LENGTH: 15
<212> TYPE: PRT
<213> ORGANISM: Homo sapiens

<400> SEQUENCE: 102

Ala Gln Ile Lys Glu Ser Leu Arg Ala Glu Leu Arg Val Thr Glu
1               5                   10                  15

<210> SEQ ID NO 103
<211> LENGTH: 15
<212> TYPE: PRT
<213> ORGANISM: Homo sapiens

<400> SEQUENCE: 103

Lys Glu Ser Leu Arg Ala Glu Leu Arg Val Thr Glu Arg Arg Ala
1               5                   10                  15

<210> SEQ ID NO 104
<211> LENGTH: 15
<212> TYPE: PRT
<213> ORGANISM: Homo sapiens

<400> SEQUENCE: 104

Leu Arg Ala Glu Leu Arg Val Thr Glu Arg Arg Ala Glu Val Pro
1               5                   10                  15

-continued

<210> SEQ ID NO 105
<211> LENGTH: 15
<212> TYPE: PRT
<213> ORGANISM: Homo sapiens

<400> SEQUENCE: 105

Glu Leu Arg Val Thr Glu Arg Arg Ala Glu Val Pro Thr Ala His
1 5 10 15

<210> SEQ ID NO 106
<211> LENGTH: 15
<212> TYPE: PRT
<213> ORGANISM: Homo sapiens

<400> SEQUENCE: 106

Val Thr Glu Arg Arg Ala Glu Val Pro Thr Ala His Pro Ser Pro
1 5 10 15

<210> SEQ ID NO 107
<211> LENGTH: 15
<212> TYPE: PRT
<213> ORGANISM: Homo sapiens

<400> SEQUENCE: 107

Arg Arg Ala Glu Val Pro Thr Ala His Pro Ser Pro Ser Pro Arg
1 5 10 15

<210> SEQ ID NO 108
<211> LENGTH: 15
<212> TYPE: PRT
<213> ORGANISM: Homo sapiens

<400> SEQUENCE: 108

Glu Val Pro Thr Ala His Pro Ser Pro Ser Pro Arg Pro Ala Gly
1 5 10 15

<210> SEQ ID NO 109
<211> LENGTH: 15
<212> TYPE: PRT
<213> ORGANISM: Homo sapiens

<400> SEQUENCE: 109

Thr Ala His Pro Ser Pro Ser Pro Arg Pro Ala Gly Gln Phe Gln
1 5 10 15

<210> SEQ ID NO 110
<211> LENGTH: 18
<212> TYPE: PRT
<213> ORGANISM: Measles morbillivirus

<400> SEQUENCE: 110

Lys Leu Leu Ser Leu Ile Lys Gly Val Ile Val His Arg Leu Glu Gly
1 5 10 15

Val Glu

<210> SEQ ID NO 111
<211> LENGTH: 19
<212> TYPE: PRT
<213> ORGANISM: Clostridium tetani

<400> SEQUENCE: 111

Asn Ser Val Asp Asp Ala Leu Ile Asn Ser Thr Ile Tyr Ser Tyr Phe
1 5 10 15

Pro Ser Val

```
<210> SEQ ID NO 112
<211> LENGTH: 17
<212> TYPE: PRT
<213> ORGANISM: Clostridium tetani

<400> SEQUENCE: 112

Pro Gly Ile Asn Gly Lys Ala Ile His Leu Val Asn Asn Gln Ser Ser
1               5                   10                  15

Glu

<210> SEQ ID NO 113
<211> LENGTH: 15
<212> TYPE: PRT
<213> ORGANISM: Clostridium tetani

<400> SEQUENCE: 113

Gln Tyr Ile Lys Ala Asn Ser Lys Phe Ile Gly Ile Thr Glu Leu
1               5                   10                  15

<210> SEQ ID NO 114
<211> LENGTH: 21
<212> TYPE: PRT
<213> ORGANISM: Clostridium tetani

<400> SEQUENCE: 114

Phe Asn Asn Phe Thr Val Ser Phe Trp Leu Arg Val Pro Lys Val Ser
1               5                   10                  15

Ala Ser His Leu Glu
            20

<210> SEQ ID NO 115
<211> LENGTH: 15
<212> TYPE: PRT
<213> ORGANISM: Measles morbillivirus

<400> SEQUENCE: 115

Leu Ser Glu Ile Lys Gly Val Ile Val His Arg Leu Glu Gly Val
1               5                   10                  15

<210> SEQ ID NO 116
<211> LENGTH: 15
<212> TYPE: PRT
<213> ORGANISM: Hepatitis B virus

<400> SEQUENCE: 116

Phe Phe Leu Leu Thr Arg Ile Leu Thr Ile Pro Gln Ser Leu Asn
1               5                   10                  15

<210> SEQ ID NO 117
<211> LENGTH: 21
<212> TYPE: PRT
<213> ORGANISM: Plasmodium sp.

<400> SEQUENCE: 117

Thr Cys Gly Val Gly Val Arg Val Arg Ser Arg Val Asn Ala Ala Asn
1               5                   10                  15

Lys Lys Pro Glu Leu
            20

<210> SEQ ID NO 118
<211> LENGTH: 535
<212> TYPE: PRT
```

<213> ORGANISM: Corynebacterium diphtheriae

<400> SEQUENCE: 118

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400
```

```
Val Glu Asp Ser Ile Ile Arg Thr Gly Phe Gln Gly Glu Ser Gly His
            405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
            485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
            515                 520                 525

Leu Phe Phe Glu Ile Lys Ser
530                 535

<210> SEQ ID NO 119
<211> LENGTH: 15
<212> TYPE: PRT
<213> ORGANISM: Mus musculus

<400> SEQUENCE: 119

Ile Ser Leu His Pro Lys Ala Lys Ile Glu Glu Ser Pro Gly Ala
1               5                   10                  15
```